(12) United States Patent
Leiris et al.

(10) Patent No.: US 12,378,244 B2
(45) Date of Patent: *Aug. 5, 2025

(54) DIAZABICYCLOOCTANONES AS INHIBITORS OF SERINE β-LACTAMASES

(71) Applicant: Antabio SAS, Labege (FR)

(72) Inventors: Simon Leiris, Labege (FR); David Thomas Davies, Lebege (FR)

(73) Assignee: Antabio SAS, Labege (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/510,120

(22) Filed: Nov. 15, 2023

(65) Prior Publication Data

US 2024/0391919 A1 Nov. 28, 2024

Related U.S. Application Data

(63) Continuation of application No. 17/266,215, filed as application No. PCT/EP2019/071370 on Aug. 8, 2019, now Pat. No. 11,905,286.

(30) Foreign Application Priority Data

Aug. 9, 2018 (EP) .................................... 18290093
Dec. 18, 2018 (EP) .................................... 18213635

(51) Int. Cl.
*A61K 31/439* (2006.01)
*C07D 471/08* (2006.01)

(52) U.S. Cl.
CPC .................................. *C07D 471/08* (2013.01)

(58) Field of Classification Search
CPC ............................... A61P 31/04; A61K 31/439
USPC ........................................................ 514/300
See application file for complete search history.

(56) References Cited

U.S. PATENT DOCUMENTS

| | | | |
|---|---|---|---|
| 11,905,286 B2 * | 2/2024 | Leiris .................... | C07D 471/08 |
| 2003/0148324 A1 | 8/2003 | Bingen et al. | |
| 2003/0199541 A1 | 10/2003 | Lampilas et al. | |
| 2004/0147826 A1 | 7/2004 | Peterson | |
| 2005/0020572 A1 | 1/2005 | Aszodi et al. | |
| 2005/0234089 A1 | 10/2005 | Meisel et al. | |
| 2012/0323010 A1 | 12/2012 | Ronsheim et al. | |
| 2013/0225554 A1 | 8/2013 | Maiti et al. | |
| 2014/0088068 A1 | 3/2014 | Bhagwat et al. | |
| 2017/0145037 A1 | 5/2017 | Burns et al. | |
| 2017/0360810 A1 | 12/2017 | Perello Bestard et al. | |

FOREIGN PATENT DOCUMENTS

| | | |
|---|---|---|
| CN | 107501265 | 12/2017 |
| EP | 2657234 | 10/2013 |
| EP | 2857401 | 4/2015 |
| EP | 3572411 | 11/2019 |
| GB | 2533136 | 6/2016 |
| WO | WO 95/12601 | 5/1995 |
| WO | WO 00/41478 | 7/2000 |
| WO | WO 2004/005535 | 1/2001 |
| WO | WO 01/12171 | 2/2001 |
| WO | WO 02/100870 | 12/2002 |
| WO | WO 03/074553 | 9/2003 |
| WO | WO 03/078654 | 9/2003 |
| WO | WO 2005/077019 | 8/2005 |
| WO | WO 2005/097823 | 10/2005 |
| WO | WO 2006/058796 | 6/2006 |
| WO | WO 2006/059344 | 6/2006 |
| WO | WO 2006/064516 | 6/2006 |
| WO | WO 2007/095039 | 8/2007 |
| WO | WO 2007/095043 | 8/2007 |
| WO | WO 2007/135562 | 11/2007 |
| WO | WO 2008/020308 | 2/2008 |
| WO | WO 2008/038136 | 4/2008 |
| WO | WO 2008/117225 | 10/2008 |
| WO | WO 2009/008006 | 1/2009 |
| WO | WO 2009/091856 | 7/2009 |
| WO | WO 2010/001220 | 1/2010 |
| WO | WO 2010/043893 | 4/2010 |
| WO | WO 2011/009961 | 1/2011 |
| WO | WO 2011/053848 | 5/2011 |

(Continued)

OTHER PUBLICATIONS

Ball et al., "Development of a Manufacturing Route to Avibactam, a β-Lactamase Inhibitor," *Organic Process Research & Development* 20:1799-1805, 2016.

(Continued)

*Primary Examiner* — Charanjit Aulakh

(74) *Attorney, Agent, or Firm* — Klarquist Sparkman, LLP

(57) ABSTRACT

The invention relates to a compound which is a diazabicyclooctanone of Formula (I) or a pharmaceutically acceptable salt thereof:

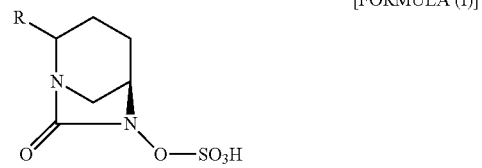

[FORMULA (I)]

wherein R is as defined herein. The compounds are useful in the treatment of bacterial infection, in particular they are useful in reducing bacterial resistance to antibiotics. They are also useful in the treatment of bacteria which express serine-β-lactamase enzymes, in combination with antibiotics.

29 Claims, 7 Drawing Sheets

(56) References Cited

FOREIGN PATENT DOCUMENTS

| | | |
|---|---|---|
| WO | WO 2012/030645 | 3/2012 |
| WO | WO 2012/073214 | 6/2012 |
| WO | WO 2012/172368 | 12/2012 |
| WO | WO 2013/014496 | 1/2013 |
| WO | WO 2013/030735 | 3/2013 |
| WO | WO 2013/038330 | 3/2013 |
| WO | WO 2013/062994 | 5/2013 |
| WO | WO 2013/062995 | 5/2013 |
| WO | WO 2013/122888 | 8/2013 |
| WO | WO 2013/149121 | 10/2013 |
| WO | WO 2013/149136 | 10/2013 |
| WO | WO 2013/150296 | 10/2013 |
| WO | WO 2014/033560 | 3/2014 |
| WO | WO 2014/052799 | 4/2014 |
| WO | WO 2014/067904 | 5/2014 |
| WO | WO 2014/091268 | 6/2014 |
| WO | WO 2014/108872 | 7/2014 |
| WO | WO 2014/114929 | 7/2014 |
| WO | WO 2014/122468 | 8/2014 |
| WO | WO 2014/140402 | 9/2014 |
| WO | WO 2014/141132 | 9/2014 |
| WO | WO 2014/198849 | 12/2014 |
| WO | WO 2015/001125 | 1/2015 |
| WO | WO 2015/059642 | 4/2015 |
| WO | WO 2015/110969 | 7/2015 |
| WO | WO 2015/114595 | 8/2015 |
| WO | WO 2015/125031 | 8/2015 |
| WO | WO 2015/128333 | 9/2015 |
| WO | WO 2015/136387 | 9/2015 |
| WO | WO 2015/148379 | 10/2015 |
| WO | WO 2015/159167 | 10/2015 |
| WO | WO 2015/159265 | 10/2015 |
| WO | WO 2015/181637 | 12/2015 |
| WO | WO 2016/081452 | 5/2016 |
| WO | WO 2016/116788 | 7/2016 |
| WO | WO 2016/128867 | 8/2016 |
| WO | WO 2016/156344 | 10/2016 |
| WO | WO 2016/156348 | 10/2016 |
| WO | WO 2016/156597 | 10/2016 |
| WO | WO 2016/177862 | 11/2016 |
| WO | WO 2017/002083 | 1/2017 |
| WO | WO 2017/002086 | 1/2017 |
| WO | WO 2017/002087 | 1/2017 |
| WO | WO 2017/002089 | 1/2017 |
| WO | WO 2017/030773 | 2/2017 |
| WO | WO 2017/037607 | 3/2017 |
| WO | WO 2017/096472 | 6/2017 |
| WO | WO 2017/109025 | 6/2017 |
| WO | WO 2017/156239 | 9/2017 |
| WO | WO 2017/203266 | 11/2017 |
| WO | WO 2017/216765 | 12/2017 |
| WO | WO 2018/053215 | 3/2018 |
| WO | WO 2018/060484 | 4/2018 |
| WO | WO 2018/129008 | 7/2018 |
| WO | WO 2018/141986 | 8/2018 |
| WO | WO 2018/141991 | 8/2018 |
| WO | WO 2018/208769 | 11/2018 |
| WO | WO 2019/016393 | 1/2019 |
| WO | WO 2019/093450 | 5/2019 |
| WO | WO 2020/025543 | 2/2020 |
| WO | WO 2020/025587 | 2/2020 |

OTHER PUBLICATIONS

Bredt et al., "Dehydroeampher säuren, Lauronolsäuren und Bihydrolauro-Laetone," *Ber. Deutsch. Chem. Ges.* 35:1286-1282, 1902.

Cantón et al., "Rapid evolution and spread of carbapenemases among Enterobacteriaceae in Europe," *Clinical Microbiology and Infection* 18(5):413-431, 2012.

Cheng et al., "Highly efficient synthesis of aryl and heteroaryl trifluoromethyl ketones via o-iodobenzoic acid (IBX)," *Tetrahedron Letters* 54:4483-4486, 2013.

Collet et al., "Synthesis and preliminary in vivo evaluation of new [$^{18}$F]fluoro-inositols as Positron Emission Tomography radiotracers," *Bioorganic & Medicinal Chemistry* 25:5603-5612, 2017.

Davies et al., "Discovery of ANT3310, a Novel Broad-Spectrum Serine β-Lactamase Inhibitor of the Diazabicyclooctane Class, Which Strongly Potentiates Meropenem Activity against Carbapenem-Resistant Enterobacterales and *Acinetobacter baumannii*," *Journal of Medicinal Chemistry* 63:15802-15820, 2020.

De Koning et al., "The combination of clavulanic acid and amoxycillin (Augmentin®) in the treatment of patients infected with penicillinase producing gonococci," *Journal of Antimicrobial Chemotherapy* 8:81-82, 1981.

Dondondi et al., "Stereoselective Synthesis of α- and β--ᴌ--C-Fucosyl Aldehydes and Their Utility in the Assembly of C-Fucosides of Biological Relevance," *Journal of Organic Chemistry* 69:5023-5036, 2004.

Fernández et al., "Tn Antigen Mimics Based on sp$^2$-Iminosugars with Affinity for an anti-MUC1 Antibody," *Organic Letters* 18:3890-3893, 2016.

Fujiu et al., "Introduction of a Thio Functional Group to Diazabicyclooctane: An Effective Modification to Potentiate the Activity of β-Lactams against Gram-Negative Bacteria Producing Class A, C, and D Serine β-Lactamases," *American Chemical Society Infectious Diseases*, 6:3034-3047, 2020.

Gauthier et al., "The discovery of odanacatib (MK-0822), a selective inhibitor of cathepsin K," *Bioorganic & Medicinal Chemistry Letters* 18:923-928, 2008.

Gudipati et al., "Solution-Phase Parallel Synthesis of Oligoethylene Glycol Sorting Tags. Preparation of All Four Stereoisomers of the Hydroxybutenolide Fragment of Murisolin and Related Acetogenins," *Journal of Organic Chemistry* 71:3599-3607, 2006.

He et al., "Oxidative decarboxylative radical trifluoromethylthiolation of alkyl carboxylic acids with silver(I) trifluoromethanethiolate and selectfluor," *Royal Society of Chemistry Advances* 7:880-883, 2017.

Hunsdiecker et al., "About the breakdown of the salts of aliphatic acids by bromine," *Chem. Ber.* 75:291, 1942.

Kochi, "A New Method for Halodecarboxylation of Acids Using Lead(IV) Acetate," *Journal of the American Chemical Society* 87(11):2500-2502, 1965.

Liu et al., "Synthesis and Protection of Aryl Sulfates Using the 2,2,2-Trichloroethyl Moiety," *Organic Letters* 6(2):209-212, 2004.

Liu et al., "Silver-Mediated Oxidative Trifluoromethylation of Alcohols to Alkyl Trifluoromethyl Esters," *Organic Letters* 17:5048-5051, 2015.

Mawal et al., "Ceftazidime-avibactam for the treatment of complicated urinary tract infections and complicated intra-abdominal infections," *Expert Review of Clinical Pharmacology* 8(6):691-704, 2015.

Nordmann et al., "Global Spread of Carbapenemase-producing Enterobacteriaceae," *Emerging Infectious Diseases* 17(10): 1791-1798, 2011.

Papp-Wallace et al., "New β-Lactamase Inhibitors in the Clinic," *Infectious Disease Clinics of North America* 30(2):441-464, 2016.

Taiwanese Office Action dated Apr. 29, 2021 from Application No. 108128294, with English-Language Translation (8 pages).

Vázquez-Ucha et al., "New Carbapenemase Inhibitors: Clearing the Way for the β-Lactams," *International Journal of Molecular Sciences* 21(23):9308 (31 pages), 2020.

Wityak et al., "Lead Optimization toward Proof-of-Concept Tools for Huntington's Disease within a 4-(1H-Pyrazol-4-yl)pyrimidine Class of Pan-JNK Inhibitors," *Journal of Medicinal Chemistry* 58:2967-2987, 2015.

Xu et al., "Concise Synthesis of Acyl Migration-Blocked 1,1-Difluorinated Analogues of Lysophosphatidic Acid," *Journal of Organic Chemistry* 67(20):7158-7161, 2002.

Yin et al., "Silver-Catalyzed Decarboxylative Fluorination of Aliphatic Carboxylic Acids in Aqueous Solution," *Journal of the American Chemical Society* 134:10401-10404, 2012.

\* cited by examiner

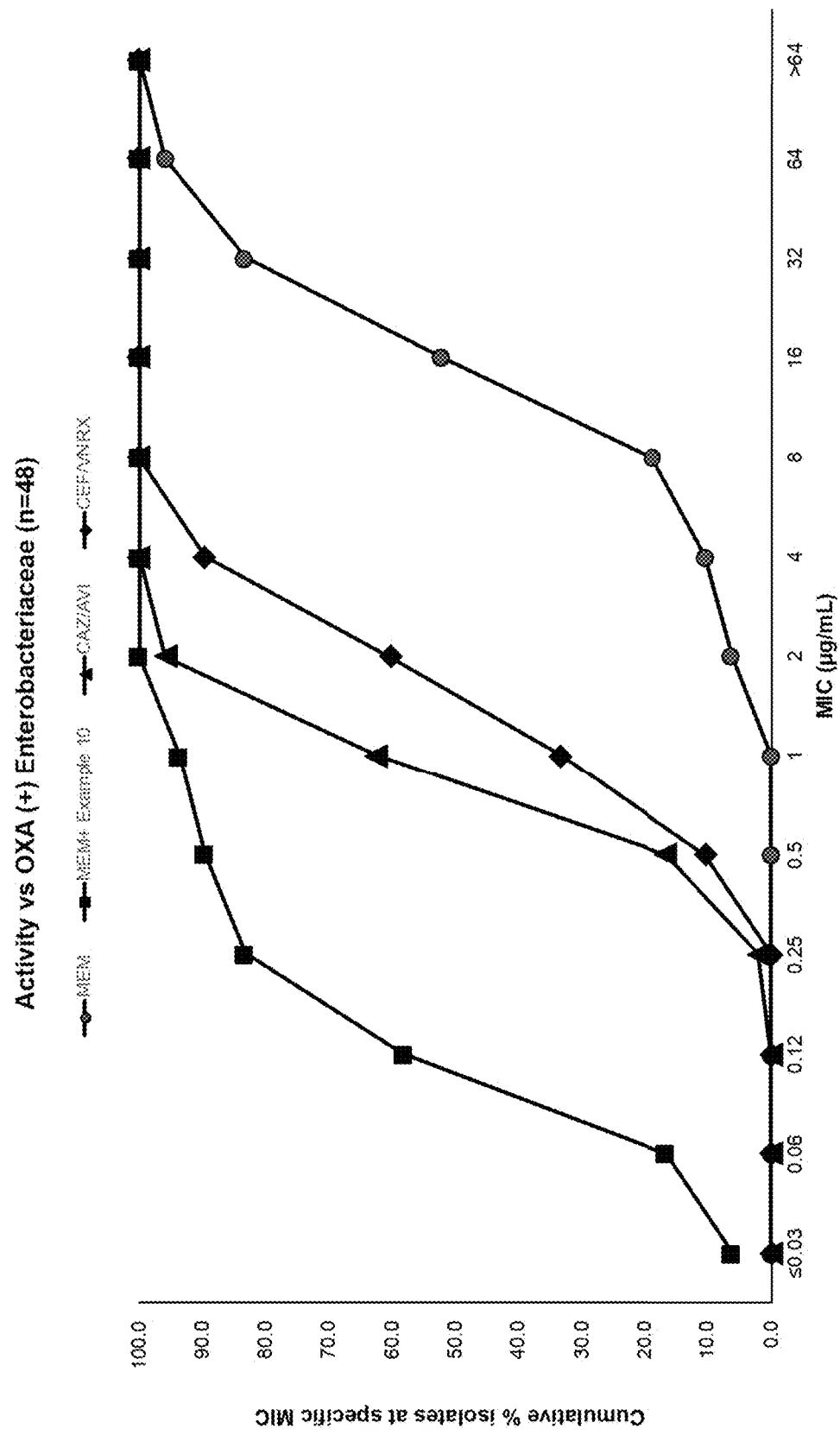

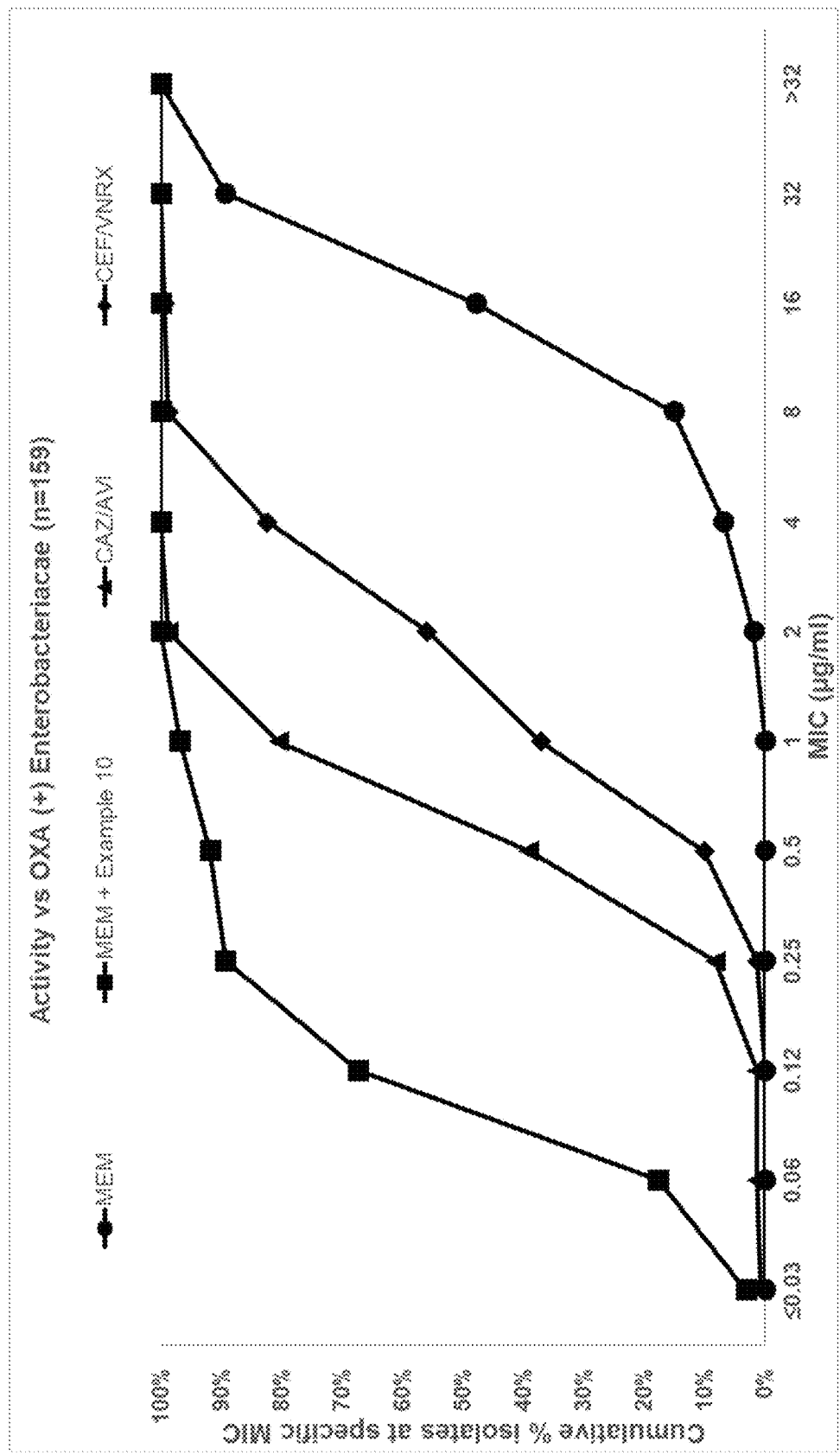

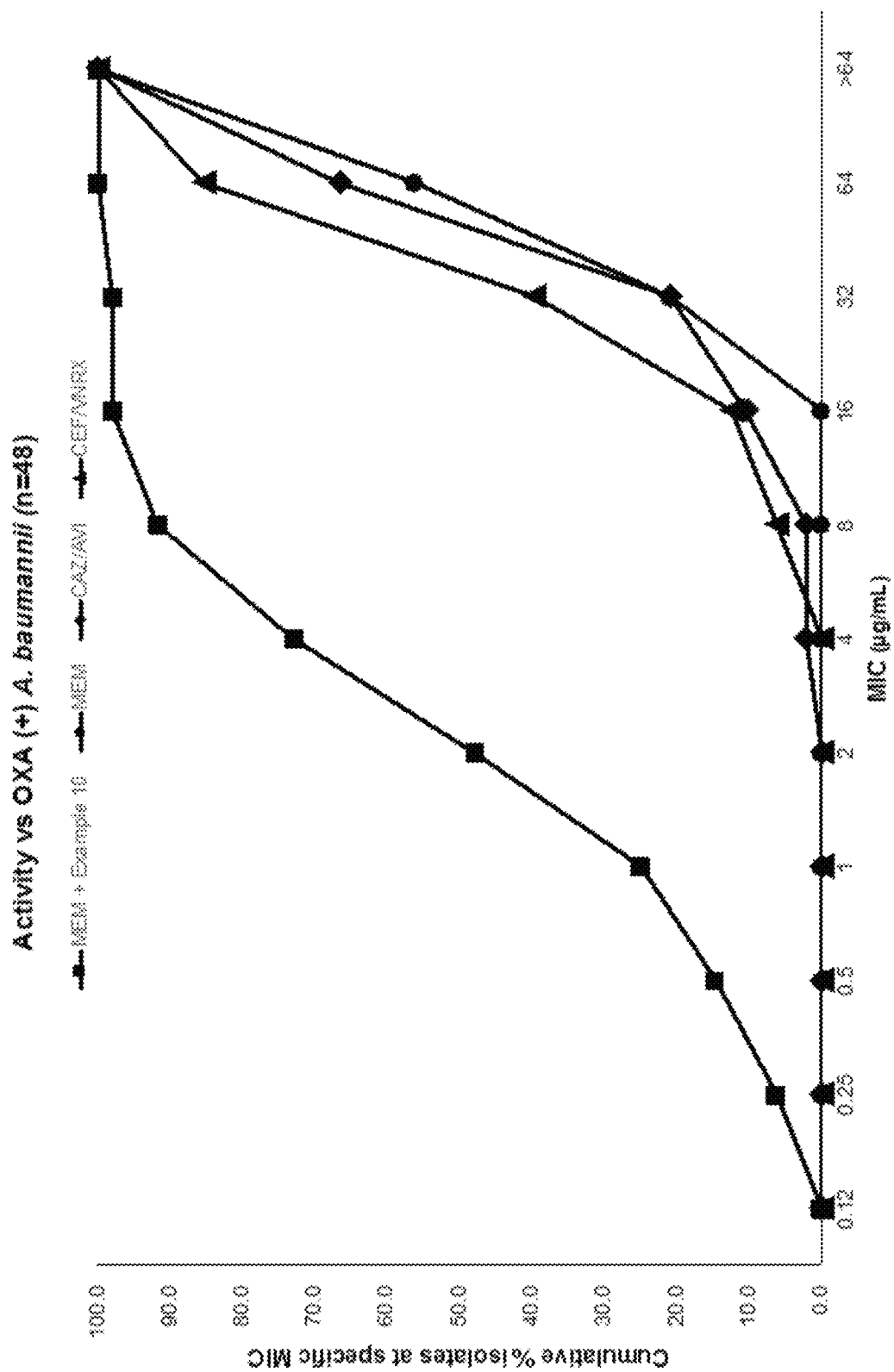

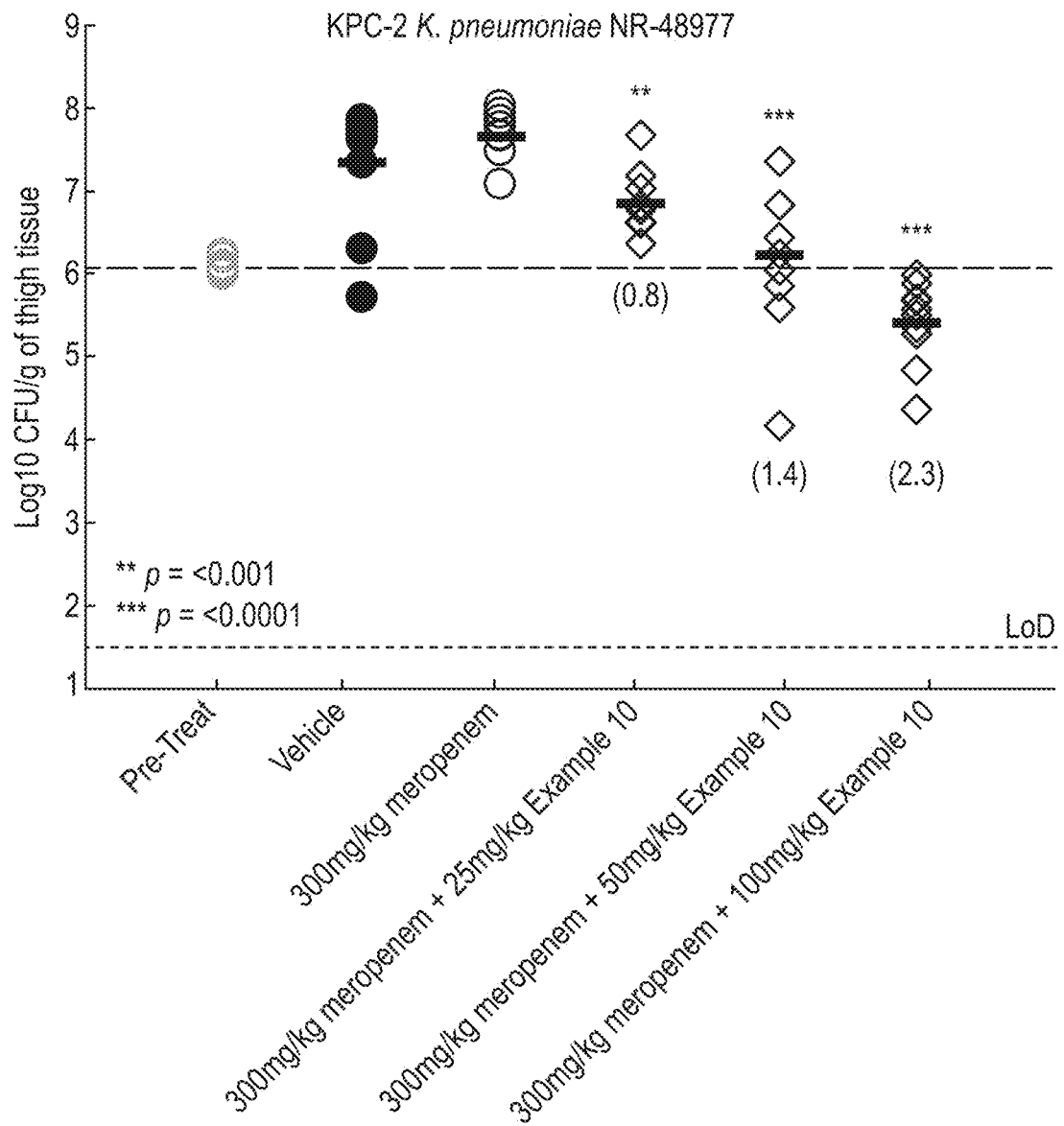

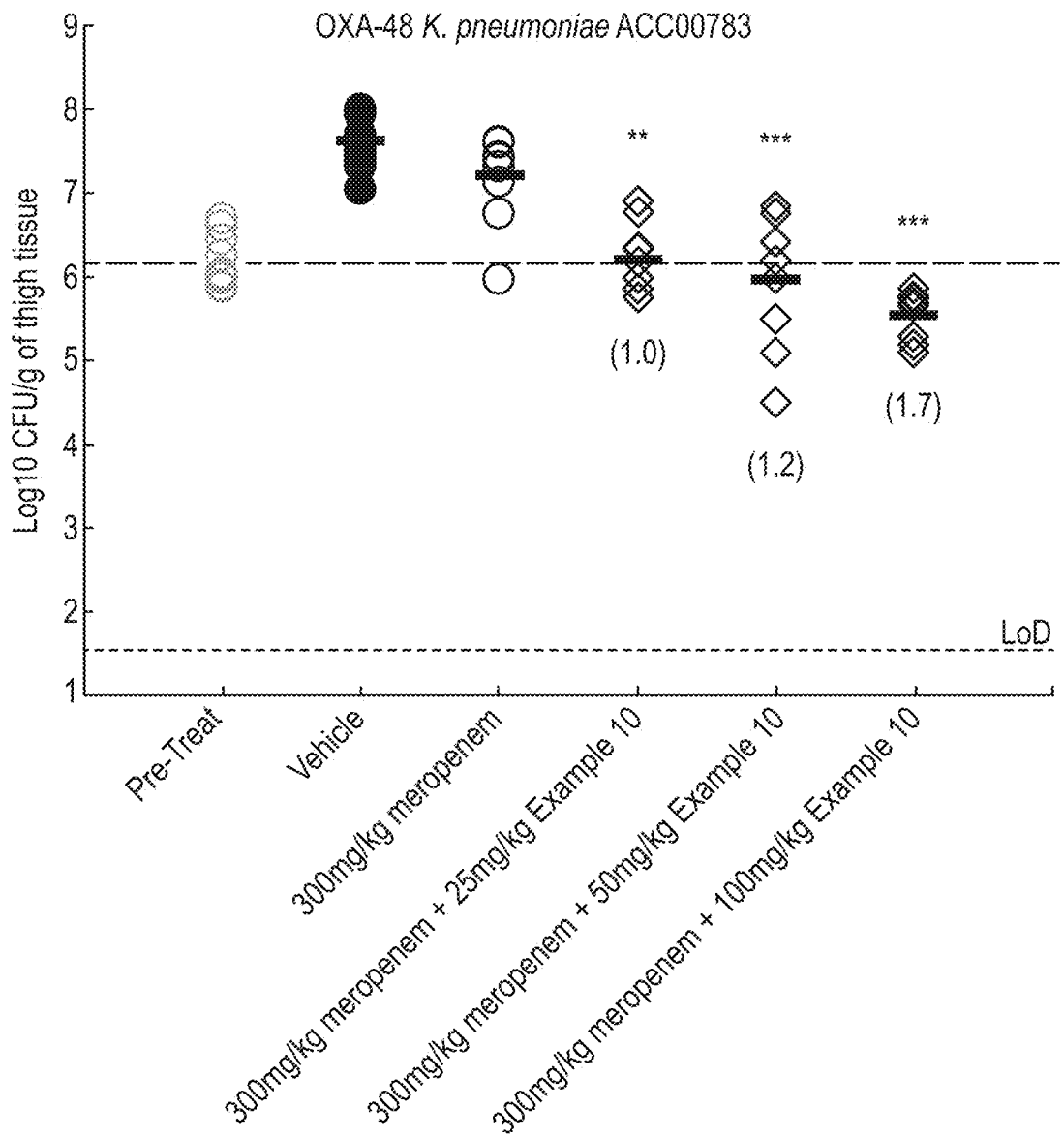

DIAZABICYCLOOCTANONES AS INHIBITORS OF SERINE β-LACTAMASES

CROSS REFERENCE TO RELATED APPLICATIONS

This is a continuation of U.S. patent application Ser. No. 17/266,215, filed on Feb. 5, 2021, which is the U.S. National Stage of International Application No. PCT/EP2019/071370, filed on Aug. 8, 2019, which in turn claims the benefit of Application Nos. EP18290093.6 filed on Aug. 9, 2018, and EP18213635.8 filed on Dec. 18, 2018. These applications are incorporated herein in their entireties.

FIELD OF THE INVENTION

The invention relates to compounds which are inhibitors of serine beta lactamase enzymes, and compositions containing the compounds. The compounds are useful in the treatment of bacterial infection. The invention also relates to combinations of the compounds with other active agents useful in the treatment of bacterial infection.

BACKGROUND

Antibiotic resistance in pathogenic bacteria is a major public health threat worldwide. Resistance of bacteria to β-lactam antibiotics caused by the hydrolysis of β-lactam antibiotics by β-lactamase enzymes is of particular concern. The enzymes effect the hydrolytic cleavage of the β-lactam ring, rendering the β-lactam antibiotic inactive. Beta-lactamases belong to two structurally and mechanistically unrelated families of enzymes: the serine β-lactamases (SBLs; classes A, C and D) which use an active serine to cleave the β-lactam in a covalent mechanism, and the metallo β-lactamases (MBLs; class B) which use metal ion catalysis to directly hydrolyze the β-lactam without the formation of a covalent intermediate.

To counter the threat of emerging resistance, in 1981 the *Streptomyces clavuligerus* natural product clavulanic acid (an SBL inhibitor: see Scheme 1 in the General Synthetic Methodology section below), was introduced as part of a combination together with the β-lactam antibiotic amoxicillin (as Augmentin) (see De Koning, G. A. et al, 1981, J. Antimicrobial Chemotherapy 8, 81-82). More recently, there has been renewed interest in the field of β-lactamase inhibitor discovery in order to counter the threat from newer β-lactamases which are not inhibited by clavulanic acid, such as the extended spectrum β-lactamases (ESBLs) and carbapenemases. This has led to the development of new synthetic classes of inhibitors, such as the diazabicyclooctanones (DBOs), as exemplified by avibactam which is in clinical use in combination with ceftazidime (Mawal, Y. et al, 2015, Expert Rev. Clin. Pharmacol. 8, (6), 691-707).

The carbapenems such as meropenem and imipenem are widely regarded as the drugs of choice for the treatment of severe infections caused by ESBL-producing Enterobacteriaceae and *Acinetobacter baumannii*. While avibactam is a good nanomolar inhibitor of many of the clinically-relevant SBLs that hydrolyse carbapenems, it is poor against (i) variants of the OXA family which are among the most prevalent carbapenemases in Europe and the Middle East; and specifically (ii) OXA producing *Acinetobacter baumannii* (declared as a top priority pathogen by the World Health Organization) (Cantón R et al, European Network on Carbapenemases, (2012), Rapid evolution and spread of carbapenemases among Enterobacteriaceae in Europe. Clin Microbiol Infect 18:413-431; and Nordmann P et al, 2011, Global spread of carbapenemase-producing Enterobacteriaceae. Emerg Infect Dis 17:1791-1798).

There is therefore a need to provide new SBL inhibitors, in particular inhibitors capable of inhibiting the OXA family of β-lactamases. There is also a need to provide broad spectrum inhibitors capable of inhibiting a range of SBLs, including the extended spectrum β-lactamases (ESBLs) and carbapenemases. There is further a need to provide inhibitors capable of inhibiting SBL is produced by *Acinetobacter baumannii*. The present invention aims to address some or all of these issues.

SUMMARY OF THE INVENTION

The present inventors have surprisingly found that novel analogues in the DBO field have unexpected activity against SBL enzymes including the OXA variants. As such, these compounds are expected to be of use as an adjunct to carbapenems in treating infectious disease.

Accordingly, the invention provides a compound as set out in aspect [1]. The compounds are useful in the treatment of bacterial infection, in particular they are useful in removing or reducing SBL-derived bacterial resistance to antibiotics. They are therefore useful in the treatment of infection caused by SBL-producing bacteria, e.g. in combination with antibiotics. Thus, the treatment or prevention of bacteria is typically carried out by administering the compound of the invention in combination with an antibiotic agent. The compounds are also useful in combination with metallo-β-lactamase (MBL) inhibitors, in particular where the bacterial infection is caused by both SBL and MBL-producing bacteria.

The present invention, in particular, provides:
1. A compound which is a diazabicyclooctanone of Formula (I) or a pharmaceutically acceptable salt thereof:

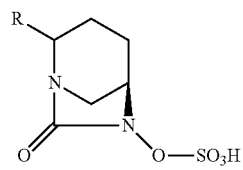

[FORMULA (I)]

wherein
R is selected from halogen, C(O)R¹, $C_{1-4}$ alkyl and L-X—R¹, wherein the $C_{1-4}$ alkyl group is substituted with at least one halogen atom and is optionally further substituted with one or two substituents R²;
R¹ is $C_{1-4}$ alkyl which is substituted with at least one halogen atom and is optionally further substituted with one or two substituents R²;
each R² is independently selected from OH; $C_{1-4}$ alkoxy which is unsubstituted or substituted with one or more halogen atoms; C(O)R³; C(O)OH; C(O)OR³; 6- to 10-membered aryl; 5- to 6-membered heteroaryl; and 4- to 6-membered heterocyclyl; wherein the aryl, heteroaryl and heterocyclyl groups are unsubstituted or substituted with one, two or three substituents selected from halogen, OH, C(O)R³, C(O)OH, C(O)OR³ and $C_{1-4}$ alkyl and $C_{1-4}$ alkoxy groups which are themselves unsubstituted or substituted with one or more halogen atoms;

R³ is C₁₋₄ alkyl which is unsubstituted or substituted with one or more halogen atoms;

L is a bond or is a C₁₋₂ alkylene group which is unsubstituted or is substituted with at least one halogen atom; and X is O or S(O)$_z$ wherein z is 0, 1 or 2.

2. A compound according to aspect 1, wherein said compound is a diazabicyclooctanone of Formula (II) or a pharmaceutically acceptable salt thereof or Formula (III) or a pharmaceutically acceptable salt thereof:

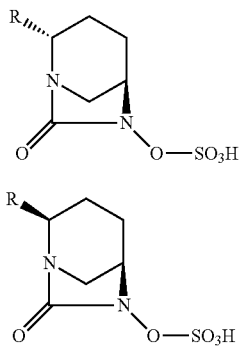

Formula (II)

Formula (III)

wherein R is halogen.

3. A compound according to aspect 1 or aspect 2, wherein R is fluorine or chlorine.

4. A compound according to any one of aspects 1 to 3, wherein the compound is a diazabicyclooctanone of Formula (II) or a pharmaceutically acceptable salt thereof and wherein R is fluorine or chlorine.

5. A compound according to any one of aspects 1 to 3, wherein the compound is a diazabicyclooctanone of Formula (III) or a pharmaceutically acceptable salt thereof and wherein R is fluorine or chlorine.

6. A compound according to any one of aspects 1 to 3, wherein said compound is selected from (2R,5R)-2-fluoro-7-oxo-1,6-diazabicyclo[3.2.1]octan-6-yl hydrogen sulphate;

(2S, 5R)-2-fluoro-7-oxo-1,6-diazabicyclo [3.2.1] octan-6-yl hydrogen sulphate;

(2R,5R)-2-chloro-7-oxo-1,6-diazabicyclo[3.2.1]octan-6-yl hydrogen sulphate;

and pharmaceutically acceptable salts thereof.

7. A compound according to aspect 1 which is a diazabicyclooctanone of Formula (II) or a pharmaceutically acceptable salt thereof:

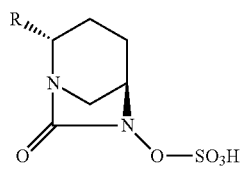

[FORMULA (II)]

wherein R is as defined in aspect 1.

8. A compound according to aspect 1 which is a diazabicyclooctanone of Formula (II) or a pharmaceutically acceptable salt thereof:

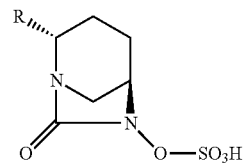

[FORMULA (II)]

wherein

R is selected from C(O)R¹ and C₁₋₄ alkyl, wherein the C₁₋₄ alkyl group is substituted with at least one halogen atom and is optionally further substituted with one or two substituents R²;

R¹ is C₁₋₄ alkyl which is substituted with at least one halogen atom and is optionally further substituted with one or two substituents R²;

each R² is independently selected from OH; C₁₋₄ alkoxy which is unsubstituted or substituted with one or more halogen atoms; C(O)R³; C(O)OH; C(O)OR³; 6- to 10-membered aryl; 5- to 6-membered heteroaryl; and 4- to 6-membered heterocyclyl; wherein the aryl, heteroaryl and heterocyclyl groups are unsubstituted or substituted with one, two or three substituents selected from halogen, OH, C(O)R³, C(O)OH, C(O)OR³ and C₁₋₄ alkyl and C₁₋₄ alkoxy groups which are themselves unsubstituted or substituted with one or more halogen atoms;

R³ is C₁₋₄ alkyl which is unsubstituted or substituted with one or more halogen atoms.

9. A compound according to aspect 8, wherein R is selected from C(O)R¹ and C₁₋₄ alkyl, wherein the C₁₋₄ alkyl group is substituted with at least one halogen atom and is optionally further substituted with one substituent R².

10. A compound according to aspect 8, wherein R¹ is C₁₋₄ alkyl which is substituted with at least one halogen atom and is optionally further substituted with one substituent selected from OH and C₁₋₄ alkoxy which is itself unsubstituted or substituted with one or more halogen atoms.

11. A compound according to any one of aspects 8 to 10, wherein R¹ is C₁₋₂ alkyl, wherein the C₁₋₂ alkyl group is substituted with at least two halogen atoms selected from fluorine and chlorine.

12. A compound according to any one of aspects 8 to 11, wherein each R² is independently selected from OH; C₁₋₂ alkoxy which is itself unsubstituted or substituted with one or more halogen atoms; C(O)OR³, wherein R³ is unsubstituted C₁₋₂ alkyl; and unsubstituted 5- to 6-membered heteroaryl.

13. A compound according to any one of aspects 8 to 12, wherein each R² is independently selected from OH; OMe; C(O)OMe; and unsubstituted thiazolyl.

14. A compound according to aspect 8, wherein:

R is selected from C(O)R¹ and C₁₋₄ alkyl, wherein the C₁₋₄ alkyl group is substituted with at least one halogen atom and is optionally further substituted with one substituent R²;

R¹ is C₁₋₄ alkyl which is substituted with at least one halogen atom and is optionally further substituted with one substituent selected from OH and C₁₋₄ alkoxy, the C₁₋₄ alkyl group being unsubstituted or substituted with one or more halogen atoms; and R² is selected from OH; C₁₋₂ alkoxy which is itself unsubstituted or substituted with one or more halogen atoms; C(O)OR³, wherein R³ is unsubstituted C₁₋₂ alkyl; and unsubstituted 5- to 6-membered heteroaryl.

15. A compound according to aspect 8, wherein:
R is selected from C(O)R$^1$ and C$_{1-4}$ alkyl, preferably C$_{1-2}$ alkyl, wherein the alkyl group is substituted with at least one halogen atom and is optionally further substituted with one substituent R$^2$;
R$^1$ is C$_{1-2}$ alkyl, wherein the C$_{1-2}$ alkyl group is substituted with at least two halogen atoms selected from fluorine or chlorine; and
R$^2$ is selected from OH; OMe; C(O)OMe; and unsubstituted thiazolyl.

16. A compound according to any one of aspects 8 to 15, wherein R is C$_{1-2}$ alkyl, wherein the C$_{1-2}$ alkyl group is substituted with at least one halogen atom and is optionally further substituted with one substituent R$^2$.

17. A compound according to aspect 8, wherein R is selected from CF$_3$, CHF$_2$, CHCl$_2$, CCl$_3$, CH$_2$F, CF$_2$CH$_3$, CF$_2$CH$_2$CO$_2$Me, COCF$_3$, CF$_2$-thiazolyl, CF$_2$CH$_2$OCH$_3$, CF$_2$CH$_2$CH$_2$OH, CH(OH)CF$_3$, CH$_2$CF$_3$ and CF$_2$-oxetanyl.

18. A compound according to aspect 8, wherein R is selected from CF$_3$, CHF$_2$ and CHCl$_2$.

19. A compound according to aspect 7, wherein R is -L-X-R$^1$, wherein:
L is a bond or is an unsubstituted C$_1$ alkylene group;
X is O or S;
R$^1$ is a C$_1$ alkyl group substituted by 1, 2 or 3 halogen groups;
wherein preferably R is selected from —CH$_2$—O—CF$_3$ and —S—CF$_3$.

20. A compound according to any one of the preceding aspects, which compound is a sodium salt of a compound of Formula (I).

21. A compound according to any one of aspects 2 to 20, which compound is a sodium salt of a compound of Formula (II) or Formula (III), preferably the compound is a sodium salt of a compound of Formula (II).

22. A pharmaceutical composition comprising a compound according to any one of the preceding aspects and a pharmaceutically acceptable carrier or diluent and optionally further comprising (i) an antibiotic agent and/or (ii) a metallo-β-lactamase inhibitor.

23. A combination of a compound according to any one of aspects 1 to 21 and one or more of (i) an antibiotic agent and (ii) a metallo-β-lactamase inhibitor.

24. A compound according to any one of aspects 1 to 21 for use in the treatment or prevention of bacterial infection by co-administration with an antibiotic agent and/or a metallo-β-lactamase inhibitor.

25. An antibiotic agent for use in the treatment or prevention of bacterial infection by co-administration with a compound according to any one of aspects 1 to 21, and optionally a metallo-β-lactamase inhibitor.

26. A metallo-β-lactamase inhibitor for use in the treatment or prevention of bacterial infection by co-administration with a compound according to any one of aspects 1 to 21, and optionally an antibiotic agent.

27. A composition according to aspect 22, a combination according to aspect 23 or a compound, antibiotic agent or metallo-β-lactamase inhibitor for use according to any one of aspects 24 to 26, wherein the antibiotic agent is a β-lactam antibiotic, preferably a β-lactam antibiotic selected from carbapenems, penicillins, cephalosporins and penems.

28. A composition, combination or compound, antibiotic agent or metallo-β-lactamase inhibitor for use according to aspect 27, wherein the antibiotic agent is a carbapenem antibiotic, preferably the antibiotic agent is meropenem.

29. A compound according to any one of aspects 1 to 21, or a composition or combination according to any one of aspects 22, 23, 27 or 28 for use in the removal or reduction of antibiotic resistance in Gram-negative bacteria.

30. A compound according to any one of aspects 1 to 21, or a composition or combination according to any one of aspects 22, 23, 27 or 28 for use in the treatment or prevention of bacterial infection.

31. A compound, antibiotic agent, metallo-β-lactamase inhibitor, composition or combination for use according to any one of aspects 24 to 30 wherein the Gram-negative bacteria are selected from Enterobacteriaceae, Pseudomonadaceae and Moraxellaceae, or the bacterial infection is caused by bacteria selected from Enterobacteriaceae, Pseudomonadaceae and Moraxellaceae.

32. A compound, antibiotic agent, metallo-β-lactamase inhibitor, composition or combination for use according to aspect 31 wherein the bacteria selected from Enterobacteriaceae, Pseudomonadaceae and Moraxellaceae are selected from *Klebsiella pneumoniae, Escherichia coli, Enterobacter Cloacae, Pseudomonas aeruginosa, Burkholderia cepacia* and *Acinetobacter baumannii*.

33. A compound, antibiotic agent, metallo-β-lactamase inhibitor, composition or combination for use according to aspect 31 wherein the bacterial infection is caused by Carbapenem Resistant Enterobacteriaceae.

34. A composition, combination or compound, antibiotic agent or metallo-β-lactamase inhibitor for use according to any one of aspects 22 to 33, wherein the metallo-β-lactamase inhibitor is a compound of Formula (A) or Formula (B) or a pharmaceutically acceptable salt thereof

[FORMULA (A)]

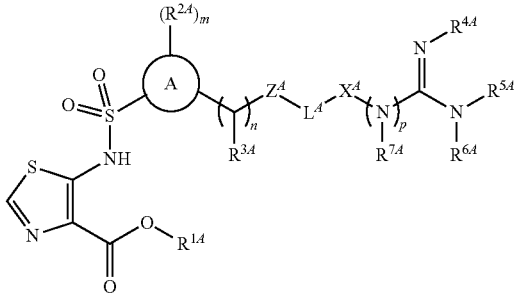

[FORMULA (B)]

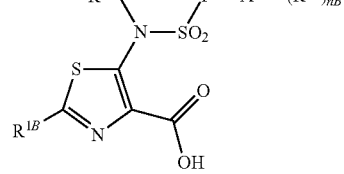

wherein R$^{1A}$, (A), m, R$^{2A}$, n, R$^{3A}$, Z$^A$, L$^A$, X$^A$, p, R$^{4A}$, R$^{5A}$, R$^{6A}$, R$^{7A}$, R$^{1B}$, R$^{11B}$, Y$^B$, A$^B$, R$^{2B}$ and n$^B$ are as defined herein;
wherein preferably the metallo-β-lactamase inhibitor is a compound of Formula (A) or a pharmaceutically acceptable salt thereof.

35. A composition, combination or compound, antibiotic agent or metallo-β-lactamase inhibitor for use according to aspect 34, wherein the metallo-β-lactamase inhibitor is a compound of Formula (A) or a pharmaceutically acceptable salt thereof, wherein $R^{1A}$ is selected from H, $R^{1b}$ and —CH$_2$OC(O)R$^{1b}$, wherein $R^{1b}$ is selected from an unsubstituted C$_1$ to C$_4$ alkyl group and phenyl;

(A)

is a cyclic group selected from C$_6$ to C$_{10}$ aryl, 5- to 10-membered heteroaryl, and 4- to 10-membered carbocyclic and heterocyclic groups;

each $R^{2A}$ is independently selected from:
(i) halo or $R^8$;
(ii) C$_{1-3}$ alkyl, O(C$_{1-3}$ alkyl), S(C$_{1-3}$ alkyl), SO(C$_{1-3}$ alkyl) or SO$_2$(C$_{1-3}$ alkyl), any of which may optionally be substituted with 1, 2 or 3 halo substituents and/or one $R^8$ substituent; and
(iii) NR$^a$C(O)R$^c$, and NR$^a$C(O)NR$^b$R$^c$, wherein each Ra and Rb is independently selected from hydrogen and unsubstituted C$_{1-2}$ alkyl and each R$^c$ is unsubstituted C$_{1-2}$ alkyl;

and
each $R^8$ is independently selected from CN, OH, —C(O)NR$^f$R$^g$, —NR$^f$R$^g$, —NR$^{10}$C(NR$^{11}$)R$^{12}$, —C(NR$^{10}$)NR$^{11}$R$^{12}$, and —NR$^{10}$C(NR$^{11}$)NR$^{12}$R$^{13}$; wherein each of R$^f$ and R$^g$ is independently H or unsubstituted C$_{1-2}$ alkyl;
m is 0, 1, 2 or 3
$R^{3A}$ is selected from hydrogen and a C$_1$ to C$_3$ alkyl group which is unsubstituted or is substituted with 1, 2 or 3 substituents selected from halogen, —OR$^{10}$, and —NR$^{10}$R$^{11}$;
n is 0 or 1
$Z^A$ is a bond or is selected from —NR$^{10}$C(O)—, —C(O)NR$^{10}$—, —NR$^{10}$C(O)NR$^{11}$—, —NR$^{10}$C(O)O—, —OC(O)NR$^{10}$, —NR$^{10}$C(O)S—, —SC(O)NR$^{10}$, —NR$^{10}$C(NR$^{11}$)—, —C(NR$^{10}$)NR$^{11}$—, —NR$^{10}$C(NR$^{11}$)NR$^{12}$—, —NR$^{10}$C(N$^+$R$^{11}$R$^{12}$)—, —C(N$^+$R$^{10}$R$^{11}$)NR$^{12}$—, —NR$^{10}$C(N$^+$R$^{11}$R$^{12}$)NR$^{13}$—, —NR$^{10}$C(NR$^{11}$)O—, —OC(NR$^{10}$)NR$^{11}$, —NR$^{10}$C(N$^+$R$^{11}$R$^{12}$)O—, —OC(N$^+$R$^{10}$R$^{11}$)NR$^{12}$—, —NR$^{10}$C(NR$^{11}$)S—, —SC(NR$^{10}$)NR$^{11}$, —NR$^{10}$C(N$^+$R$^{11}$R$^{12}$)S—, —SC(N$^+$R$^{10}$R$^{11}$)NR$^{12}$—, —C(O)NR$^{15}$—, —NR$^{10}$C(O)NR$^{15}$—, —OC(O)NR$^{15}$, —SC(O)NR$^{15}$, —C(NR$^{10}$)NR$^{15}$—, —NR$^{10}$C(NR$^{11}$)NR$^{15}$—, —C(N$^+$R$^{10}$R$^{11}$)NR$^{15}$—, —NR$^{10}$C(N$^+$R$^{11}$R$^{12}$)NR$^{15}$—, —OC(NR$^{10}$)NR$^{15}$, —OC(N$^+$R$^{10}$R$^{11}$)NR$^{15}$—, —SC(NR$^{10}$)NR$^{15}$, and —SC(N$^+$R$^{10}$R$^{11}$)NR$^{15}$—.
$L^A$ is a bond or is selected from C$_{1-4}$ alkylene, C$_{2-4}$ alkenylene, C$_{2-4}$ alkynylene, C$_{1-3}$ alkylene-(C$_{3-6}$cycloalkylene)-C$_{1-3}$ alkylene, C$_{1-4}$ alkylene-(C$_{3-6}$cycloalkylene) and (C$_{3-6}$cycloalkylene)-C$_{1-4}$ alkylene, wherein L is unsubstituted or is substituted with 1 or 2 substituents selected from halogen, —OR$^{10}$, and —NR$^{11}$R$^{11}$; or L is —C(R$^{10}$)=N—;
$X^A$ is a bond or, when L is other than a bond or —C(R$^{10}$)=N—, X is a bond or is selected from —NR$^{10}$—, —O—, —NR$^{10}$C(NR$^{11}$)—, and —C(NR$^{10}$)—;
p is 0 or 1;
$R^{4A}$ is selected from H, —CN and C$_1$ to C$_3$ alkyl which is unsubstituted or is substituted with 1, 2 or 3 substituents selected from halogen, —OR$^{10}$, —NR$^{10}$R$^{11}$, and —CN;

or $R^{4A}$ is joined together with $R^{5A}$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted C$_1$ to C$_2$ alkyl, halogen, —OR$^{10}$, —NR$^{10}$R$^{11}$, and —CN;

$R^{5A}$ is selected from H, —CN and C$_1$ to C$_3$ alkyl which is unsubstituted or is substituted with 1, 2 or 3 substituents selected from halogen, —OR$^{10}$, —NR$^{10}$R$^{11}$, and —CN;

or $R^{5A}$ is joined together with $R^{4A}$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted C$_1$ to C$_2$ alkyl, halogen, —OR$^{10}$, —NR$^{10}$R$^{11}$, and —CN;

or $R^{5A}$ is joined together with $R^6$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted C$_1$ to C$_2$ alkyl, halogen, —OR$^{10}$, —NR$^{10}$R$^{11}$, and —CN;

$R^{6A}$ is selected from H, —CN and C$_1$ to C$_3$ alkyl which is unsubstituted or is substituted with 1, 2 or 3 substituents selected from halogen, —OR$^{10}$, —NR$^{10}$R$^{11}$, and —CN;

or $R^{6A}$ is joined together with $R^{5A}$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted C$_1$ to C$_2$ alkyl, halogen, —OR$^{10}$, —NR$^{10}$R$^{11}$, and —CN;

or $R^{6A}$ is joined together with $R^{7A}$ if present to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted C$_1$ to C$_2$ alkyl, halogen, —OR$^{10}$, —NR$^{10}$R$^{11}$, and —CN;

$R^{7A}$ if present is selected from H, —CN and C$_1$ to C$_3$ alkyl which is unsubstituted or is substituted with 1, 2 or 3 substituents selected from halogen, —OR$^{10}$, —NR$^{10}$R$^{11}$, and —CN;

or $R^{7A}$ is joined together with $R^{6A}$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted C$_1$ to C$_2$ alkyl, halogen, —OR$^{10}$, —NR$^{10}$R$^{11}$, and —CN;

each $R^{10}$, $R^{11}$, $R^{12}$, $R^{13}$ and $R^{14}$ is independently H or methyl;

each $R^{15}$ is independently substituted C$_1$ to C$_4$ alkyl or unsubstituted C$_2$ to C$_4$ alkyl, wherein when $R^{15}$ is a substituted alkyl group the alkyl group is substituted with 1, 2 or 3 substituents independently selected from halogen, CN, OR$^{10}$ and —NR$^{10}$R$^{11}$.

36. A composition, combination or compound, antibiotic agent or metallo-β-lactamase inhibitor for use according to aspect 35, wherein the metallo-β-lactamase inhibitor is a compound of Formula (A) or a pharmaceutically acceptable salt thereof, wherein R¹ᴬ is H;

(A) is selected from phenyl, cyclohexane, piperidine, pyridazine, pyridine and thiazole;
m is 1 or 2;
each R²ᴬ is independently selected from:
  halo, CN, OH, —C(O)NRᶠRᵍ, —NRᶠRᵍ; wherein each of Rᶠ and Rᵍ is independently H or methyl; and
  $C_{1-2}$ alkyl, O($C_{1-2}$ alkyl), S($C_{1-2}$ alkyl), SO($C_{1-2}$ alkyl) any of which may optionally be substituted with 1, 2 or 3 substituents selected from halo, CN, OH;
n is 0;
Zᴬ is selected from —NR¹⁰C(O)—, —C(O)NR¹⁰—, and —NR¹⁰C(O)NR¹¹—;
Lᴬ is a bond or is selected from $C_{1-3}$ alkylene and $C_{2-3}$ alkenylene.
Xᴬ is a bond;
p is 0; or p is 1 and R⁷ᴬ is H;
R⁴ᴬ is H;
R⁵ᴬ is selected from H, —CN and $C_1$ to $C_2$ alkyl which is unsubstituted or is substituted with 1, 2 or 3 halo substituents and/or one —NR¹⁰R¹¹ substituent H; and
R⁶ᴬ is H.

37. A composition, combination or compound, antibiotic agent or metallo-β-lactamase inhibitor for use according to any one of aspects 34 to 36, wherein the metallo-β-lactamase inhibitor is selected from:
5-[[4-[(2-guanidinoacetyl)amino]-3-(trifluoromethoxy)phenyl]sulfonylamino]thiazole-4-carboxylic acid;
5-[[3-fluoro-4-[[(2-guanidinoacetyl)amino]methyl]phenyl]sulfonylamino]thiazole-4-carboxylic acid;
5-[[3-fluoro-4-(guanidinomethyl)phenyl]sulfonylamino]thiazole-4-carboxylic acid;
5-[[3-fluoro-4-(2-guanidinoethylsulfanylcarbonylamino)phenyl]sulfonylamino]thiazole-4-carboxylic acid;
5-[[4-[2-[(2-amino-2-imino-ethyl)amino]-2-oxo-ethyl]-3-fluoro-phenyl]sulfonylamino]thiazole-4-carboxylic acid;
5-[[3-carbamoyl-4-[(2-guanidinoacetyl)amino]phenyl]sulfonylamino]thiazole-4-carboxylic acid;
5-[[3-cyano-4-[(2-guanidinoacetyl)amino]phenyl]sulfonylamino]thiazole-4-carboxylic acid;
5-[[3-fluoro-4-(2-guanidinoethoxycarbonylamino)phenyl]sulfonylamino]thiazole-4-carboxylic acid;
5-[(4-guanidinophenyl)sulfonylamino]thiazole-4-carboxylic acid;
5-[[4-[2-(2-carbamimidoylhydrazino)-2-oxo-ethyl]-3-fluoro-phenyl]sulfonylamino]thiazole-4-carboxylic acid;
5-[[3-chloro-4-[(2-guanidinoacetyl)amino]phenyl]sulfonylamino]thiazole-4-carboxylic acid;
5-[[4-[(2-guanidinoacetyl)amino]-3-methoxy-phenyl]sulfonylamino]thiazole-4-carboxylic acid;
5-[[4-[[2-(2-carbamimidoylhydrazino)acetyl]amino]-3-fluoro-phenyl]sulfonylamino]thiazole-4-carboxylic acid;
5-[[4-[[(2E)-2-(carbamimidoylhydrazono)acetyl]amino]-3-fluoro-phenyl]sulfonylamino]thiazole-4-carboxylic acid;
5-[[4-[[2-(4,5-dihydro-1H-imidazol-2-ylamino)acetyl]amino]-3,5-difluoro-phenyl]sulfonylamino]thiazole-4-carboxylic acid;
5-[[6-[(2-guanidinoacetyl)amino]pyridazin-3-yl]sulfonylamino]thiazole-4-carboxylic acid;
5-[[4-[(2-amino-2-imino-ethyl)carbamoylamino]-3-fluoro-phenyl]sulfonylamino]thiazole-4-carboxylic acid;
5-[[3,5-difluoro-4-(guanidinocarbamoylamino)phenyl]sulfonylamino]thiazole-4-carboxylic acid;
5-[[4-[(3-amino-3-imino-propanoyl)amino]-3,5-difluoro-phenyl]sulfonylamino]thiazole-4-carboxylic acid;
5-[[4-[[3-(dimethylamino)-3-imino-propanoyl]amino]-3-fluoro-phenyl]sulfonylamino]thiazole-4-carboxylic acid;
5-[[3-fluoro-4-[(2-guanidinooxyacetyl)amino]phenyl]sulfonylamino]thiazole-4-carboxylic acid;
5-[[3-fluoro-4-[[3-imino-3-(methylamino)propanoyl]amino]phenyl]sulfonylamino]thiazole-4-carboxylic acid;
5-[[4-[3-(4,5-dihydro-1H-imidazol-2-yl)propanoylamino]-3-fluoro-phenyl]sulfonylamino]thiazole-4-carboxylic acid;
5-[[2-[(2-guanidinoacetyl)amino]thiazol-5-yl]sulfonylamino]thiazole-4-carboxylic acid;
5-[[4-[[2-[(N-cyanocarbamimidoyl)amino]acetyl]amino]-3-fluoro-phenyl]sulfonylamino]thiazole-4-carboxylic acid;
5-[[3-fluoro-4-(guanidinocarbamoylamino)phenyl]sulfonylamino]thiazole-4-carboxylic acid;
5-[[3-fluoro-4-[[2-(morpholine-4-carboximidoylamino)acetyl]amino]phenyl]sulfonylamino]thiazole-4-carboxylic acid;
5-[[4-[(3-amino-3-imino-2-methyl-propanoyl)amino]-3-fluoro-phenyl]sulfonylamino]thiazole-4-carboxylic acid;
5-[[4-[[2-(4,5-dihydro-1H-imidazol-2-yl)acetyl]amino]-3-fluoro-phenyl]sulfonylamino]thiazole-4-carboxylic acid;
5-[[4-(carbamimidoylcarbamoylamino)-3-fluoro-phenyl]sulfonylamino]thiazole-4-carboxylic acid;
5-[[4-[[(2R)-2-guanidinopropanoyl]amino]phenyl]sulfonylamino]thiazole-4-carboxylic acid;
5-[[3,5-difluoro-4-[(2-guanidinoacetyl)amino]phenyl]sulfonylamino]thiazole-4-carboxylic acid;
5-[[4-[(4-amino-4-imino-butanoyl)amino]-3-fluoro-phenyl]sulfonylamino]thiazole-4-carboxylic acid;
5-[[4-[[2-(4,5-dihydro-1H-imidazol-2-ylamino)acetyl]amino]-2,5-difluoro-phenyl]sulfonylamino]thiazole-4-carboxylic acid;
5-[[2,5-difluoro-4-[(2-guanidinoacetyl)amino]phenyl]sulfonylamino]thiazole-4-carboxylic acid;
5-[[3-fluoro-4-[[2-[(N-methylcarbamimidoyl)amino]acetyl]amino]phenyl]sulfonylamino]thiazole-4-carboxylic acid;
5-[[3-fluoro-4-[[2-(2-iminoimidazolidin-1-yl)acetyl]amino]phenyl]sulfonylamino]thiazole-4-carboxylic acid;
5-[[4-[[2-[carbamimidoyl(methyl)amino]acetyl]amino]-3-fluoro-phenyl]sulfonylamino]thiazole-4-carboxylic acid;
5-[[4-[[2-[[N-(2-aminoethyl)carbamimidoyl]amino]acetyl]amino]-3-fluoro-phenyl]sulfonylamino]thiazole-4-carboxylic acid;
5-[[5-fluoro-6-[(2-guanidinoacetyl)amino]-3-pyridyl]sulfonylamino]thiazole-4-carboxylic acid;
5-[[3-fluoro-4-(3-guanidinopropanoylamino)phenyl]sulfonylamino]thiazole-4-carboxylic acid;
5-[[4-[(3-amino-3-imino-propanoyl)amino]-3-fluoro-phenyl]sulfonylamino]thiazole-4-carboxylic acid;
5-[[3,5-difluoro-4-(guanidinocarbamoylamino)phenyl]sulfonylamino]thiazole-4-carboxylic acid;
5-[[3-fluoro-4-[(2-guanidinoacetyl)amino]phenyl]sulfonylamino]thiazole-4-carboxylic acid; and
5-[[4-(2-guanidinoacetyl)amino]phenyl]sulfonylamino]thiazole-4-carboxylic acid;
5-benzenesulfonamido-1,3-thiazole-4-carboxylic acid;
5-{[(3,5-dichlorophenyl)methyl]sulfonamido}-1,3-thiazole-4-carboxylic acid;
5-(2,4,6-trimethylphenylsulfonamido)thiazole-4-carboxylic acid;
5-{[3-(trifluoromethyl)phenyl]sulfonamido}-1,3-thiazole-4-carboxylic acid;

5-(phenylmethylsulfonamido)thiazole-4-carboxylic acid;
5-(3-methoxyphenylsulfonamido)thiazole-4-carboxylic acid;
5-(2-phenylethylsulfonamido)thiazole-4-carboxylic acid;
5-(thiophene-2-sulfonamido)thiazole-4-carboxylic acid;
5-(4,5-dichlorothiophene-2-sulfonamido)thiazole-4-carboxylic acid;
5-(2,5-dichlorothiophene-3-sulfonamido)thiazole-4-carboxylic acid;
5-(2-(trifluoromethyl)phenylsulfonamido)thiazole-4-carboxylic acid;
5-(4-(trifluoromethyl)phenylsulfonamido)thiazole-4-carboxylic acid;
5-(2-chloro-5-(trifluoromethyl)phenylsulfonamido)thiazole-4-carboxylic acid;
5-(3,5-bis(trifluoromethyl)phenylsulfonamido)thiazole-4-carboxylic acid;
5-({[2-(trifluoromethyl)phenyl]methyl}sulfonamido)-1,3-thiazole-4-carboxylic acid;
5-{[(2-methylphenyl)methyl]sulfonamido}-1,3-thiazole-4-carboxylic acid;
5-((2-nitrophenyl)methylsulfonamido)thiazole-4-carboxylic acid;
5-{[(2-bromophenyl)methyl]sulfonamido}-1,3-thiazole-4-carboxylic acid;
5-(5-chlorothiophene-2-sulfonamido)thiazole-4-carboxylic acid;
5-(5-phenylthiophene-2-sulfonamido)thiazole-4-carboxylic acid;
5-(thiophene-3-sulfonamido)thiazole-4-carboxylic acid;
5-(2,5-dimethylthiophene-3-sulfonamido)thiazole-4-carboxylic acid;
5-([1,1'-biphenyl]-2-ylsulfonamido)thiazole-4-carboxylic acid;
5-((2-aminophenyl)methylsulfonamido)thiazole-4-carboxylic acid;
5-((2-acetamidophenyl)methylsulfonamido)thiazole-4-carboxylic acid;
5-((2-benzamidophenyl)methylsulfonamido)thiazole-4-carboxylic acid;
(E)-5-((2-styrylphenyl)methylsulfonamido)thiazole-4-carboxylic acid;
(E)-5-((2-(3-(dimethylamino)-3-oxoprop-1-en-1-yl)phenyl)methylsulfonamido)thiazole-4-carboxylic acid;
5-([1,1'-biphenyl]-2-ylmethylsulfonamido)thiazole-4-carboxylic acid;
5-((2-(trifluoromethoxy)phenyl)methylsulfonamido)thiazole-4-carboxylic acid;
5-((3-(trifluoromethyl)phenyl)methylsulfonamido)thiazole-4-carboxylic acid;
5-((3-bromophenyl)methylsulfonamido)thiazole-4-carboxylic acid;
5-((3-cyanophenyl)methylsulfonamido)thiazole-4-carboxylic acid;
5-((2-chlorophenyl)methylsulfonamido)thiazole-4-carboxylic acid;
5-(4-nitrophenylsulfonamido)thiazole-4-carboxylic acid;
5-({5-[5-(trifluoromethyl)-1,2-oxazol-3-yl]thiophen-2-yl}sulfonamido)-1,3-thiazole-4-carboxylic acid;
5-(1-benzothiophene-2-sulfonamido)-1,3-thiazole-4-carboxylic acid;
5-[(5-methylthiophen-2-yl)sulfonamido]-1,3-thiazole-4-carboxylic acid;
5-[(5-bromothiophen-2-yl)sulfonamido]-1,3-thiazole-4-carboxylic acid;
5-(1-benzothiophene-3-sulfonamido)-1,3-thiazole-4-carboxylic acid;
5-[(4-bromo-2,5-dichlorothiophen-3-yl)sulfonamido]-1,3-thiazole-4-carboxylic acid;
5-({[(2-chlorophenyl)methyl]sulfamoyl}amino)-1,3-thiazole-4-carboxylic acid;
5-[({[3-(trifluoromethyl)phenyl]methyl}sulfamoyl)amino]-1,3-thiazole-4-carboxylic acid;
5-[(3-bromothiophen-2-yl)sulfonamido]-1,3-thiazole-4-carboxylic acid;
5-{[(2-iodophenyl)methyl]sulfonamido}-1,3-thiazole-4-carboxylic acid;
5-{[4-phenyl-5-(trifluoromethyl)thiophen-3-yl]sulfonamido}-1,3-thiazole-4-carboxylic acid;
5-{1[(2,3-dichlorophenyl)methyl]sulfonamido}-1,3-thiazole-4-carboxylic acid;
5-{[(3,4-dichlorophenyl)methyl]sulfonamido}-1,3-thiazole-4-carboxylic acid;
5-benzylsulfonamido-2-methyl-1,3-thiazole-4-carboxylic acid;
2-methyl-5-(quinoline-8-sulfonamido)-1,3-thiazole-4-carboxylic acid;
5-benzenesulfonamido-2-methyl-1,3-thiazole-4-carboxylic acid;
5-{[(3,5-dichlorophenyl)methyl]sulfonamido}-2-methyl-1,3-thiazole-4-carboxylic acid;
5-[(2-chlorophenyl)sulfonamido]-2-methyl-1,3-thiazole-4-carboxylic acid;
2-methyl-5-[(2,4,6-trimethylphenyl)sulfonamido]-1,3-thiazole-4-carboxylic acid;
5-[(2,5-dichlorothiophen-3-yl)sulfonamido]-2-methyl-1,3-thiazole-4-carboxylic acid;
5-{[(2-bromophenyl)methyl]sulfonamido}-2-methyl-1,3-thiazole-4-carboxylic acid;
5-benzenesulfonamido-2-phenyl-1,3-thiazole-4-carboxylic acid;
5-benzenesulfonamido-2-ethyl-1,3-thiazole-4-carboxylic acid;
5-[(1-phenylethyl)sulfonamido]-1,3-thiazole-4-carboxylic acid;
5-{[6-(trifluoromethyl)pyridin-3-yl]sulfonamido}-1,3-thiazole-4-carboxylic acid;
5-[(2-phenoxyethyl)sulfonamido]-1,3-thiazole-4-carboxylic acid;
5-{[2-(1,3-dioxo-2,3-dihydro-1H-isoindol-2-yl)ethyl]sulfonamido}-1,3-thiazole-4-carboxylic acid;
5-{[2-(2-chlorophenyl)ethyl]sulfonamido}-1,3-thiazole-4-carboxylic acid;
5-({1-[5-(trifluoromethyl)pyridin-2-yl]-1H-pyrazol-4-yl}sulfonamido)-1,3-thiazole-4-carboxylic acid;
5-[(2-chlorophenyl)sulfonamido]-1,3-thiazole-4-carboxylic acid;
5-(pyridine-3-sulfonamido)-1,3-thiazole-4-carboxylic acid;
5-[(2,6-dichlorophenyl)sulfonamido]-1,3-thiazole-4-carboxylic acid;
5-(cyclohexylmethyl)sulfonamido-1,3-thiazole-4-carboxylic acid;
5-[(4-methyl-3,4-dihydro-2H-1,4-benzoxazin-7-yl)sulfonamido]-1,3-thiazole-4-carboxylic acid;
5-[(1-phenylpropyl)sulfonamido]-1,3-thiazole-4-carboxylic acid;
5-{[2-(4-methoxyphenyl)ethyl]sulfonamido}-1,3-thiazole-4-carboxylic acid;
5-({2-[3-(trifluoromethyl)phenyl]ethyl}sulfonamido)-1,3-thiazole-4-carboxylic acid;
5-{[2-(4-chlorophenyl)ethyl]sulfonamido}-1,3-thiazole-4-carboxylic acid;
5-[(piperidine-1-sulfonyl)amino]-1,3-thiazole-4-carboxylic acid;

5-[(phenylsulfamoyl)amino]-1,3-thiazole-4-carboxylic acid;
5-{[benzyl(methyl)sulfamoyl]amino}-1,3-thiazole-4-carboxylic acid;
5-[(4-acetamidophenyl)sulfonamido]-1,3-thiazole-4-carboxylic acid;
5-[(2-methoxyphenyl)sulfonamido]-1,3-thiazole-4-carboxylic acid;
5-(1,2,3,4-tetrahydronaphthalene-1-sulfonamido)-1,3-thiazole-4-carboxylic acid;
5-[(5-methyl-1-phenyl-1H-pyrazol-4-yl)sulfonamido]-1,3-thiazole-4-carboxylic acid;
5-(cyclopropylmethyl)sulfonamido-1,3-thiazole-4-carboxylic acid;
5-{[(2-methoxyphenyl)methyl]sulfonamido}-1,3-thiazole-4-carboxylic acid;
5-{[2-(2-methoxyphenyl)ethyl]sulfonamido}-1,3-thiazole-4-carboxylic acid;
5-{[2-(3-methoxyphenyl)ethyl]sulfonamido}-1,3-thiazole-4-carboxylic acid;
5-{[2-(3-chlorophenyl)ethyl]sulfonamido}-1,3-thiazole-4-carboxylic acid;
5-[(2-methanesulfonylphenyl)sulfonamido]-1,3-thiazole-4-carboxylic acid;
5-{[methyl(phenyl)sulfamoyl]amino}-1,3-thiazole-4-carboxylic acid;
5-{[4-(morpholin-4-yl)phenyl]sulfonamido}-1,3-thiazole-4-carboxylic acid;
5-[(4-cyanophenyl)sulfonamido]-1,3-thiazole-4-carboxylic acid;
5-(pyridine-2-sulfonamido)-1,3-thiazole-4-carboxylic acid;
5-[(1-methyl-1H-imidazol-2-yl)sulfonamido]-1,3-thiazole-4-carboxylic acid;
5-[(6-methoxypyridin-3-yl)sulfonamido]-1,3-thiazole-4-carboxylic acid;
5-{[4-(1H-pyrazol-1-yl)phenyl]sulfonamido}-1,3-thiazole-4-carboxylic acid;
5-[(1-ethyl-5-methyl-1H-pyrazol-4-yl)sulfonamido]-1,3-thiazole-4-carboxylic acid;
5-{[(2-chlorophenyl)methyl]sulfonamido}-2-(trifluoromethyl)-1,3-thiazole-4-carboxylic acid;
5-{1[(2-cyanophenyl)methyl]sulfonamido}-1,3-thiazole-4-carboxylic acid;
5-[(1-methyl-1H-pyrazol-3-yl)sulfonamido]-1,3-thiazole-4-carboxylic acid;
5-[(1-methyl-1H-pyrazol-5-yl)sulfonamido]-1,3-thiazole-4-carboxylic acid;
5-({1-[(benzyloxy)carbonyl]piperidin-4-yl}sulfonamido)-1,3-thiazole-4-carboxylic acid;
5-[(3-phenylpropyl)sulfonamido]-1,3-thiazole-4-carboxylic acid;
5-{1[(2-chlorophenyl)methyl]sulfonamido}-2-methyl-1,3-thiazole-4-carboxylic acid;
5-(2,3-dihydro-1H-indene-1-sulfonamido)-1,3-thiazole-4-carboxylic acid;
5-{[4-(1-methyl-1H-pyrazol-5-yl)phenyl]sulfonamido}-1,3-thiazole-4-carboxylic acid;
5-{[2-(1,2,3,4-tetrahydroquinolin-1-yl)ethyl]sulfonamido}-1,3-thiazole-4-carboxylic acid;
5-{[2-(N-phenylacetamido)ethyl]sulfonamido}-1,3-thiazole-4-carboxylic acid;
5-{[4-(3-oxomorpholin-4-yl)phenyl]sulfonamido}-1,3-thiazole-4-carboxylic acid;
5-{[4-(2-oxo-1,3-oxazolidin-3-yl)phenyl]sulfonamido}-1,3-thiazole-4-carboxylic acid;
5-[(1,2-dimethyl-1H-imidazol-4-yl)sulfonamido]-1,3-thiazole-4-carboxylic acid;
5-[(oxan-4-ylmethyl)sulfonamido]-1,3-thiazole-4-carboxylic acid;
5-[({1-[(benzyloxy)carbonyl]piperidin-4-yl}methyl)sulfonamido]-1,3-thiazole-4-carboxylic acid;
5-{[4-(2-oxopyrrolidin-1-yl)phenyl]sulfonamido}-1,3-thiazole-4-carboxylic acid;
5-({1-[6-(trifluoromethyl)pyridin-3-yl]-1H-pyrazol-4-yl}sulfonamido)-1,3-thiazole-4-carboxylic acid;
5-{[4-(1,3-oxazol-5-yl)phenyl]sulfonamido}-1,3-thiazole-4-carboxylic acid;
5-{[4-(1H-pyrazol-4-yl)phenyl]sulfonamido}-1,3-thiazole-4-carboxylic acid;
5-[(1-phenyl-1H-pyrazol-4-yl)sulfonamido]-1,3-thiazole-4-carboxylic acid;
5-{[4-(piperidin-4-yl)phenyl]sulfonamido}-1,3-thiazole-4-carboxylic acid;
5-[(4-propanamidophenyl)sulfonamido]-1,3-thiazole-4-carboxylic acid;
5-{[4-(2-hydroxyacetamido)phenyl]sulfonamido}-1,3-thiazole-4-carboxylic acid;
5-({4-[(methylcarbamoyl)amino]phenyl}sulfonamido)-1,3-thiazole-4-carboxylic acid;
5-{[(2,4-dichlorophenyl)methyl]sulfonamido}-1,3-thiazole-4-carboxylic acid;
5-{[(2-fluorophenyl)methyl]sulfonamido}-1,3-thiazole-4-carboxylic acid;
5-{1[(2,3-difluorophenyl)methyl]sulfonamido}-1,3-thiazole-4-carboxylic acid;
5-{[4-(2-methoxyacetamido)phenyl]sulfonamido}-1,3-thiazole-4-carboxylic acid;
5-{1[(2,5-dichlorophenyl)methyl]sulfonamido}-1,3-thiazole-4-carboxylic acid;
5-{1[(2,6-dichlorophenyl)methyl]sulfonamido}-1,3-thiazole-4-carboxylic acid;
5-{1[(2-chloro-6-fluorophenyl)methyl]sulfonamido}-1,3-thiazole-4-carboxylic acid;
5-{1[(2-chloro-4-fluorophenyl)methyl]sulfonamido}-1,3-thiazole-4-carboxylic acid;
5-({[2-chloro-5-(trifluoromethyl)phenyl]methyl}sulfonamido)-1,3-thiazole-4-carboxylic acid;
5-({4-[(dimethylamino)methyl]phenyl}sulfonamido)-1,3-thiazole-4-carboxylic acid;
5-{1[(2,3,5-trichlorophenyl)methyl]sulfonamido}-1,3-thiazole-4-carboxylic acid;
5-{1[(2,3-dichloro-6-fluorophenyl)methyl]sulfonamido}-1,3-thiazole-4-carboxylic acid;
5-({[2,3-dichloro-6-(trifluoromethyl)phenyl]methyl}sulfonamido)-1,3-thiazole-4-carboxylic acid;
5-{1[(4-bromo-2-chlorophenyl)methyl]sulfonamido}-1,3-thiazole-4-carboxylic acid;
5-({2-[methyl(phenyl)amino]ethyl}sulfonamido)-1,3-thiazole-4-carboxylic acid;
5-{1[(4-nitrophenyl)methyl]sulfonamido}-1,3-thiazole-4-carboxylic acid;
5-[6-(piperidin-1-yl)pyridin-3-ylsulfonamido]-1,3-thiazole-4-carboxylic acid;
5-[6-(methylamino)pyridin-3-ylsulfonamido]-1,3-thiazole-4-carboxylic acid;
5-[6-(4-methylpiperazin-1-yl)pyridin-3-ylsulfonamido]-1,3-thiazole-4-carboxylic acid;
5-(6-acetamidopyridin-3-ylsulfonamido)-1,3-thiazole-4-carboxylic acid;
5-{4-[(5-methyl-1,2-oxazol-3-yl)amino]phenylsulfonamido}-1,3-thiazole-4-carboxylic acid;
5-(6-aminopyridin-3-ylsulfonamido)-1,3-thiazole-4-carboxylic acid;

5-[(6-chloro-2H-1,3-benzodioxol-5-yl)methylsulfonamido]-1,3-thiazole-4-carboxylic acid;
5-{1[(2-chloro-6-nitrophenyl)methyl]sulfonamido}-1,3-thiazole-4-carboxylic acid;
5-(quinoline-6-sulfonamido)-1,3-thiazole-4-carboxylic acid;
5-[(2,3-dihydroindole-1-sulfonyl)amino]-1,3-thiazole-4-carboxylic acid;
5-(4-methanesulfonylphenylsulfonamido)-1,3-thiazole-4-carboxylic acid;
5-[3-(2-oxo-1,3-oxazolidin-3-yl)phenylsulfonamido]-1,3-thiazole-4-carboxylic acid;
5-[3-(2H-pyrazol-3-yl)phenylsulfonamido]-1,3-thiazole-4-carboxylic acid;
5-[2-(pyridin-3-yl)ethylsulfonamido]-1,3-thiazole-4-carboxylic acid;
5-[3-(3-oxomorpholin-4-yl)phenylsulfonamido]-1,3-thiazole-4-carboxylic acid;
5-[3-(2-oxopyrrolidin-1-yl)phenylsulfonamido]-1,3-thiazole-4-carboxylic acid;
5-[6-(piperidin-4-ylamino)pyridin-3-ylsulfonamido]-1,3-thiazole-4-carboxylic acid;
5-(6-{[2-(dimethylamino)ethyl]amino}pyridin-3-ylsulfonamido)-1,3-thiazole-4-carboxylic acid;
5-[(4-acetamidophenyl)methylsulfonamido]-1,3-thiazole-4-carboxylic acid;
5-[6-(piperazin-1-yl)pyridin-3-ylsulfonamido]-1,3-thiazole-4-carboxylic acid;
5-[6-(4-aminopiperidin-1-yl)pyridin-3-ylsulfonamido]-1,3-thiazole-4-carboxylic acid;
5-[6-(3-aminopyrrolidin-1-yl)pyridin-3-ylsulfonamido]-1,3-thiazole-4-carboxylic acid;
5-[6-(pyrrolidin-1-yl)pyridin-3-ylsulfonamido]-1,3-thiazole-4-carboxylic acid;
5-[6-(3-aminopiperidin-1-yl)pyridin-3-ylsulfonamido]-1,3-thiazole-4-carboxylic acid;
5-[6-(1,4-diazepan-1-yl)pyridin-3-ylsulfonamido]-1,3-thiazole-4-carboxylic acid;
5-[4-(pyrrolidin-3-yloxy)phenylsulfonamido]-1,3-thiazole-4-carboxylic acid;
5-[6-(3-aminoazetidin-1-yl)pyridin-3-ylsulfonamido]-1,3-thiazole-4-carboxylic acid;
5-[6-(piperidin-4-yl)pyridin-3-ylsulfonamido]-1,3-thiazole-4-carboxylic acid;
5-[6-(1,2,3,6-tetrahydropyridin-4-yl)pyridin-3-ylsulfonamido]-1,3-thiazole-4-carboxylic acid;
5-{6-[4-(2,2,2-trifluoroethyl)piperazin-1-yl]pyridin-3-ylsulfonamido}-1,3-thiazole-4-carboxylic acid;
5-[1-(2-chlorophenyl)ethylsulfonylamino]thiazole-4-carboxylic acid;
5-[1-(2-chlorophenyl)ethylsulfonylamino]thiazole-4-carboxylic acid;
5-(3-pyridylmethylsulfonylamino)thiazole-4-carboxylic acid;
5-(isoindolin-5-ylmethylsulfonylamino)thiazole-4-carboxylic acid;
R-5-[[4-[1-(2-amino-2-phenyl-acetyl)-4-piperidyl]phenyl]sulfonylamino]thiazole-4-carboxylic acid;
S-5-[[4-[1-(2-amino-2-phenyl-acetyl)-4-piperidyl]phenyl]sulfonylamino]thiazole-4-carboxylic acid;
5-[[4-[(2-aminoacetyl)amino]phenyl]sulfonylamino]thiazole-4-carboxylic acid;
5-[(4-acetamido-3-fluoro-phenyl)sulfonylamino]thiazole-4-carboxylic acid;
5-[[4-[(2-hydroxy-2-methyl-propanoyl)amino]phenyl]sulfonylamino]thiazole-4-carboxylic acid;
5-[[4-[(2-hydroxy-2-phenyl-acetyl)amino]phenyl]sulfonylamino]thiazole-4-carboxylic acid;
5-[[4-[(2-hydroxy-3-phenyl-propanoyl)amino]phenyl]sulfonylamino]thiazole-4-carboxylic acid;
5-[[2-(2-hydroxyethylamino)pyrimidin-5-yl]sulfonylamino]thiazole-4-carboxylic acid;
5-[(2-methylpyrimidin-5-yl)sulfonylamino]thiazole-4-carboxylic acid;
5-[[2-(4-pyridyl)pyrimidin-5-yl]sulfonylamino]thiazole-4-carboxylic acid;
5-[(6-methyl-3-pyridyl)sulfonylamino]thiazole-4-carboxylic acid;
5-[(2-chloro-3-nitro-phenyl)methylsulfonylamino]thiazole-4-carboxylic acid;
and pharmaceutically acceptable salts thereof.

BRIEF DESCRIPTION OF THE FIGURES

FIG. 1A-1B show MIC data (described in the Examples) showing the activity of various inhibitors against two panels (FIGS. 1A and 1B) of clinical strains of OXA positive enterobacteriaceae that are resistant to betalactam antibiotics such as meropenem, cefepime and ceftazidime. Data are shown for (i) meropenem alone ("MEM"), (ii) the clinical combination of inhibitor VNRX-5133 and antibiotic cefepime ("CEF/VNRX"); (iii) the clinical combination of inhibitor avibactam and antibiotic ceftazidime ("CAZ/AVI"); and (iv) the compound of Example 10 and the antibiotic meropenem ("MEM+Example 10").

FIG. 3 shows MIC data (described in the Examples) showing the activity of various inhibitors against *Acinetobacter baumannii*. Data are shown for (i) meropenem alone ("MEM"), (ii) the clinical combination of inhibitor VNRX-5133 and antibiotic cefepime ("CEF/VNRX"); (iii) the clinical combination of inhibitor avibactam and antibiotic ceftazidime ("CAZ/AVI"); and (iv) the compound of Example 10 and the antibiotic meropenem ("MEM+Example 10").

FIG. 4A-4C show scattergrams showing mouse thigh burdens (cfu/g) following infection with (FIG. 4A) KPC-positive *K. pneumoniae* NR-48977; (FIG. 4B) OXA-positive *K. pneumoniae* AC00783; or (FIG. 4C) OXA-positive *A. baumannii* AC00445; each for 9 hours; and treatment with meropenem alone or in combination with Example 10, as indicated on the x-axis. The geometric mean burden of each treatment is indicated by the horizontal bar, and thigh burden reduction (in Log 10) versus meropenem alone is indicated into brackets. Statistical significance is determined versus treatment with meropenem alone ( $P<0.01$; * $P<0.001$).

DETAILED DESCRIPTION OF THE INVENTION

Definitions

Figure 2:
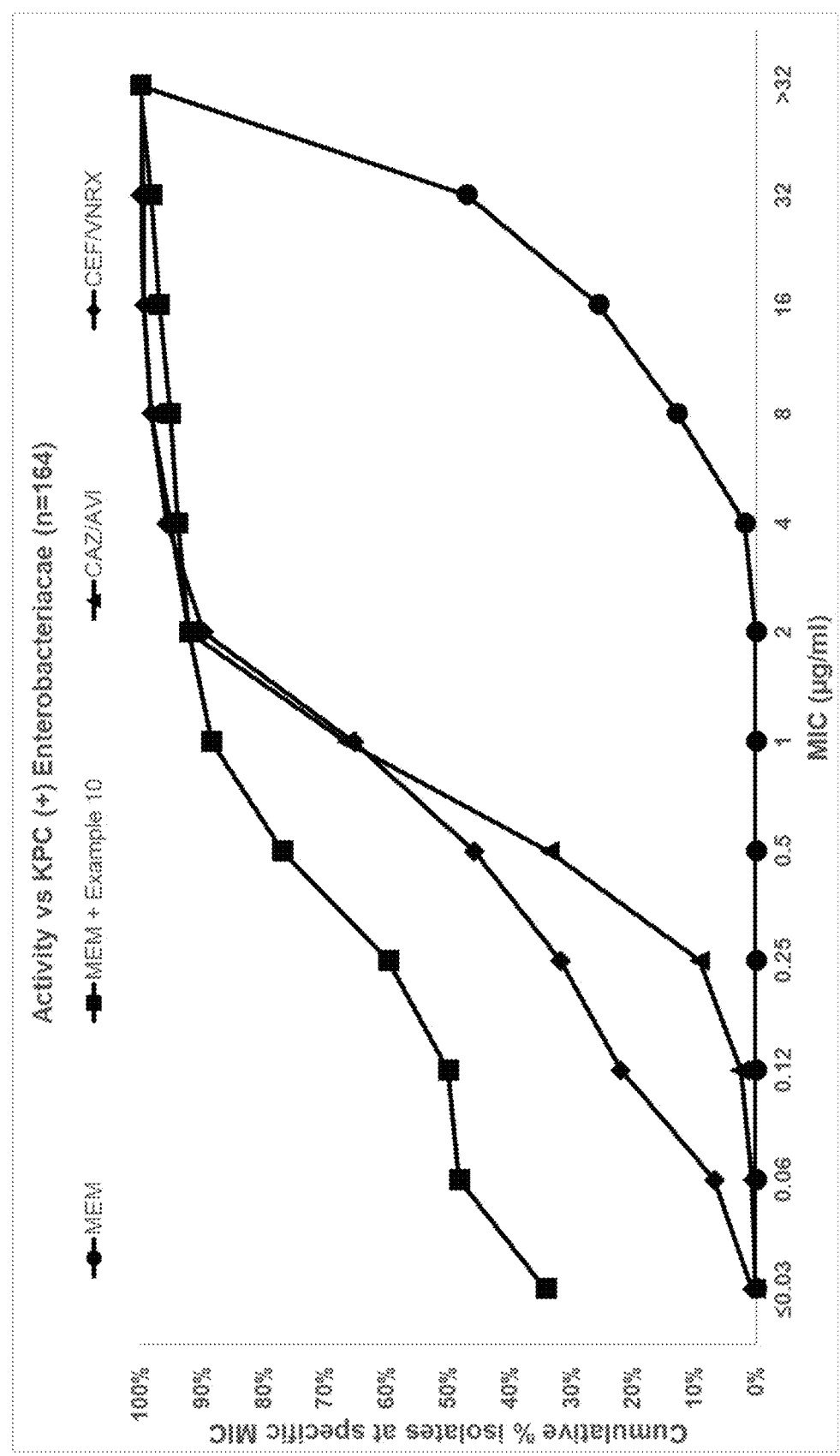
FIG. 2 shows MIC data (described in the Examples) showing the activity of various inhibitors against a panel of clinical strains of KPC positive enterobacteriaceae that are resistant to betalactam antibiotics such as meropenem, cefepime and ceftazidime. Data are shown for (i) meropenem alone ("MEM"), (ii) the clinical combination of inhibitor VNRX-5133 and antibiotic cefepime ("CEF/VNRX"); (iii) the clinical combination of inhibitor avibactam and antibiotic ceftazidime ("CAZ/AVI"); and (iv) the compound of Example 10 and the antibiotic meropenem ("MEM+Example 10").

As used herein, a $C_1$ to $C_6$ alkyl group is a linear or branched alkyl group containing from 1 to 6 carbon atoms.

A $C_1$ to $C_4$ alkyl group is a linear or branched alkyl group containing from 1 to 4 carbon atoms. A $C_1$ to $C_4$ alkyl group is often a $C_1$ to $C_3$ alkyl group or a $C_1$ to $C_2$ alkyl group. Examples of $C_1$ to $C_4$ alkyl groups include methyl, ethyl, n-propyl, iso-propyl, n-butyl, iso-butyl, sec-butyl, and tert-butyl. A $C_1$ to $C_2$ alkyl group is methyl or ethyl, typically methyl. For the avoidance of doubt, where two alkyl groups are present, the alkyl groups may be the same or different.

As used herein, a $C_1$ to $C_2$ alkylene group is an unsubstituted or substituted bidentate moiety obtained by removing two hydrogen atoms from a $C_1$ to $C_2$ alkane. The hydrogen atoms may be removed from the same carbon atom or from different carbon atoms. A $C_1$ to $C_2$ alkylene group is methylene or ethylene, typically methylene.

As used herein, a $C_{1-4}$ alkoxy is a $C_{1-4}$ alkyl group as defined above joined to an oxygen atom.

As used herein, a $C_{2-4}$ alkenyl group is a linear or branched alkenyl group containing from 2 to 4 carbon atoms and having one or more, e.g. one or two, typically one double bonds. Typically a $C_{2-4}$ alkenyl group is a $C_{2-3}$ alkenyl group. Examples of $C_{2-4}$ alkenyl groups include ethenyl, propenyl and butenyl. A $C_{2-4}$ alkenylene group is an unsubstituted or substituted bidentate moiety obtained by removing two hydrogen atoms from a $C_{2-4}$ alkene. Typically a $C_{2-4}$ alkenylene group is a $C_{2-3}$ alkenylene group, for example ethenylene, propenylene or butenylene.

As used herein, a $C_{2-4}$ alkynyl group is a linear or branched alkynyl group containing from 2 to 4 carbon atoms and having one or more, e.g. one or two, typically one triple bonds. Typically a $C_{2-4}$ alkenyl group is a $C_{2-3}$ alkenyl group, for example ethynyl, propynyl or butynyl. A $C_{2-4}$ alkynylene group is an unsubstituted or substituted bidentate moiety obtained by removing two hydrogen atoms from a $C_{2-4}$ alkyne. Typically a $C_{2-4}$ alkynylene group is a $C_{2-3}$ alkynylene group, for example ethynylene, propynylene or butynylene.

An alkyl, alkylene, alkoxy, alkenyl, alkynyl or alkynylene group as used herein may be unsubstituted or substituted. Unless otherwise stated, substituted alkyl, alkylene, alkoxy, alkenyl, alkenylene, alkynyl or alkynylene groups typically carry one or more, e.g. 1, 2, 3 or 4, such as one, two or three e.g. two, or three substituents. Preferred substituents are halogen atoms. Where indicated, an alkyl group may also be substituted with one or two groups $R^2$ as defined herein. The substituents on a substituted alkyl or alkoxy group are typically themselves unsubstituted unless otherwise stated. Where more than one substituent is present, these may be the same or different.

As used herein, a halogen is typically chlorine, fluorine, bromine or iodine and is preferably chlorine, bromine or fluorine, especially chorine or fluorine, and most especially fluorine. Where a group or moiety is substituted with one or more halogen atoms, preferably it carries one, two, three or four halogen atoms, preferably two or three halogen atoms. Where a group or moiety is substituted with two or more halogen atoms, the halogen atoms may be the same or different. Typically, the halogen atoms are the same.

As used herein a 6- to 10-membered aryl group is a substituted or unsubstituted, monocyclic or fused polycyclic aromatic group containing from 6 to 10 carbon atoms in the ring portion. Examples include monocyclic groups such as phenyl and fused bicyclic groups such as naphthyl and indenyl. Phenyl (benzene) is preferred.

As used herein, a 5- to 10-membered heteroaryl group is a substituted or unsubstituted, monocyclic aromatic group containing from 5 to 10 atoms in the ring portion, including at least one heteroatom, for example 1, 2 or 3 heteroatoms, typically selected from O, S and N; and is typically a 5- to 6-membered heteroaryl group which is a substituted or unsubstituted, monocyclic aromatic group containing 5 or 6 atoms in the ring portion, including at least one heteroatom, for example 1, 2 or 3 heteroatoms, typically selected from O, S and N. Examples of 5- and 6-membered heteroaryl groups include pyrrole, furan, thiophene, imidazole, oxazole, thiazole, pyridine, pyridazine, pyrimidine, and pyrazine.

As used herein, a 3- to 10-membered heterocyclyl group is a cyclic group containing from 3 to 10 atoms selected from C, O, N and S in the ring, including at least one heteroatom, and typically one or two heteroatoms; and is typically a 3- to 8-membered heterocyclyl group, typically a 4- to 6-membered heterocyclyl group which is a cyclic group containing from 4 to 6 atoms selected from C, O, N and S in the ring, including at least one heteroatom, and typically one or two heteroatoms. The heteroatom or heteroatoms are typically selected from O, N, and S. A heterocyclic group may be saturated or partially unsaturated. A 4- to 6-membered partially unsaturated heterocyclic group is a cyclic group containing from 4 to 6 atoms selected from C, O, N and S in the ring and containing 1 or 2, e.g. 1 double bond.

A 3- to 10-membered carbocyclyl group is a cyclic hydrocarbon containing from 3 to 10 carbon atoms. A carbocyclyl group may be saturated or partially unsaturated, but is typically saturated. A 3- to 10-membered partially unsaturated carbocyclyl group is a cyclic hydrocarbon containing from 3 to 10 carbon atoms and containing 1 or 2, e.g. 1 double bond. A 3- to 10-membered carbocyclyl group is typically a 4- to 10-membered carbocyclyl group e.g. 3- to 8-membered carbocyclyl group such as a 3- to 6-, 4- to 6-membered or 5- to 6-membered carbocyclic group. Examples of 3- to 6-membered saturated carbocyclic groups include cyclopropyl, cyclobutyl, cyclopentyl and cyclohexyl groups.

Examples of 4- to 6-membered saturated heterocyclic groups include oxetane, azetidine, piperazine, piperidine, morpholine, pyrrolidine, imidazolidine, and oxazolidine. Examples of 4- to 6-membered partially unsaturated heterocyclic groups include tetrahydropyrazine, tetrahydropyridine, dihydro-1,4-oxazine, tetrahydropyrimidine, dihydro-1,3-oxazine, dihydropyrrole, dihydroimidazole and dihydrooxazole.

An aryl, heterocyclyl or heteroaryl group may be unsubstituted or substituted as described herein. For example, an aryl, heterocyclyl or heteroaryl group may be unsubstituted or substituted with 1, 2 or 3, typically 1 or 2 such as e.g. 1 substituent. Suitable substituents include halogen, OH, C(O) $C_{1-4}$ alkyl, C(O)OH, C(O)O$C_{1-4}$ alkyl, $C_{1-4}$ alkyl and $C_{1-4}$ alkoxy, wherein the $C_{1-4}$ alkyl and $C_{1-4}$ alkoxy groups and moieties are themselves unsubstituted or substituted with one or more halogen atoms.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as oxalic, citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkaline earth metal (e.g. calcium or magnesium) hydroxides and organic bases such as alkyl amines, aralkyl amines and heterocyclic amines. Preferred pharmaceutically acceptable salts are salts formed at the $SO_3H$ group with pharmaceutically acceptable bases, in particular quaternary ammonium salts e.g. tetrabutylammonium salts, or alkali metal salts, e.g. sodium or potassium salts, most preferably sodium salts.

In Formula (I), the bicyclic ring adopts the stereochemistry depicted. Thus, when the bicyclic ring is depicted in "chair" form (as below), the R group is in the axial "up" position or the equatorial "down" position, whilst the second ring carrying the OSO$_3$H substituent is in the axial "down" position.

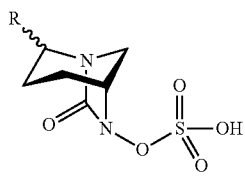

In Formula (II), the bicyclic ring adopts the stereochemistry depicted. Thus, when the bicyclic ring is depicted in "chair" form (as below), the R group is in the axial "up" position, whilst the second ring carrying the OSO$_3$H substituent is in the axial "down" position.

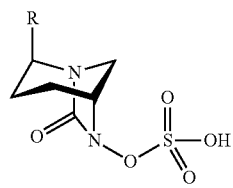

In Formula (III), the bicyclic ring adopts the stereochemistry depicted. Thus, when the bicyclic ring is depicted in "chair" form (as below), the R group is in the equatorial "down" position, whilst the second ring carrying the OSO$_3$H substituent is in the axial "down" position.

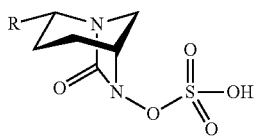

Typically, a compound or composition described herein contains at least 50%, preferably at least 60%, 75%, 90% or 95% of a compound of Formula (I) having the stereochemistry in the bicyclic ring (i.e. at the two chiral centres on the bicyclic ring) as depicted above. Preferably, the compound is substantially diastereomerically pure at the two chiral centres depicted above.

Typically, when a compound or composition described herein comprises a compound of Formula (II), at least 50%, preferably at least 60%, 75%, 90% or 95% of said compound has the stereochemistry in the bicyclic ring (i.e. at the two chiral centres on the bicyclic ring) as depicted above. Preferably, the compound is substantially diastereomerically pure at the two chiral centres depicted above.

Typically, when a compound or composition described herein comprises a compound of Formula (III), at least 50%, preferably at least 60%, 75%, 90% or 95% of said compound has the stereochemistry in the bicyclic ring (i.e. at the two chiral centres on the bicyclic ring) as depicted above.

Preferably, the compound is substantially diastereomerically pure at the two chiral centres depicted above.

In Formula (I), (II) or (III), one or more further chiral centres may be present in the R group. At these chiral centres, the stereochemistry is not limited and the compounds may be used in diastereomerically pure form, or as a mixture of isomers. Typically, a compound or composition described herein contains at least 50%, preferably at least 60, 75%, 90% or 95% of a compound according to Formula (I), (II) or (III) which is diasteriomerically pure with regard to a chiral centre in the R group. Typically, a compound or composition of the invention comprises by weight at least 60%, such as at least 75%, 90%, or 95% of a single diastereomer. Preferably, the compound is substantially optically pure.

Typically, a compound of Formula (I) is a compound of Formula (II).

Further, for the avoidance of doubt, the compounds of the invention may be used in any tautomeric form.

As used herein, "removing or reducing resistance" to antibiotics, or "removing or reducing resistance" in bacteria, means that the bacterial resistance mechanism, e.g. the breakdown of an antibiotic compound by SBL, is prevented or inhibited. Therefore the effects of bacterial resistance (i.e. inefficacy of antibiotics) is removed or reduced. In other words, the compounds of the invention are useful in inhibiting or preventing hydrolysis of a β-lactam ring, i.e. in inhibiting or preventing hydrolysis of an antibiotic compound. They therefore improve the efficacy of antibiotics when used to treat infection caused by SBL-producing bacteria.

Compounds of the Invention

In some preferred compounds of Formula (I), R is halogen. Preferably, when R is halogen, R is fluorine or chlorine. Most preferably, when R is halogen, R is fluorine.

When R is halogen, the compound of Formula (I) may be a compound of Formula (II) or a pharmaceutically acceptable salt thereof or a compound of Formula (III) or a pharmaceutically acceptable salt thereof.

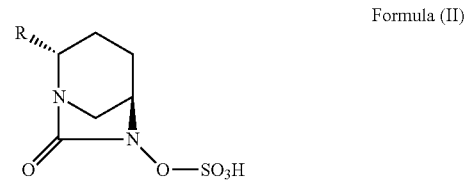

Formula (II)

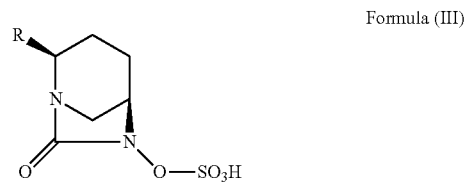

Formula (III)

wherein R is halogen.

Preferably, when R is halogen, the compound of Formula (I) is a compound of Formula (II) or a pharmaceutically acceptable salt thereof.

Preferably, therefore, the compound is a compound of Formula (II) or a pharmaceutically acceptable salt thereof or a compound of Formula (III) or a pharmaceutically acceptable salt thereof and R is fluorine or chlorine. More preferably, the compound is a compound of Formula (II) or a pharmaceutically acceptable salt thereof and R is fluorine or chlorine.

Most preferably, the compound is a compound of Formula (II) or a pharmaceutically acceptable salt thereof and R is fluorine.

Preferably, in the invention, the compound of Formula (I) is a compound of Formula (II) or a pharmaceutically acceptable salt thereof.

In other preferred compounds, the compound of Formula (I) is a compound of Formula (II) or a pharmaceutically acceptable salt thereof; wherein
- R is selected from $C(O)R^1$, $C_{1-4}$ alkyl and L-X—$R^1$, wherein the $C_{1-4}$ alkyl group is substituted with at least one halogen atom and is optionally further substituted with one or two substituents $R^2$;
- $R^1$ is $C_{1-4}$ alkyl which is substituted with at least one halogen atom and is optionally further substituted with one or two substituents $R^2$;
- each $R^2$ is independently selected from OH; $C_{1-4}$ alkoxy which is unsubstituted or substituted with one or more halogen atoms; $C(O)R^3$; C(O)OH; $C(O)OR^3$; 6- to 10-membered aryl; 5- to 6-membered heteroaryl; and 4- to 6-membered heterocyclyl; wherein the aryl, heteroaryl and heterocyclyl groups are unsubstituted or substituted with one, two or three substituents selected from halogen, OH, $C(O)R^3$, C(O)OH, $C(O)OR^3$ and $C_{1-4}$ alkyl and $C_{1-4}$ alkoxy groups which are themselves unsubstituted or substituted with one or more halogen atoms;
- $R^3$ is $C_{1-4}$ alkyl which is unsubstituted or substituted with one or more halogen atoms;
- L is a bond or is a $C_{1-2}$ alkylene group which is unsubstituted or is substituted with at least one halogen atom; and
- X is O or S(O)$_z$ wherein z is 0, 1 or 2.

When R is L-X—$R^1$, L is preferably a bond or an unsubstituted $C_{1-2}$ alkylene group. More preferably, L is a bond or is an unsubstituted $C_1$ alkylene (methylene) group. X is selected from O and S(O)$_z$ wherein z is 0, 1 or 2; i.e. X is selected from O, S, S(O), and S(O)$_2$. Preferably X is selected from O and S.

Preferred L-X—$R^1$ groups include —CH$_2$—O—$R^1$, —S—$R^1$, and —SO$_2$—$R^1$ wherein $R^1$ is as defined herein. More preferred L-X—$R^1$ groups include —CH$_2$—O—$R^1$ and —S—$R^1$, wherein $R^1$ is as defined herein. For example, in such groups $R^1$ is preferably a $C_1$ or $C_2$ alkyl group, preferably a $C_1$ alkyl group. The $R^1$ group is preferably substituted by 1, 2 or 3 halogen groups, e.g. by three halogen groups; for example the $R^1$ group is preferably CF$_3$. Most preferred L-C—$R^1$ groups thus include -L-X—CF$_3$ groups such as —CH$_2$—O—CF$_3$ and —S—CF$_3$.

In other preferred compounds, the compound of Formula (I) is a compound of Formula (II) or a pharmaceutically acceptable salt thereof; wherein
- R is selected from $C(O)R^1$ and $C_{1-4}$ alkyl, wherein the $C_{1-4}$ alkyl group is substituted with at least one halogen atom and is optionally further substituted with one or two substituents $R^2$;
- $R^1$ is $C_{1-4}$ alkyl which is substituted with at least one halogen atom and is optionally further substituted with one or two substituents $R^2$;
- each $R^2$ is independently selected from OH; $C_{1-4}$ alkoxy which is unsubstituted or substituted with one or more halogen atoms; $C(O)R^3$; C(O)OH; $C(O)OR^3$; 6- to 10-membered aryl; 5- to 6-membered heteroaryl; and 4- to 6-membered heterocyclyl; wherein the aryl, heteroaryl and heterocyclyl groups are unsubstituted or substituted with one, two or three substituents selected from halogen, OH, $C(O)R^3$, C(O)OH, $C(O)OR^3$ and $C_{1-4}$ alkyl and $C_{1-4}$ alkoxy groups which are themselves unsubstituted or substituted with one or more halogen atoms;
- $R^3$ is $C_{1-4}$ alkyl which is unsubstituted or substituted with one or more halogen atoms.

Preferably, R is $C_{1-4}$ alkyl, wherein the $C_{1-4}$ alkyl group R is as defined herein.

Typically, in such compounds, R is selected from $C(O)R^1$ and $C_{1-4}$ alkyl, wherein the $C_{1-4}$ alkyl group is substituted with at least one halogen atom (e.g. fluorine or chlorine) and is optionally further substituted with one substituent $R^2$. Preferably, R is selected from $C(O)R^1$ and $C_{1-2}$ alkyl, wherein the $C_{1-2}$ alkyl group is substituted with at least one halogen atom (e.g. fluorine or chlorine) and is optionally further substituted with one substituent $R^2$.

In one preferred aspect of the invention, the compound is a compound of Formula (II) or a pharmaceutically acceptable salt thereof and R is $C_{1-4}$ alkyl, wherein the $C_{1-4}$ alkyl group is substituted with at least one halogen atom (e.g. fluorine or chlorine) and is optionally further substituted with one or two, e.g. one, substituent $R^2$. Preferably, the alkyl group is substituted with at least two, e.g. two or three, halogen atoms. The halogen atoms are preferably selected from fluorine and chlorine. Preferably, R is $C_{1-2}$ alkyl, wherein the $C_{1-2}$ alkyl group is substituted with at least one halogen atom (e.g. fluorine or chlorine) and is optionally further substituted with one substituent $R^2$. More preferably, R is $C_{1-2}$ alkyl, wherein the $C_{1-2}$ alkyl group is substituted with at least two halogen atoms selected from fluorine and chlorine. Most preferably R is a methyl group which is substituted with two or three halogen atoms selected from fluorine and chlorine, e.g. CF$_3$, CCl$_3$, CHF$_2$ and CHCl$_2$.

Where R represents $C(O)R^1$, typically $R^1$ is $C_{1-4}$ alkyl which is substituted with at least one halogen atom (e.g. fluorine or chlorine) and is optionally further substituted with one substituent selected from OH and $C_{1-4}$ alkoxy which is itself unsubstituted or substituted with one or more halogen atoms (e.g. fluorine or chlorine). Preferably, $R^1$ is $C_{1-4}$ alkyl which is substituted with at least one, more preferably at least two (e.g. two or three), halogen atoms. The halogen atoms are preferably selected from fluorine and chlorine.

More preferably $R^1$ is $C_{1-2}$ alkyl, wherein the $C_{1-2}$ alkyl group is substituted with at least two halogen atoms selected from fluorine and chlorine. Most preferably $R^1$ is a methyl group which is substituted with two or three halogen atoms selected from fluorine and chlorine, e.g. CF$_3$.

When $R^2$ represents 6- to 10-membered aryl, it is typically phenyl. When $R^2$ represents 5- to 6-membered heteroaryl, it is typically a 5-membered heteroaryl selected from thiazolyl, pyrrolyl, furanyl, thiophenyl, imidazolyl and oxazolyl, preferably thiazolyl. When $R^2$ represents 4- to 6-membered heterocyclyl, it is typically a 4- or 5-membered heterocyclyl group selected from oxetanyl, azetidinyl, tetrahydrofuranyl, pyrrolidinyl and tetrahydrothiophenyl. Preferably it is a 4-membered heterocyclyl group selected from oxetanyl and azetidinyl, most preferably oxetanyl.

When $R^2$ represents an aryl, heteroaryl or heterocyclyl group, it is unsubstituted or substituted with one, two or three (e.g. one or two) substituents selected from halogen, OH, $C(O)R^3$, C(O)OH, $C(O)OR^3$ and $C_{1-4}$ alkyl and $C_{1-4}$ alkoxy groups which are themselves unsubstituted or substituted with one or more halogen atoms. Preferred substituents are halogen; OH; and $C_{1-2}$ alkyl and $C_{1-2}$ alkoxy groups which are themselves unsubstituted or substituted with one or more halogen atoms. More preferred substituents are halogen, OH, Me and OMe. Most preferably when $R^2$ represents an aryl, heteroaryl or heterocyclyl group, it is unsubstituted.

Each $R^2$ is typically independently selected from OH; $C_{1-2}$ alkoxy which is itself unsubstituted or substituted with one or more halogen atoms; $C(O)OR^3$, wherein $R^3$ is unsubstituted $C_{1-2}$ alkyl; and unsubstituted 5- to 6-membered heteroaryl. Preferably each $R^2$ is independently selected from OH; OMe; C(O)OMe; and unsubstituted thiazolyl.

$R^3$ is typically unsubstituted $C_{1-2}$ alkyl, preferably methyl.

In some preferred compounds of the invention, the compound is a compound of Formula (II) or a pharmaceutically acceptable salt thereof, and R is $C_{1-4}$ alkyl, wherein the $C_{1-4}$ alkyl group is substituted with at least one halogen atom and is optionally further substituted with one or two substituents $R^2$; wherein preferably R is $C_{1-2}$ alkyl, wherein the $C_{1-2}$ alkyl group is substituted with at least one halogen atom (e.g. fluorine or chlorine) and is optionally further substituted with one substituent $R^2$;

each $R^2$ is independently selected from OH; $C_{1-4}$ alkoxy which is unsubstituted or substituted with one or more halogen atoms; $C(O)R^3$; C(O)OH; $C(O)OR^3$; 6- to 10-membered aryl; 5- to 6-membered heteroaryl; and 4- to 6-membered heterocyclyl; wherein the aryl, heteroaryl and heterocyclyl groups are unsubstituted or substituted with one, two or three substituents selected from halogen, OH, $C(O)R^3$, C(O)OH, $C(O)OR^3$ and $C_{1-4}$ alkyl and $C_{1-4}$ alkoxy groups which are themselves unsubstituted or substituted with one or more halogen atoms; wherein preferably each $R^2$ is selected from OH; $C_{1-2}$ alkoxy which is itself unsubstituted or substituted with one or more halogen atoms; $C(O)OR^3$ and unsubstituted 5- to 6-membered heteroaryl; and $R^3$ is $C_{1-4}$ alkyl which is unsubstituted or substituted with one or more halogen atoms; preferably $R^3$ is unsubstituted $C_{1-2}$ alkyl.

Further preferred compounds of the invention are those wherein the compound is a compound of Formula (II) or a pharmaceutically acceptable salt thereof, and wherein:

R is selected from $C(O)R^1$ and $C_{1-4}$ alkyl, wherein the $C_{1-4}$ alkyl group is substituted with at least one halogen atom (e.g. fluorine or chlorine) and is optionally further substituted with one substituent $R^2$;

$R^1$ is $C_{1-4}$ alkyl which is substituted with at least one halogen atom (e.g. fluorine or chlorine) and is optionally further substituted with one substituent selected from OH and $C_{1-4}$ alkoxy which is itself unsubstituted or substituted with one or more halogen atoms (e.g. fluorine or chlorine); and $R^2$ is selected from OH; $C_{1-2}$ alkoxy which is itself unsubstituted or substituted with one or more halogen atoms; $C(O)OR^3$, wherein $R^3$ is unsubstituted $C_{1-2}$ alkyl; and unsubstituted 5- to 6-membered heteroaryl.

More preferred compounds of the invention are those wherein the compound is a compound of Formula (II) or a pharmaceutically acceptable salt thereof, and wherein:

R is selected from $C(O)R^1$ and $C_{1-4}$ alkyl, in particular $C_{1-2}$ alkyl, wherein the alkyl group is substituted with at least one halogen atom (e.g. fluorine or chlorine) and is optionally further substituted with one substituent $R^2$;

$R^1$ is $C_{1-2}$ alkyl, wherein the $C_{1-2}$ alkyl group is substituted with at least two halogen atoms selected from fluorine and chlorine; and $R^2$ is selected from OH; OMe; C(O)OMe; and unsubstituted thiazolyl.

Still more preferred compounds of the invention are those wherein the compound is a compound of Formula (II) or a pharmaceutically acceptable salt thereof, and wherein R is $COCF_3$ or $C_{1-2}$ alkyl, wherein the $C_{1-2}$ alkyl group is substituted with at least one halogen atom (e.g. fluorine or chlorine) and is optionally further substituted with one substituent $R^2$, wherein $R^2$ is selected from OH; OMe; C(O)OMe; and unsubstituted thiazolyl. More preferably, R is $C_{1-2}$ alkyl, wherein the $C_{1-2}$ alkyl group is substituted with at least two halogen atoms selected from fluorine or chlorine. Most preferably R is a methyl group which is substituted with two or three halogen atoms selected from fluorine and chlorine, e.g. $CF_3$, $CCl_3$, $CHF_2$ and $CHCl_2$.

Preferred examples of R groups include $CF_3$, $CHF_2$, $CHCl_2$, $CCl_3$, $CH_2F$, $CF_2CH_3$, $CF_2CH_2CO_2Me$, $COCF_3$, $CF_2$-thiazolyl, $CF_2CH_2OCH_3$, $CF_2CH_2CH_2OH$, CH(OH)$CF_3$, $CH_2CF_3$, $CF_2$-oxetanyl, in particular $CF_3$, $CHF_2$ and $CHCl_2$.

Preferred compounds of the invention include:
(2S, 5R)-7-oxo-2-(trifluoromethyl)-1,6-diazabicyclo[3.2.1]octan-6-yl hydrogen sulfate;
(2S, 5R)-7-oxo-2-(difluoromethyl)-1,6-diazabicyclo[3.2.1]octan-6-yl hydrogen sulfate;
(2S,5R)-2-(dichloromethyl)-7-oxo-1,6-diazabicyclo[3.2.1]octan-6-yl hydrogen sulfate;
(2S, 5R)-7-oxo-2-(trichloromethyl)-1,6-diazabicyclo[3.2.1]octan-6-yl hydrogen sulfate;
(2S, 5R)-2-(fluoromethyl)-7-oxo-1,6-diazabicyclo[3.2.1]octan-6-yl hydrogen sulfate;
(2S, 5R)-7-oxo-2-(trichloromethyl)-1,6-diazabicyclo[3.2.1]octan-6-yl hydrogen sulfate;
(2S, 5R)-2-(1,1-difluoroethyl)-7-oxo-1,6-diazabicyclo[3.2.1]octan-6-yl hydrogen sulfate;
Methyl 3,3-difluoro-3-((2S, 5R)-7-oxo-6-(sulfooxy)-1,6-diazabicyclo[3.2.1]octan-2-yl)propanoate;
(2S, 5R)-7-oxo-2-(2,2,2-trifluoroacetyl)-1,6-diazabicyclo[3.2.1]octan-6-yl hydrogen sulfate;
(2S, 5R)-2-[difluoro(1,3-thiazol-2-yl)methyl]-7-oxo-1,6-diazabicyclo[3.2.1]octan-6-yl hydrogen sulfate;
(2S, 5R)-2-(1,1-difluoro-2-methoxyethyl)-7-oxo-1,6-diazabicyclo[3.2.1]octan-6-yl hydrogen sulfate;
(2S, 5R)-2-(1,1-difluoro-2-hydroxyethyl)-7-oxo-1,6-diazabicyclo[3.2.1]octan-6-yl hydrogen sulfate;
(2S, 5R)-7-oxo-2-(2,2,2-trifluoro-1-hydroxyethyl)-1,6-diazabicyclo[3.2.1]octan-6-yl hydrogen sulfate;
(2S, 5R)-7-oxo-2-(2,2,2-trifluoroethyl)-1,6-diazabicyclo[3.2.1]octan-6-yl hydrogen sulfate;
(2S, 5R)-2-[difluoro(oxetan-3-yl)methyl]-7-oxo-1,6-diazabicyclo[3.2.1]octan-6-yl hydrogen sulfate;
(2S, 5R)-2-(chloromethyl)-7-oxo-1,6-diazabicyclo[3.2.1]octan-6-yl hydrogen sulfate;
(2R, 5R)-7-oxo-2-[(trifluoromethyl)sulfanyl]-1,6-diazabicyclo[3.2.1]octan-6-yl hydrogen sulfate;
(2S, 5R)-7-oxo-2-[(trifluoromethoxy)methyl]-1,6-diazabicyclo[3.2.1]octan-6-yl hydrogen sulfate;
(2R,5R)-2-fluoro-7-oxo-1,6-diazabicyclo[3.2.1]octan-6-yl hydrogen sulphate;
(2S, 5R)-2-fluoro-7-oxo-1,6-diazabicyclo [3.2.1] octan-6-yl hydrogen sulphate; and
(2R,5R)-2-chloro-7-oxo-1,6-diazabicyclo[3.2.1]octan-6-yl hydrogen sulphate;
and pharmaceutically acceptable salts thereof.

Preferred pharmaceutically acceptable salts of these compounds are salts at the $SO_3H$ group, in particular quaternary ammonium salts, e.g. tetrabutylammonium salts, and alkali metal salts, e.g. sodium and potassium salts. Sodium salts as set out below are most preferred:

Sodium (2S, 5R)-7-oxo-2-(trifluoromethyl)-1,6-diazabicyclo[3.2.1]octan-6-yl sulfate;
Sodium (2S, 5R)-7-oxo-2-(difluoromethyl)-1,6-diazabicyclo[3.2.1]octan-6-yl sulfate;
Sodium (2S,5R)-2-(dichloromethyl)-7-oxo-1,6-diazabicyclo[3.2.1]octan-6-yl sulfate;
Sodium (2S, 5R)-7-oxo-2-(trichloromethyl)-1,6-diazabicyclo[3.2.1]octan-6-yl sulfate;
Sodium (2S, 5R)-2-(fluoromethyl)-7-oxo-1,6-diazabicyclo[3.2.1]octan-6-yl sulfate;
Sodium (2S, 5R)-7-oxo-2-(trichloromethyl)-1,6-diazabicyclo[3.2.1]octan-6-yl sulfate;
Sodium (2S, 5R)-2-(1,1-difluoroethyl)-7-oxo-1,6-diazabicyclo[3.2.1]octan-6-yl sulfate;
Methyl (2S, 5R)-3,3-difluoro-3-(7-oxo-6-{[(sodiooxy)sulfonyl]oxy}-1,6-diazabicyclo[3.2.1]octan-2-yl)propanoate;
Sodium (2S, 5R)-7-oxo-2-(2,2,2-trifluoroacetyl)-1,6-diazabicyclo[3.2.1]octan-6-yl sulfate;
Sodium (2S, 5R)-2-[difluoro(1,3-thiazol-2-yl)methyl]-7-oxo-1,6-diazabicyclo[3.2.1]octan-6-yl sulfate;
Sodium (2S, 5R)-2-(1,1-difluoro-2-methoxyethyl)-7-oxo-1,6-diazabicyclo[3.2.1]octan-6-yl sulfate;
Sodium (2S, 5R)-2-(1,1-difluoro-2-hydroxyethyl)-7-oxo-1,6-diazabicyclo[3.2.1]octan-6-yl sulfate;
Sodium (2S, 5R)-7-oxo-2-(2,2,2-trifluoro-1-hydroxyethyl)-1,6-diazabicyclo[3.2.1]octan-6-yl sulfate;
Sodium (2S, 5R)-7-oxo-2-(2,2,2-trifluoroethyl)-1,6-diazabicyclo[3.2.1]octan-6-yl sulfate;
Sodium (2S, 5R)-2-[difluoro(oxetan-3-yl)methyl]-7-oxo-1,6-diazabicyclo[3.2.1]octan-6-yl sulfate;
Sodium (2S, 5R)-2-(chloromethyl)-7-oxo-1,6-diazabicyclo[3.2.1]octan-6-yl sulfate;
Sodium (2R, 5R)-7-oxo-2-[(trifluoromethyl)sulfanyl]-1,6-diazabicyclo[3.2.1]octan-6-yl sulfate;
Sodium (2S, 5R)-7-oxo-2-[(trifluoromethoxy)methyl]-1,6-diazabicyclo[3.2.1]octan-6-yl sulfate;
Sodium (2R,5R)-2-fluoro-7-oxo-1,6-diazabicyclo[3.2.1]octan-6-yl sulphate;
Sodium (2S, 5R)-2-fluoro-7-oxo-1,6-diazabicyclo [3.2.1] octan-6-yl sulphate; and
Sodium (2R,5R)-2-chloro-7-oxo-1,6-diazabicyclo[3.2.1]octan-6-yl sulphate.

More preferred compounds are:
(2S, 5R)-7-oxo-2-(trifluoromethyl)-1,6-diazabicyclo[3.2.1] octan-6-yl hydrogen sulfate;
(2S, 5R)-7-oxo-2-(difluoromethyl)-1,6-diazabicyclo[3.2.1] octan-6-yl hydrogen sulfate;
(2S,5R)-2-(dichloromethyl)-7-oxo-1,6-diazabicyclo[3.2.1] octan-6-yl hydrogen sulfate;
(2S, 5R)-2-(fluoromethyl)-7-oxo-1,6-diazabicyclo[3.2.1]octan-6-yl hydrogen sulfate;
(2S, 5R)-2-(1,1-difluoroethyl)-7-oxo-1,6-diazabicyclo[3.2.1]octan-6-yl hydrogen sulfate;
(2S, 5R)-2-[difluoro(1,3-thiazol-2-yl)methyl]-7-oxo-1,6-diazabicyclo[3.2.1]octan-6-yl hydrogen sulfate;
(2S, 5R)-2-(chloromethyl)-7-oxo-1,6-diazabicyclo[3.2.1] octan-6-yl hydrogen sulfate;
(2R, 5R)-7-oxo-2-[(trifluoromethyl)sulfanyl]-1,6-diazabicyclo[3.2.1]octan-6-yl hydrogen sulfate;
(2S, 5R)-7-oxo-2-[(trifluoromethoxy)methyl]-1,6-diazabicyclo[3.2.1]octan-6-yl hydrogen sulfate;
(2R,5R)-2-fluoro-7-oxo-1,6-diazabicyclo[3.2.1]octan-6-yl hydrogen sulphate;
(2S, 5R)-2-fluoro-7-oxo-1,6-diazabicyclo [3.2.1] octan-6-yl hydrogen sulphate;
and
(2R,5R)-2-chloro-7-oxo-1,6-diazabicyclo[3.2.1]octan-6-yl hydrogen sulphate;
and pharmaceutically acceptable salts thereof.

Preferred pharmaceutically acceptable salts of these compounds are salts at the SO$_3$H group, in particular quaternary ammonium salts, e.g. tetrabutylammonium salts, and alkali metal salts, e.g. sodium and potassium salts. Sodium salts as set out below are most preferred:
Sodium (2S, 5R)-7-oxo-2-(trifluoromethyl)-1,6-diazabicyclo[3.2.1]octan-6-yl sulfate;
Sodium (2S, 5R)-7-oxo-2-(difluoromethyl)-1,6-diazabicyclo[3.2.1]octan-6-yl sulfate;
Sodium (2S,5R)-2-(dichloromethyl)-7-oxo-1,6-diazabicyclo[3.2.1]octan-6-yl sulfate;
Sodium (2S, 5R)-2-(fluoromethyl)-7-oxo-1,6-diazabicyclo [3.2.1]octan-6-yl sulfate;
Sodium (2S, 5R)-2-(1,1-difluoroethyl)-7-oxo-1,6-diazabicyclo[3.2.1]octan-6-yl sulfate;
Sodium (2S, 5R)-2-[difluoro(1,3-thiazol-2-yl)methyl]-7-oxo-1,6-diazabicyclo[3.2.1]octan-6-yl sulfate;
Sodium (2S, 5R)-2-(chloromethyl)-7-oxo-1,6-diazabicyclo [3.2.1]octan-6-yl sulfate;
Sodium (2R, 5R)-7-oxo-2-[(trifluoromethyl)sulfanyl]-1,6-diazabicyclo[3.2.1]octan-6-yl sulfate;
Sodium (2S, 5R)-7-oxo-2-[(trifluoromethoxy)methyl]-1,6-diazabicyclo[3.2.1]octan-6-yl sulfate;
Sodium (2R,5R)-2-fluoro-7-oxo-1,6-diazabicyclo[3.2.1]octan-6-yl sulphate;
Sodium (2S, 5R)-2-fluoro-7-oxo-1,6-diazabicyclo [3.2.1] octan-6-yl sulphate; and
Sodium (2R,5R)-2-chloro-7-oxo-1,6-diazabicyclo[3.2.1]octan-6-yl sulphate;

Most preferred compounds in which R is not halogen are:
(2S, 5R)-7-oxo-2-(trifluoromethyl)-1,6-diazabicyclo[3.2.1] octan-6-yl hydrogen sulfate;
(2S, 5R)-7-oxo-2-(difluoromethyl)-1,6-diazabicyclo[3.2.1] octan-6-yl hydrogen sulfate; and
(2S,5R)-2-(dichloromethyl)-7-oxo-1,6-diazabicyclo[3.2.1] octan-6-yl hydrogen sulfate;
and pharmaceutically acceptable salts thereof.

Preferred pharmaceutically acceptable salts of these compounds are salts at the SO$_3$H group, in particular quaternary ammonium salts, e.g. tetrabutylammonium salts, and alkali metal salts, e.g. sodium and potassium salts. Sodium salts as set out below are most preferred:
Sodium (2S, 5R)-7-oxo-2-(trifluoromethyl)-1,6-diazabicyclo[3.2.1]octan-6-yl sulfate;
Sodium (2S, 5R)-7-oxo-2-(difluoromethyl)-1,6-diazabicyclo[3.2.1]octan-6-yl sulfate; and
Sodium (2S,5R)-2-(dichloromethyl)-7-oxo-1,6-diazabicyclo[3.2.1]octan-6-yl sulfate.

Most preferred compounds in which R is halogen are:
(2R,5R)-2-fluoro-7-oxo-1,6-diazabicyclo[3.2.1]octan-6-yl hydrogen sulphate;
(2S, 5R)-2-fluoro-7-oxo-1,6-diazabicyclo [3.2.1] octan-6-yl hydrogen sulphate;
(2R,5R)-2-chloro-7-oxo-1,6-diazabicyclo[3.2.1]octan-6-yl hydrogen sulphate;
and pharmaceutically acceptable salts thereof.

Preferred pharmaceutically acceptable salts of these compounds are salts at the SO$_3$H group, in particular quaternary ammonium salts, e.g. tetrabutylammonium salts, and alkali metal salts, e.g. sodium and potassium salts. Sodium salts as set out below are most preferred:
Sodium (2R,5R)-2-fluoro-7-oxo-1,6-diazabicyclo[3.2.1]octan-6-yl sulphate;

Sodium (2S, 5R)-2-fluoro-7-oxo-1,6-diazabicyclo [3.2.1] octan-6-yl sulphate;

Sodium (2R,5R)-2-chloro-7-oxo-1,6-diazabicyclo[3.2.1]octan-6-yl sulphate;

Synthesis

The compounds of the invention (especially compounds of Formula (I), Formula (II) or Formula (III) in which R is not halogen) can be synthesised according to the following Scheme A:

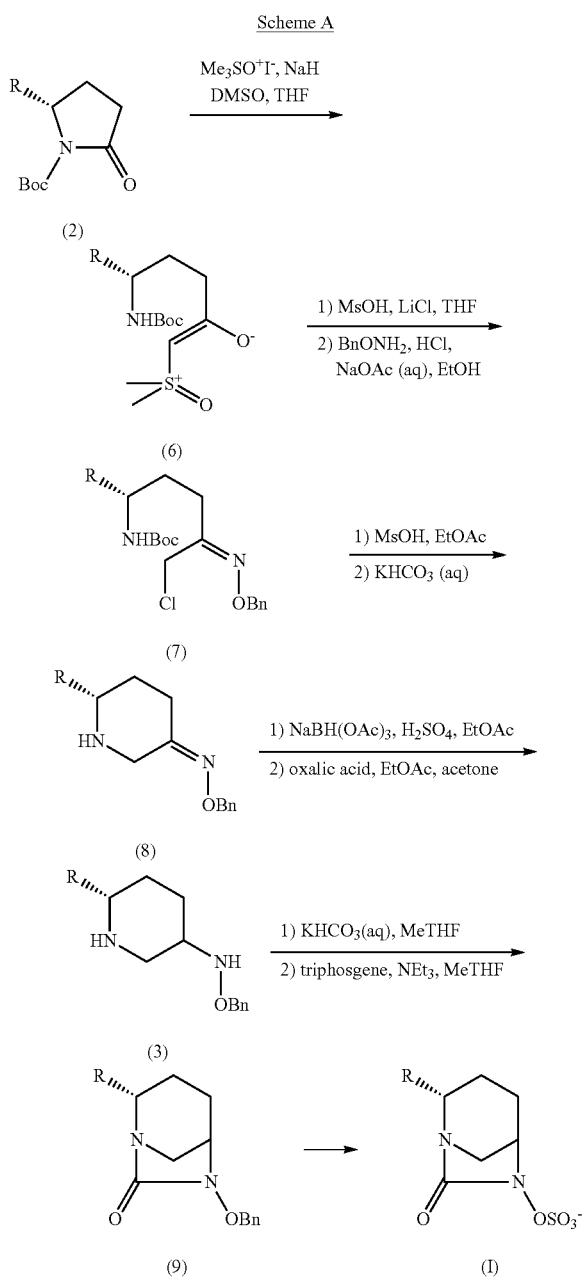

The BOC-pyrrolidinone (2) may be reacted with a sulfoxonium ylid reagent to give in situ the new ring-opened ylid (6). Protonation generates a positively charged sulfoxonium species which is nucleophilically attacked by chloride anion, resulting in loss of DMSO and generating the chloromethyl ketone which condenses with O-benzyl hydroxylamine to give oxime (7). This need not be isolated but may be treated with acid to remove the BOC protecting group and on basification spontaneous cyclisation occurs with formal loss of HCl to give ring expanded (8). Once again this need not be isolated but stereoselective reduction of the oxime double bond followed by salt formation with oxalic acid facilitates isolation of piperidine (3). Cyclisation using triphosgene as a phosgene source generates the bicyclic urea (9) then debenzylation and sulfonation produces the compound of formula (I). The R group may be protected using suitable protecting means, as required. Further details regarding synthetic routes, and alternative synthetic schemes, to provide the compounds of the invention are set out in the general synthetic methodology section below.

Scheme A shows synthetic routes to compounds of the invention of Formula (II). Compounds of the invention of Formula (III) can be made using similar chemistry but starting from the diastereoisomer of (2), ie (2A):

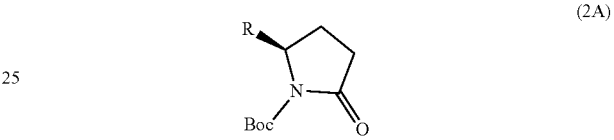

Compounds of Formula (II) and Formula (III) in which R is halogen can be synthesized from the carboxylic acid precursor according to the following Scheme B (shown for compounds of Formula (II):

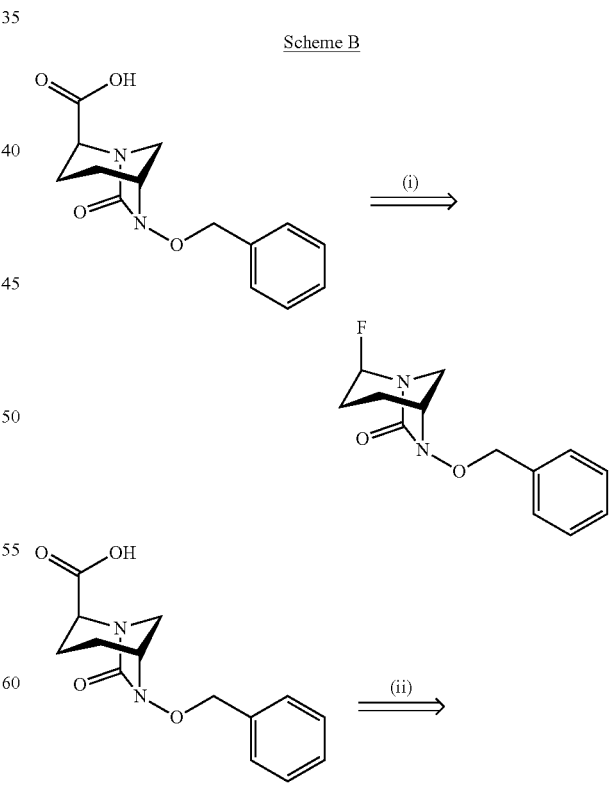

(i) AgF, Selectfluor
(ii) Pb(OAc)4, LiCl

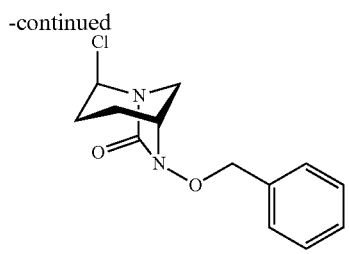

The starting material in Scheme B corresponds to compound (9) in Scheme A and can be synthesized in accordance with Scheme A, starting from a carboxyl-functionalised compound (2). The halo-compounds shown in Scheme B can be converted from the —OBn form to the —OSO$_3$— form via debenzylation and sulfonation as described above and in the Examples. Corresponding compounds of Formula (III) can be prepared starting from the stereoisomer of the starting material.

The inventors developed the chemical route shown in Scheme B to provide the halo-compounds of the invention. Whilst decarboxylative conversion of aryl or alkyl carboxylic acids to the corresponding aryl or alkyl halides has been known for many years (e.g. see Hunsdiecker and Hunsdiecker (1942, Chem. Ber., 75, 291)), it is only in recent years that the original concept of reacting a carboxylic acid with a silver salt and bromine has developed. For example, Li et al (2012, JACS, 134, 10401) reported very mild conditions for conversion of alkyl acids to alkyl fluorides using catalytic silver nitrate and Selectfluor™. Li includes one example of the very rare F—CH2-N—CO functionality, but this is in a special situation where there are two carbonyl groups on the single nitrogen, effectively removing the nitrogen lone pair through extensive delocalisation to the oxygens of the carbonyl groups. There are very few examples of this functionality with only one carbonyl group on the nitrogen, and even they are restricted to reactive intermediates for glycosylation-type reactions, proceeding via iminium formation followed by quenching of the iminium ion with alcohol (2016, Organic Letters, 18, 9890). The inventors have found that the propensity of a molecule to fragment and decompose can be overcome by organising the functionality such that stereochemical control can overcome the natural tendency for reactivity. In the case of the stability of compounds of the invention, stabilisation can be introduced by the decomposition pathway via the iminium species going via a "bridgehead double bond". The impossibility of forming a bridgehead double bond was first observed by Bredt (1902, "Ueber isomere Dehydrocamphersäuren, Lauronolsäuren und Bihydrolauro-Lactone", Ber. Deutsch. Chem. Ges., 35, 1286-1292) and later rationalised using molecular orbital theory which requires good spatial overlap of p-orbitals in order to form a double bond. Such a situation exists with the halogenated compounds of the invention. The chloro substituent is similarly prepared by a decarboxylative halogenation using the standard Kochi reaction conditions of lead tetraacetate and lithium chloride (J. K. Kochi, 1965, JACS, 87, 2500).

Compositions and Combinations

The compounds of the invention may be provided in a pharmaceutical composition, the pharmaceutical composition comprising a compound of the invention together with a pharmaceutically acceptable carrier or diluent. Typically, the composition contains up to 85 wt % of a compound of the invention. More typically, it contains up to 50 wt % of a compound of the invention. Preferred pharmaceutical compositions are sterile and pyrogen free. Further, when the pharmaceutical compositions provided by the invention contain a compound of the invention which is optically active, the compound of the invention is typically a substantially pure optical isomer.

As explained above, the compounds of the invention are useful in treating or preventing bacterial infection. In particular, they are inhibitors of SBL enzymes and are therefore useful for removing or reducing resistance of Gram-negative bacteria to antibiotics. The compounds may be used alone or they may be used in combination therapies with antibiotic agents, to enhance the action of the antibiotic agent. The compounds may also be used in combination with MBL inhibitors, in particular where the bacteria causing the infection are resistant to treatment by an antibiotic agent alone and the resistance is, or is suspected of being, caused at least in part by metallo-β-lactamase enzymes.

The present invention therefore also provides a combination of (i) a compound of the invention; and one or more of (ii) a metallo-β-lactamase (MBL) inhibitor; and (iii) an antibiotic agent. The combinations may also comprise further active agents if desired.

In the combinations of the invention, the active agents may each be provided in a single formulation or one or more of them may be separately formulated. Where separately formulated, the two or more agents may be administered simultaneously or separately. Active agents which are separately formulated may be provided in the form of a kit, optionally together with instructions for their administration. For example, the kit may comprise (i) a composition comprising a compound of the invention; and one or both of (ii) a composition comprising an antibiotic agent and (iii) a composition comprising an MBL inhibitor, optionally together with instructions for their use. Where two or more active agents are formulated together, the two or more active agents may be provided as a pharmaceutical composition. The pharmaceutical composition may therefore comprise (i) a compound of the invention as described herein; (ii) a pharmaceutically acceptable carrier or diluent; and optionally one or both of (iii) an antibiotic agent; and (iv) a metallo-β-lactamase (MBL) inhibitor.

Thus, the compound of the invention and the antibiotic agent may be formulated together or separately. Further, the compound of the invention and the MBL inhibitor may be formulated together or separately. Where all three active agents are present, the compound of the invention, the MBL inhibitor and the antibiotic agent may each be provided in a single formulation, or they may be separately formulated. Alternatively, two of the components may be provided in a single formulation and the remaining component may be provided separately. In other words, the compound of the invention may be formulated with the MBL inhibitor and the antibiotic agent; or the compound of the invention may be formulated with the MBL inhibitor whilst the antibiotic agent is provided separately; or the compound of the invention may be formulated with the antibiotic agent whilst the MBL inhibitor is provided separately; or the MBL inhibitor may be formulated with the antibiotic agent whilst the compound of the invention is provided separately; or the compound of the invention, the MBL inhibitor and the antibiotic agent may each be formulated separately.

Preferably, the antibiotic agent which is administered with the compound of the invention, or used in the combinations or compositions of the invention, is a β-lactam antibiotic. More preferably, the antibiotic agent is a β-lactam antibiotic selected from carbapenems, penicillins, cephalosporins and penems; or the antibiotic agent is aztreonam. Examples of carbapenem antibiotics include Benapenem, Imipenem, Meropenem, Ertapenem, Doripenem and Biapenem. Examples of penicillins include Amoxicillin, Ampicillin, Ticarcillin, Piperacillin and Cloxacillin. Examples of cephalosporins include Cefepime, Cefazolin, Ceftriaxone, Ceftazidine and Ceftobiprole. Examples of penems include Faropenem. Other antibiotic agents include tobramycin, neomycin, streptomycin, gentamycin, tazobactam, rifampicin, ciprofloxacin, amikacin, colistin, aztreonam and levofloxacin. Preferably, the β-lactam antibiotic is aztreonam or a carbapenem antibiotic, more preferably biapenem, imipenem or meropenem. In one aspect, biapenem is a preferred carbapenem antibiotic. In another aspect, meropenem is a preferred carbapenem antibiotic. In another preferred aspect, the β-lactam antibiotic is a carbapenem antibiotic, more preferably imipenem or meropenem, most preferably meropenem.

Where an MBL inhibitor is present in the combinations or compositions of the invention, or is administered with a compound of the invention, the MBL inhibitor is preferably a compound as described in WO 2014/198849, GB2533136, PCT/EP2018/069827 (published as WO 2019/016393) or EP18290056.3.

Preferably, the MBL inhibitor is a compound of Formula (A), or a pharmaceutically acceptable salt thereof,

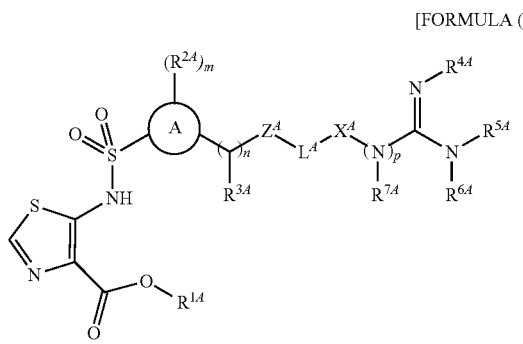

[FORMULA (A)]

wherein
$R^{1A}$ is selected from H, $R^{1b}$ and —CH$_2$OC(O)R$^{1b}$, wherein $R^{1b}$ is selected from an unsubstituted $C_1$ to $C_4$ alkyl group and phenyl;

(A) is a cyclic group selected from $C_6$ to $C_{10}$ aryl, 5- to 10-membered heteroaryl, and 4- to 10-membered carbocyclic and heterocyclic groups;

each $R^{2A}$ is independently selected from:
(i) halo or $R^8$;
(ii) $C_{1-3}$ alkyl, O($C_{1-3}$ alkyl), S($C_{1-3}$ alkyl), SO($C_{1-3}$ alkyl) or SO$_2$($C_{1-3}$ alkyl), any of which may optionally be substituted with 1, 2 or 3 halo substituents and/or one $R^8$ substituent; and
(iii) NR$^a$C(O)R$^c$, and NR$^a$C(O)NR$^b$R$^c$, wherein each Ra and Rb is independently selected from hydrogen and unsubstituted $C_{1-2}$ alkyl and each R$^c$ is unsubstituted $C_{1-2}$ alkyl;
and
each $R^8$ is independently selected from CN, OH, —C(O)NR$^f$R$^g$, —NR$^f$R$^g$, —NR$^{10}$C(NR$^{11}$)R$^{12}$, —C(NR$^{10}$)NR$^{11}$R$^{12}$, and —NR$^{10}$C(NR$^{11}$I)NR$^{12}$R$^{13}$; wherein each of R$^f$ and R$^g$ is independently H or unsubstituted $C_{1-2}$ alkyl;

m is 0, 1, 2 or 3
$R^{3A}$ is selected from hydrogen and a $C_1$ to $C_3$ alkyl group which is unsubstituted or is substituted with 1, 2 or 3 substituents selected from halogen, —OR$^{10}$, and —NR$^{10}$R$^{11}$;

n is 0 or 1
$Z^A$ is a bond or is selected from —NR$^{10}$C(O)—, —C(O)NR$^{10}$—, —NR$^{10}$C(O)NR$^{11}$—, —NR$^{10}$C(O)O—, —OC(O)NR$^{10}$, —NR$^{10}$C(O)S—, —SC(O)NR$^{10}$, —NR$^{10}$C(NR$^{11}$)—, —C(NR$^{10}$)NR$^{11}$—, —NR$^{10}$C(NR$^{11}$)NR$^{12}$—, —NR$^{10}$C(N$^+$R$^{11}$R$^{12}$)—, —C(N$^+$R$^{10}$R$^{11}$)NR$^{12}$—, —NR$^{10}$C(N$^+$R$^{11}$R$^{12}$)NR$^{13}$—, —NR$^{10}$C(NR$^{11}$)O—, —OC(NR$^{10}$)NR$^{11}$, —NR$^{10}$C(N$^+$R$^{11}$R$^{12}$)O—, —OC(N$^+$R$^{10}$R$^{11}$)NR$^{12}$—, —NR$^{10}$C(NR$^{11}$)S—, —SC(NR$^{10}$)NR$^{11}$, —NR$^{10}$C(N$^+$R$^{11}$R$^{12}$)S—, —SC(N$^+$R$^{10}$R$^{11}$)NR$^{12}$—, —C(O)NR$^{15}$—, —NR$^{10}$C(O)NR$^{15}$—, —OC(O)NR$^{15}$, —SC(O)NR$^{15}$, —C(NR$^{10}$)NR$^{15}$—, —NR$^{10}$C(NR$^{11}$)NR$^{15}$—, —C(N$^+$R$^{10}$R$^{11}$)NR$^{15}$—, —NR$^{10}$C(N$^+$R$^{11}$R$^{12}$)NR$^{15}$—, —OC(NR$^{10}$)NR$^{15}$, —OC(N$^+$R$^{10}$R$^{11}$)NR$^{15}$—, —SC(NR$^{10}$)NR$^{15}$, and —SC(N$^+$R$^{10}$R$^{11}$)NR$^{15}$—.

$L^A$ is a bond or is selected from $C_{1-4}$ alkylene, $C_{2-4}$ alkenylene, $C_{2-4}$ alkynylene, $C_{1-3}$ alkylene-($C_{3-6}$cycloalkylene)-$C_{1-3}$ alkylene, $C_{1-4}$ alkylene-($C_{3-6}$cycloalkylene) and ($C_{3-6}$cycloalkylene)-$C_{1-4}$ alkylene, wherein L is unsubstituted or is substituted with 1 or 2 substituents selected from halogen, —OR$^{10}$, and —NR$^{10}$R$^{11}$; or L is —C(R$^{10}$)=N—;

$X^A$ is a bond or, when L is other than a bond or —C(R$^{10}$)=N—, X is a bond or is selected from —NR$^{10}$—, —O—, —NR$^{10}$C(NR$^{11}$)—, and —C(NR$^{10}$)—;

p is 0 or 1;
$R^{4A}$ is selected from H, —CN and $C_1$ to $C_3$ alkyl which is unsubstituted or is substituted with 1, 2 or 3 substituents selected from halogen, —OR$^{10}$, —NR$^{10}$R$^{11}$, and —CN;
or $R^{4A}$ is joined together with $R^{5A}$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —OR$^{10}$, —NR$^{10}$R$^{11}$, and —CN;
$R^{5A}$ is selected from H, —CN and $C_1$ to $C_3$ alkyl which is unsubstituted or is substituted with 1, 2 or 3 substituents selected from halogen, —OR$^{10}$, —NR$^{10}$R$^{11}$, and —CN;
or $R^{5A}$ is joined together with $R^{4A}$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —OR$^{10}$, —NR$^{10}$R$^{11}$, and —CN;
or $R^{5A}$ is joined together with $R^6$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —OR$^{10}$, —NR$^{10}$R$^{11}$, and —CN;

$R^{6A}$ is selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;

or $R^{6A}$ is joined together with $R^{5A}$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

or $R^{6A}$ is joined together with $R^{7A}$ if present to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

$R^{7A}$ if present is selected from H, —CN and $C_1$ to $C_3$ alkyl which is unsubstituted or is substituted with 1, 2 or 3 substituents selected from halogen, —$OR^{10}$, —$NR^{10}R^{11}$, and —CN;

or $R^{7A}$ is joined together with $R^{6A}$ to form, together with the atoms to which they are attached, a 5- to 6-membered heterocyclic group comprising at least one saturated carbon atom in the ring, said heterocyclic group being unsubstituted or substituted with 1 or 2 substituents selected from unsubstituted $C_1$ to $C_2$ alkyl, halogen, —$OR^{10}$, —$NR^{10}R^{11}$, and —CN;

each $R^{10}$, $R^{11}$, $R^{12}$, $R^{13}$ and $R^{14}$ is independently H or methyl;

each $R^{15}$ is independently substituted $C_1$ to $C_4$ alkyl or unsubstituted $C_2$ to $C_4$ alkyl, wherein when $R^{15}$ is a substituted alkyl group the alkyl group is substituted with 1, 2 or 3 substituents independently selected from halogen, CN, $OR^{10}$ and —$NR^{10}R^{11}$.

More preferably, the MBL inhibitor is a compound of Formula (A), or a pharmaceutically acceptable salt thereof, wherein:

$R^{1A}$ is H;

(A) is selected from phenyl, cyclohexane, piperidine, pyridazine, pyridine and thiazole;

m is 1 or 2;

each $R^{2A}$ is independently selected from:
halo, CN, OH, —$C(O)NR^fR^g$, —$NR^fR^g$; wherein each of $R^f$ and $R^g$ is independently H or methyl; and
$C_{1-2}$ alkyl, $O(C_{1-2}$ alkyl), $S(C_{1-2}$ alkyl), $SO(C_{1-2}$ alkyl) any of which may optionally be substituted with 1, 2 or 3 substituents selected from halo, CN, OH;

n is 0;

$Z^A$ is selected from —$NR^{10}C(O)$—, —$C(O)NR^{10}$—, and —$NR^{10}C(O)NR^{11}$—;

$L^A$ is a bond or is selected from $C_{1-3}$ alkylene and $C_{2-3}$ alkenylene.

$X^A$ is a bond;

p is 0; or p is 1 and $R^{7A}$ is H;

$R^{4A}$ is H;

$R^{5A}$ is selected from H, —CN and $C_1$ to $C_2$ alkyl which is unsubstituted or is substituted with 1, 2 or 3 halo substituents and/or one —$NR^{10}R^{11}$ substituent H; and $R^{6A}$ is H.

Still more preferably, the MBL inhibitor is a compound of Formula (A) selected from:

5-[[4-[(2-guanidinoacetyl)amino]-3-(trifluoromethoxy)phenyl]sulfonylamino]thiazole-4-carboxylic acid;

5-[[3-fluoro-4-[[(2-guanidinoacetyl)amino]methyl]phenyl]sulfonylamino]thiazole-4-carboxylic acid;

5-[[3-fluoro-4-(guanidinomethyl)phenyl]sulfonylamino]thiazole-4-carboxylic acid;

5-[[3-fluoro-4-(2-guanidinoethylsulfanylcarbonylamino)phenyl]sulfonylamino]thiazole-4-carboxylic acid;

5-[[4-[2-[(2-amino-2-imino-ethyl)amino]-2-oxo-ethyl]-3-fluoro-phenyl]sulfonylamino]thiazole-4-carboxylic acid;

5-[[3-carbamoyl-4-[(2-guanidinoacetyl)amino]phenyl]sulfonylamino]thiazole-4-carboxylic acid;

5-[[3-cyano-4-[(2-guanidinoacetyl)amino]phenyl]sulfonylamino]thiazole-4-carboxylic acid;

5-[[3-fluoro-4-(2-guanidinoethoxycarbonylamino)phenyl]sulfonylamino]thiazole-4-carboxylic acid;

5-[(4-guanidinophenyl)sulfonylamino]thiazole-4-carboxylic acid;

5-[[4-[2-(2-carbamimidoylhydrazino)-2-oxo-ethyl]-3-fluoro-phenyl]sulfonylamino]thiazole-4-carboxylic acid;

5-[[3-chloro-4-[(2-guanidinoacetyl)amino]phenyl]sulfonylamino]thiazole-4-carboxylic acid;

5-[[4-[(2-guanidinoacetyl)amino]-3-methoxy-phenyl]sulfonylamino]thiazole-4-carboxylic acid;

5-[[4-[[2-(2-carbamimidoylhydrazino)acetyl]amino]-3-fluoro-phenyl]sulfonylamino]thiazole-4-carboxylic acid;

5-[[4-[[(2E)-2-(carbamimidoylhydrazono)acetyl]amino]-3-fluoro-phenyl]sulfonylamino]thiazole-4-carboxylic acid;

5-[[4-[[2-(4,5-dihydro-1H-imidazol-2-ylamino)acetyl]amino]-3,5-difluoro-phenyl]sulfonylamino]thiazole-4-carboxylic acid;

5-[[6-[(2-guanidinoacetyl)amino]pyridazin-3-yl]sulfonylamino]thiazole-4-carboxylic acid;

5-[[4-[(2-amino-2-imino-ethyl)carbamoylamino]-3-fluoro-phenyl]sulfonylamino]thiazole-4-carboxylic acid;

5-[[3,5-difluoro-4-(guanidinocarbamoylamino)phenyl]sulfonylamino]thiazole-4-carboxylic acid;

5-[[4-[(3-amino-3-imino-propanoyl)amino]-3,5-difluoro-phenyl]sulfonylamino]thiazole-4-carboxylic acid;

5-[[4-[[3-(dimethylamino)-3-imino-propanoyl]amino]-3-fluoro-phenyl]sulfonylamino]thiazole-4-carboxylic acid;

5-[[3-fluoro-4-[(2-guanidinooxyacetyl)amino]phenyl]sulfonylamino]thiazole-4-carboxylic acid;

5-[[3-fluoro-4-[[3-imino-3-(methylamino)propanoyl]amino]phenyl]sulfonylamino]thiazole-4-carboxylic acid;

5-[[4-[3-(4,5-dihydro-1H-imidazol-2-yl)propanoylamino]-3-fluoro-phenyl]sulfonylamino]thiazole-4-carboxylic acid;

5-[[2-[(2-guanidinoacetyl)amino]thiazol-5-yl]sulfonylamino]thiazole-4-carboxylic acid;

5-[[4-[[2-[(N-cyanocarbamimidoyl)amino]acetyl]amino]-3-fluoro-phenyl]sulfonylamino]thiazole-4-carboxylic acid;

5-[[3-fluoro-4-(guanidinocarbamoylamino)phenyl]sulfonylamino]thiazole-4-carboxylic acid;

5-[[3-fluoro-4-[[2-(morpholine-4-carboximidoylamino)acetyl]amino]phenyl]sulfonylamino]thiazole-4-carboxylic acid;

5-[[4-[(3-amino-3-imino-2-methyl-propanoyl)amino]-3-fluoro-phenyl]sulfonylamino]thiazole-4-carboxylic acid;

5-[[4-[[2-(4,5-dihydro-1H-imidazol-2-yl)acetyl]amino]-3-fluoro-phenyl]sulfonylamino]thiazole-4-carboxylic acid;

5-[[4-(carbamimidoylcarbamoylamino)-3-fluoro-phenyl]sulfonylamino]thiazole-4-carboxylic acid;

5-[[4-[[(2R)-2-guanidinopropanoyl]amino]phenyl]sulfonylamino]thiazole-4-carboxylic acid;

5-[[3,5-difluoro-4-[(2-guanidinoacetyl)amino]phenyl]sulfonylamino]thiazole-4-carboxylic acid;
5-[[4-[(4-amino-4-imino-butanoyl)amino]-3-fluoro-phenyl]sulfonylamino]thiazole-4-carboxylic acid;
5-[[4-[[2-(4,5-dihydro-1H-imidazol-2-ylamino)acetyl]amino]-2,5-difluoro-phenyl]sulfonylamino]thiazole-4-carboxylic acid;
5-[[2,5-difluoro-4-[(2-guanidinoacetyl)amino]phenyl]sulfonylamino]thiazole-4-carboxylic acid;
5-[[3-fluoro-4-[[2-[(N-methylcarbamimidoyl)amino]acetyl]amino]phenyl]sulfonylamino]thiazole-4-carboxylic acid;
5-[[3-fluoro-4-[[2-(2-iminoimidazolidin-1-yl)acetyl]amino]phenyl]sulfonylamino]thiazole-4-carboxylic acid;
5-[[4-[[2-[carbamimidoyl(methyl)amino]acetyl]amino]-3-fluoro-phenyl]sulfonylamino]thiazole-4-carboxylic acid;
5-[[4-[[2-[[N-(2-aminoethyl)carbamimidoyl]amino]acetyl]amino]-3-fluoro-phenyl]sulfonylamino]thiazole-4-carboxylic acid;
5-[[5-fluoro-6-[(2-guanidinoacetyl)amino]-3-pyridyl]sulfonylamino]thiazole-4-carboxylic acid;
5-[[3-fluoro-4-(3-guanidinopropanoylamino)phenyl]sulfonylamino]thiazole-4-carboxylic acid;
5-[[4-[(3-amino-3-imino-propanoyl)amino]-3-fluoro-phenyl]sulfonylamino]thiazole-4-carboxylic acid;
5-[[3,5-difluoro-4-(guanidinocarbamoylamino)phenyl]sulfonylamino]thiazole-4-carboxylic acid;
5-[[3-fluoro-4-[(2-guanidinoacetyl)amino]phenyl]sulfonylamino]thiazole-4-carboxylic acid; and
5-[[4-[(2-guanidinoacetyl)amino]phenyl]sulfonylamino]thiazole-4-carboxylic acid; and pharmaceutically acceptable salts thereof.

Compounds of Formula (A) and pharmaceutically acceptable salts thereof are described in WO 2019/016393.

Alternatively, the MBL inhibitor may preferably be a compound of Formula (B), or a pharmaceutically acceptable salt thereof,

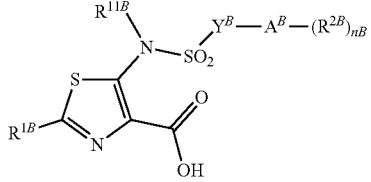

[Formula (B)]

wherein
$R^{1B}$ is hydrogen, halo, CN, $R^{12B}$, $OR^{12B}$, $SR^{12B}$ or $NR^{12B}R^{13B}$;
wherein $R^{12B}$ is $C_{1-6}$ alkyl optionally substituted with one or more substituent $R^{aB}$; phenyl or 5- to 6-membered heteroaryl, either of which may optionally be substituted with one or more substituent $R^{bB}$; or 3- to 6-membered cycloalkyl or 3- to 6-membered heterocyclyl, either of which is optionally substituted with one or more substituent $R^{cB}$;
each $R^{aB}$ is independently halo, CN, OH or $OC_{1-4}$ alkyl optionally substituted by one or more substituent selected from halo and OH;
each $R^{bB}$ is independently halo, CN, OH or $C_{1-4}$ alkyl or $OC_{1-4}$ alkyl either of which may optionally substituted by one or more substituent selected from halo and OH;
each $R^{cB}$ is independently halo, CN, OH, oxo or $C_{1-4}$ alkyl or $OC_{1-4}$ alkyl optionally substituted by one or more substituent selected from halo and OH;
$R^{13B}$ is hydrogen or $C_{1-6}$ alkyl optionally substituted with one or more substituent Ra as defined above;
$Y^B$ is a single bond, $—C_{1-4}$ alkylene- or $—C_{2-4}$ alkenylene-, either of which may be substituted with a group $R^{17B}$; or
$—C_{1-4}$ alkylene-O—; $—C_{1-4}$ alkylene-N($R^{8B}$)—; $—N(R^{8B})—$; $—C_{1-4}$ alkylene-C(O)N($R^{8B}$)—; $—C_{1-4}$ alkylene-N($R^{8B}$)C(O)— or $—N(R^{8B})C_{1-4}$ alkylene-; wherein
$R^{17B}$ is $OR^{1B}$, $NR^{1B}R^{mB}$, $NR^{1B}C(O)R^{mB}$, $C(O)NR^{1B}R^{mB}$, $C(O)OR^{mB}$;
each $R^{1B}$ and $R^{mB}$ is independently H or $C_{1-4}$ alkyl; and
$R^{8B}$ is hydrogen or $C_{1-6}$ alkyl or $—C(O)C_{1-6}$ alkyl either of which is optionally substituted by one or more substituent $R^{dB}$; and
$C_{1-4}$ alkylene chains may optionally be substituted with one or more substituents $R^{eB}$;
each $R^{dB}$ and $R^{eB}$ is independently halo, CN, OH or $OC_{1-4}$ alkyl optionally substituted by one or more substituent selected from halo and OH;
$A^B$ represents a cyclic group selected from a 6- to 10-membered aryl, 5- to 10-membered heteroaryl or a 3- to 10-membered carbocyclyl or heterocyclyl group;
$n^B$ is 0 to 4;
each $R^{2B}$ is independently selected from $R^{3B}$; or
$C_{1-4}$ alkyl, $C_{2-4}$ alkenyl, $O(C_{1-4}$ alkyl), $S(C_{1-4}$ alkyl), $SO(C_{1-4}$ alkyl) or $SO_2(C_{1-4}$ alkyl), any of which may optionally be substituted with one or more substituent $R^{3B}$; or
$C(O)OR^{6B}$; $C(O)R^{6B}$; $OR^{5B}$, $NR^{4B}R^{5B}$; $NR^{4B}C(O)R^{6B}$, $NR^{4B}C(O)NR^{5B}R^{6B}$ or $SO_2NR^{21B}R^{22B}$;
or when $A^B$ is saturated or partially saturated, $R^{2B}$ may also be oxo;
each $R^{3B}$ is independently halo, nitro, CN, OH; or
$—C(O)OR^{14B}$, $—C(O)NR^{14B}R^{15B}$ or $—NR^{14B}R^{15B}$; or
phenyl optionally substituted with one or more substituent $R^{7B}$; or
naphthyl optionally substituted with one or more substituent $R^{7B}$; or
5- to 10-membered heteroaryl optionally substituted with one or more substituent $R^{7B}$; or
3- to 8-membered carbocyclyl optionally substituted with one or more substituent $R^{7B}$; or
3- to 8-membered heterocyclyl optionally substituted with one or more substituent selected from oxo and $R^{7B}$;
each of $R^{14B}$ and $R^{15B}$ is independently H, or $C_{1-6}$ alkyl optionally substituted with one or more substituents selected from halo and OH;
each $R^{7B}$ is independently halo, CN, OH; or $C_{1-4}$ alkyl or $OC_{1-4}$ alkyl either of which may optionally substituted by one or more substituent selected from halo and OH; or $NR^{jB}R^{kB}$, wherein each $R^{jB}$ and $R^{kB}$ is independently H or $C_{1-4}$ alkyl;
each of $R^{21B}$ and $R^{22B}$ is hydrogen or $C_{1-4}$ alkyl or $R^{21B}$ and $R^{22B}$ together with the nitrogen atom to which they are attached may form a 5- or 6-membered heterocyclic ring, optionally containing one further heteroatom selected from N, O and S and optionally substituted with $C_{1-4}$ alkyl or halo;
$R^{4B}$ is hydrogen or $C_{1-6}$ alkyl optionally substituted with halo, CN, OH, $NR^{jB}R^{kB}$; or $OC_{1-4}$ alkyl which may optionally substituted by one or more substituent selected from halo and OH; wherein each $R^{jB}$ and $R^{kB}$ is independently H or $C_{1-4}$ alkyl
$R^{5B}$ is hydrogen, phenyl, 5- to 6-membered heteroaryl, 3- to 8-membered carbocyclyl or 3- to 8-membered heterocyclyl; or C$_{1-6}$ alkyl optionally substituted with phenyl, 5- to 6-membered heteroaryl, 3- to 8-membered carbocyclyl or 3- to 8-membered heterocyclyl;

wherein phenyl and heteroaryl groups are optionally substituted by one or more substituent R$^1$ and carbocyclyl and heterocyclyl groups are optionally substituted by one or more substituent R$^{gB}$ and wherein:

each R$^{fB}$ is independently halo, CN, OH or C$_{1-4}$ alkyl or OC$_{1-4}$ alkyl either of which may optionally be substituted by one or more substituent selected from halo and OH;

each R$^{gB}$ is independently halo, CN, OH, oxo or C$_{1-4}$ alkyl or OC$_{1-4}$ alkyl optionally substituted by one or more substituent selected from halo and OH;

R$^{6B}$ is C$_{1-6}$ alkyl optionally substituted with one or more R$^{hB}$, or phenyl or 5- to 6-membered heteroaryl either of which is optionally substituted with one or more substituent R$^{1B}$;

each R$^{hB}$ is independently halo, CN, OH, NH$_2$, phenyl, pyridyl, COOH or OC$_{1-4}$ alkyl optionally substituted by one or more substituent selected from halo and OH;

each R$^{1B}$ is independently halo, CN, OH, NH$_2$ or C$_{1-4}$ alkyl or OC$_{1-4}$ alkyl either of which may optionally be substituted by one or more substituent selected from halo and OH;

R$^{11B}$ is hydrogen, C$_{1-4}$ alkyl optionally substituted by halo or benzyl optionally substituted by halo.

More preferably, when the MBL inhibitor is a compound of Formula (B), or a pharmaceutically acceptable salt thereof R$^{1B}$ is hydrogen;

Y$^B$ is a single bond or —C$_{1-4}$ alkylene-;

A$^B$ represents a cyclic group selected from phenyl, pyridyl, pyrazolyl, thiophenyl or benzothiophenyl;

n$^B$ is 0 to 3;

each R$^{2B}$ is independently selected from halo, or when A is saturated or partially saturated, oxo; or C$_{1-4}$ alkyl; or NR$^{4B}$R$^{5B}$ wherein R$^{4B}$ is hydrogen or C$_{1-4}$ alkyl and R$^{5B}$ is hydrogen; or NR$^{4B}$C(O)R$^{6B}$ wherein R$^{4B}$ is hydrogen or methyl, and R$^{6B}$ is C$_{1-4}$ alkyl optionally substituted with one or more substituent independently selected from OH, NH$_2$, and OC$_{1-4}$ alkyl; and R$^{11B}$, is hydrogen.

When the MBL inhibitor is a compound of Formula (B), the MBL inhibitor is preferably selected from 5-benzenesulfonamido-1,3-thiazole-4-carboxylic acid;

5-{[(3,5-dichlorophenyl)methyl]sulfonamido}-1,3-thiazole-4-carboxylic acid;

5-(2,4,6-trimethylphenylsulfonamido)thiazole-4-carboxylic acid;

5-{[3-(trifluoromethyl)phenyl]sulfonamido}-1,3-thiazole-4-carboxylic acid;

5-(phenylmethylsulfonamido)thiazole-4-carboxylic acid;

5-(3-methoxyphenylsulfonamido)thiazole-4-carboxylic acid;

5-(2-phenylethylsulfonamido)thiazole-4-carboxylic acid;

5-(thiophene-2-sulfonamido)thiazole-4-carboxylic acid;

5-(4,5-dichlorothiophene-2-sulfonamido)thiazole-4-carboxylic acid;

5-(2,5-dichlorothiophene-3-sulfonamido)thiazole-4-carboxylic acid;

5-(2-(trifluoromethyl)phenylsulfonamido)thiazole-4-carboxylic acid;

5-(4-(trifluoromethyl)phenylsulfonamido)thiazole-4-carboxylic acid;

5-(2-chloro-5-(trifluoromethyl)phenylsulfonamido)thiazole-4-carboxylic acid;

5-(3,5-bis(trifluoromethyl)phenylsulfonamido)thiazole-4-carboxylic acid;

5-({[2-(trifluoromethyl)phenyl]methyl}sulfonamido)-1,3-thiazole-4-carboxylic acid;

5-{[(2-methylphenyl)methyl]sulfonamido}-1,3-thiazole-4-carboxylic acid;

5-((2-nitrophenyl)methylsulfonamido)thiazole-4-carboxylic acid;

5-{[(2-bromophenyl)methyl]sulfonamido}-1,3-thiazole-4-carboxylic acid;

5-(5-chlorothiophene-2-sulfonamido)thiazole-4-carboxylic acid;

5-(5-phenylthiophene-2-sulfonamido)thiazole-4-carboxylic acid;

5-(thiophene-3-sulfonamido)thiazole-4-carboxylic acid;

5-(2,5-dimethylthiophene-3-sulfonamido)thiazole-4-carboxylic acid;

5-([1,1'-biphenyl]-2-ylsulfonamido)thiazole-4-carboxylic acid;

5-((2-aminophenyl)methylsulfonamido)thiazole-4-carboxylic acid;

5-((2-acetamidophenyl)methylsulfonamido)thiazole-4-carboxylic acid;

5-((2-benzamidophenyl)methylsulfonamido)thiazole-4-carboxylic acid;

(E)-5-((2-styrylphenyl)methylsulfonamido)thiazole-4-carboxylic acid;

(E)-5-((2-(3-(dimethylamino)-3-oxoprop-1-en-1-yl)phenyl)methylsulfonamido)thiazole-4-carboxylic acid;

5-([1,1'-biphenyl]-2-ylmethylsulfonamido)thiazole-4-carboxylic acid;

5-((2-(trifluoromethoxy)phenyl)methylsulfonamido)thiazole-4-carboxylic acid;

5-((3-(trifluoromethyl)phenyl)methylsulfonamido)thiazole-4-carboxylic acid;

5-((3-bromophenyl)methylsulfonamido)thiazole-4-carboxylic acid;

5-((3-cyanophenyl)methylsulfonamido)thiazole-4-carboxylic acid;

5-((2-chlorophenyl)methylsulfonamido)thiazole-4-carboxylic acid;

5-(4-nitrophenylsulfonamido)thiazole-4-carboxylic acid;

5-({5-[5-(trifluoromethyl)-1,2-oxazol-3-yl]thiophen-2-yl}sulfonamido)-1,3-thiazole-4-carboxylic acid;

5-(1-benzothiophene-2-sulfonamido)-1,3-thiazole-4-carboxylic acid;

5-[(5-methylthiophen-2-yl)sulfonamido]-1,3-thiazole-4-carboxylic acid;

5-[(5-bromothiophen-2-yl)sulfonamido]-1,3-thiazole-4-carboxylic acid;

5-(1-benzothiophene-3-sulfonamido)-1,3-thiazole-4-carboxylic acid;

5-[(4-bromo-2,5-dichlorothiophen-3-yl)sulfonamido]-1,3-thiazole-4-carboxylic acid;

5-({[(2-chlorophenyl)methyl]sulfamoyl}amino)-1,3-thiazole-4-carboxylic acid;

5-[({[3-(trifluoromethyl)phenyl]methyl}sulfamoyl)amino]-1,3-thiazole-4-carboxylic acid;

5-[(3-bromothiophen-2-yl)sulfonamido]-1,3-thiazole-4-carboxylic acid;

5-{[(2-iodophenyl)methyl]sulfonamido}-1,3-thiazole-4-carboxylic acid;

5-{[4-phenyl-5-(trifluoromethyl)thiophen-3-yl]sulfonamido}-1,3-thiazole-4-carboxylic acid;
5-{[(2,3-dichlorophenyl)methyl]sulfonamido}-1,3-thiazole-4-carboxylic acid;
5-{[(3,4-dichlorophenyl)methyl]sulfonamido}-1,3-thiazole-4-carboxylic acid;
5-benzylsulfonamido-2-methyl-1,3-thiazole-4-carboxylic acid;
2-methyl-5-(quinoline-8-sulfonamido)-1,3-thiazole-4-carboxylic acid;
5-benzenesulfonamido-2-methyl-1,3-thiazole-4-carboxylic acid;
5-{[(3,5-dichlorophenyl)methyl]sulfonamido}-2-methyl-1,3-thiazole-4-carboxylic acid;
5-[(2-chlorophenyl)sulfonamido]-2-methyl-1,3-thiazole-4-carboxylic acid;
2-methyl-5-[(2,4,6-trimethylphenyl)sulfonamido]-1,3-thiazole-4-carboxylic acid;
5-[(2,5-dichlorothiophen-3-yl)sulfonamido]-2-methyl-1,3-thiazole-4-carboxylic acid;
5-{[(2-bromophenyl)methyl]sulfonamido}-2-methyl-1,3-thiazole-4-carboxylic acid;
5-benzenesulfonamido-2-phenyl-1,3-thiazole-4-carboxylic acid;
5-benzenesulfonamido-2-ethyl-1,3-thiazole-4-carboxylic acid;
5-[(1-phenylethyl)sulfonamido]-1,3-thiazole-4-carboxylic acid;
5-{[6-(trifluoromethyl)pyridin-3-yl]sulfonamido}-1,3-thiazole-4-carboxylic acid;
5-[(2-phenoxyethyl)sulfonamido]-1,3-thiazole-4-carboxylic acid;
5-{[2-(1,3-dioxo-2,3-dihydro-1H-isoindol-2-yl)ethyl]sulfonamido}-1,3-thiazole-4-carboxylic acid;
5-{[2-(2-chlorophenyl)ethyl]sulfonamido}-1,3-thiazole-4-carboxylic acid;
5-({1-[5-(trifluoromethyl)pyridin-2-yl]-1H-pyrazol-4-yl}sulfonamido)-1,3-thiazole-4-carboxylic acid;
5-[(2-chlorophenyl)sulfonamido]-1,3-thiazole-4-carboxylic acid;
5-(pyridine-3-sulfonamido)-1,3-thiazole-4-carboxylic acid;
5-[(2,6-dichlorophenyl)sulfonamido]-1,3-thiazole-4-carboxylic acid;
5-(cyclohexylmethyl)sulfonamido-1,3-thiazole-4-carboxylic acid;
5-[(4-methyl-3,4-dihydro-2H-1,4-benzoxazin-7-yl)sulfonamido]-1,3-thiazole-4-carboxylic acid;
5-[(1-phenylpropyl)sulfonamido]-1,3-thiazole-4-carboxylic acid;
5-{[2-(4-methoxyphenyl)ethyl]sulfonamido}-1,3-thiazole-4-carboxylic acid;
5-({2-[3-(trifluoromethyl)phenyl]ethyl}sulfonamido)-1,3-thiazole-4-carboxylic acid;
5-{[2-(4-chlorophenyl)ethyl]sulfonamido}-1,3-thiazole-4-carboxylic acid;
5-[(piperidine-1-sulfonyl)amino]-1,3-thiazole-4-carboxylic acid;
5-[(phenylsulfamoyl)amino]-1,3-thiazole-4-carboxylic acid;
5-{[benzyl(methyl)sulfamoyl]amino}-1,3-thiazole-4-carboxylic acid;
5-[(4-acetamidophenyl)sulfonamido]-1,3-thiazole-4-carboxylic acid;
5-[(2-methoxyphenyl)sulfonamido]-1,3-thiazole-4-carboxylic acid;
5-(1,2,3,4-tetrahydronaphthalene-1-sulfonamido)-1,3-thiazole-4-carboxylic acid;
5-[(5-methyl-1-phenyl-1H-pyrazol-4-yl)sulfonamido]-1,3-thiazole-4-carboxylic acid;
5-(cyclopropylmethyl)sulfonamido-1,3-thiazole-4-carboxylic acid;
5-{[(2-methoxyphenyl)methyl]sulfonamido}-1,3-thiazole-4-carboxylic acid;
5-{[2-(2-methoxyphenyl)ethyl]sulfonamido}-1,3-thiazole-4-carboxylic acid;
5-{[2-(3-methoxyphenyl)ethyl]sulfonamido}-1,3-thiazole-4-carboxylic acid;
5-{[2-(3-chlorophenyl)ethyl]sulfonamido}-1,3-thiazole-4-carboxylic acid;
5-[(2-methanesulfonylphenyl)sulfonamido]-1,3-thiazole-4-carboxylic acid;
5-{[methyl(phenyl)sulfamoyl]amino}-1,3-thiazole-4-carboxylic acid;
5-{[4-(morpholin-4-yl)phenyl]sulfonamido}-1,3-thiazole-4-carboxylic acid;
5-[(4-cyanophenyl)sulfonamido]-1,3-thiazole-4-carboxylic acid;
5-(pyridine-2-sulfonamido)-1,3-thiazole-4-carboxylic acid;
5-[(1-methyl-1H-imidazol-2-yl)sulfonamido]-1,3-thiazole-4-carboxylic acid;
5-[(6-methoxypyridin-3-yl)sulfonamido]-1,3-thiazole-4-carboxylic acid;
5-{[4-(1H-pyrazol-1-yl)phenyl]sulfonamido}-1,3-thiazole-4-carboxylic acid;
5-[(1-ethyl-5-methyl-1H-pyrazol-4-yl)sulfonamido]-1,3-thiazole-4-carboxylic acid;
5-{[(2-chlorophenyl)methyl]sulfonamido}-2-(trifluoromethyl)-1,3-thiazole-4-carboxylic acid;
5-{[(2-cyanophenyl)methyl]sulfonamido}-1,3-thiazole-4-carboxylic acid;
5-[(1-methyl-1H-pyrazol-3-yl)sulfonamido]-1,3-thiazole-4-carboxylic acid;
5-[(1-methyl-1H-pyrazol-5-yl)sulfonamido]-1,3-thiazole-4-carboxylic acid;
5-({1-[(benzyloxy)carbonyl]piperidin-4-yl}sulfonamido)-1,3-thiazole-4-carboxylic acid;
5-[(3-phenylpropyl)sulfonamido]-1,3-thiazole-4-carboxylic acid;
5-{[(2-chlorophenyl)methyl]sulfonamido}-2-methyl-1,3-thiazole-4-carboxylic acid;
5-(2,3-dihydro-1H-indene-1-sulfonamido)-1,3-thiazole-4-carboxylic acid;
5-{[4-(1-methyl-1H-pyrazol-5-yl)phenyl]sulfonamido}-1,3-thiazole-4-carboxylic acid;
5-{[2-(1,2,3,4-tetrahydroquinolin-1-yl)ethyl]sulfonamido}-1,3-thiazole-4-carboxylic acid;
5-{[2-(N-phenylacetamido)ethyl]sulfonamido}-1,3-thiazole-4-carboxylic acid;
5-{[4-(3-oxomorpholin-4-yl)phenyl]sulfonamido}-1,3-thiazole-4-carboxylic acid;
5-{[4-(2-oxo-1,3-oxazolidin-3-yl)phenyl]sulfonamido}-1,3-thiazole-4-carboxylic acid;
5-[(1,2-dimethyl-1H-imidazol-4-yl)sulfonamido]-1,3-thiazole-4-carboxylic acid;
5-[(oxan-4-ylmethyl)sulfonamido]-1,3-thiazole-4-carboxylic acid;
5-[({-[(benzyloxy)carbonyl]piperidin-4-yl}methyl)sulfonamido]-1,3-thiazole-4-carboxylic acid;
5-{[4-(2-oxopyrrolidin-1-yl)phenyl]sulfonamido}-1,3-thiazole-4-carboxylic acid;
5-({1-[6-(trifluoromethyl)pyridin-3-yl]-1H-pyrazol-4-yl}sulfonamido)-1,3-thiazole-4-carboxylic acid;
5-{[4-(1,3-oxazol-5-yl)phenyl]sulfonamido}-1,3-thiazole-4-carboxylic acid;

5-{[4-(1H-pyrazol-4-yl)phenyl]sulfonamido}-1,3-thiazole-4-carboxylic acid;
5-[(1-phenyl-1H-pyrazol-4-yl)sulfonamido]-1,3-thiazole-4-carboxylic acid;
5-{[4-(piperidin-4-yl)phenyl]sulfonamido}-1,3-thiazole-4-carboxylic acid;
5-[(4-propanamidophenyl)sulfonamido]-1,3-thiazole-4-carboxylic acid;
5-{[4-(2-hydroxyacetamido)phenyl]sulfonamido}-1,3-thiazole-4-carboxylic acid;
5-({4-[(methylcarbamoyl)amino]phenyl}sulfonamido)-1,3-thiazole-4-carboxylic acid;
5-{[(2,4-dichlorophenyl)methyl]sulfonamido}-1,3-thiazole-4-carboxylic acid;
5-{[(2-fluorophenyl)methyl]sulfonamido}-1,3-thiazole-4-carboxylic acid;
5-{[(2,3-difluorophenyl)methyl]sulfonamido}-1,3-thiazole-4-carboxylic acid;
5-{[4-(2-methoxyacetamido)phenyl]sulfonamido}-1,3-thiazole-4-carboxylic acid;
5-{[(2,5-dichlorophenyl)methyl]sulfonamido}-1,3-thiazole-4-carboxylic acid;
5-{1[(2,6-dichlorophenyl)methyl]sulfonamido}-1,3-thiazole-4-carboxylic acid;
5-{1[(2-chloro-6-fluorophenyl)methyl]sulfonamido}-1,3-thiazole-4-carboxylic acid;
5-{1[(2-chloro-4-fluorophenyl)methyl]sulfonamido}-1,3-thiazole-4-carboxylic acid;
5-({[2-chloro-5-(trifluoromethyl)phenyl]methyl}sulfonamido)-1,3-thiazole-4-carboxylic acid;
5-({4-[(dimethylamino)methyl]phenyl}sulfonamido)-1,3-thiazole-4-carboxylic acid;
5-{1[(2,3,5-trichlorophenyl)methyl]sulfonamido}-1,3-thiazole-4-carboxylic acid;
5-{1[(2,3-dichloro-6-fluorophenyl)methyl]sulfonamido}-1,3-thiazole-4-carboxylic acid;
5-({[2,3-dichloro-6-(trifluoromethyl)phenyl]methyl}sulfonamido)-1,3-thiazole-4-carboxylic acid;
5-{1[(4-bromo-2-chlorophenyl)methyl]sulfonamido}-1,3-thiazole-4-carboxylic acid;
5-({2-[methyl(phenyl)amino]ethyl}sulfonamido)-1,3-thiazole-4-carboxylic acid;
5-{1[(4-nitrophenyl)methyl]sulfonamido}-1,3-thiazole-4-carboxylic acid;
5-[6-(piperidin-1-yl)pyridin-3-ylsulfonamido]-1,3-thiazole-4-carboxylic acid;
5-[6-(methylamino)pyridin-3-ylsulfonamido]-1,3-thiazole-4-carboxylic acid;
5-[6-(4-methylpiperazin-1-yl)pyridin-3-ylsulfonamido]-1,3-thiazole-4-carboxylic acid;
5-(6-acetamidopyridin-3-ylsulfonamido)-1,3-thiazole-4-carboxylic acid;
5-{4-[(5-methyl-1,2-oxazol-3-yl)amino]phenylsulfonamido}-1,3-thiazole-4-carboxylic acid;
5-(6-aminopyridin-3-ylsulfonamido)-1,3-thiazole-4-carboxylic acid;
5-[(6-chloro-2H-1,3-benzodioxol-5-yl)methylsulfonamido]-1,3-thiazole-4-carboxylic acid;
5-{[(2-chloro-6-nitrophenyl)methyl]sulfonamido}-1,3-thiazole-4-carboxylic acid;
5-(quinoline-6-sulfonamido)-1,3-thiazole-4-carboxylic acid;
5-[(2,3-dihydroindole-1-sulfonyl)amino]-1,3-thiazole-4-carboxylic acid;
5-(4-methanesulfonylphenylsulfonamido)-1,3-thiazole-4-carboxylic acid;
5-[3-(2-oxo-1,3-oxazolidin-3-yl)phenylsulfonamido]-1,3-thiazole-4-carboxylic acid;
5-[3-(2H-pyrazol-3-yl)phenylsulfonamido]-1,3-thiazole-4-carboxylic acid;
5-[2-(pyridin-3-yl)ethylsulfonamido]-1,3-thiazole-4-carboxylic acid;
5-[3-(3-oxomorpholin-4-yl)phenylsulfonamido]-1,3-thiazole-4-carboxylic acid;
5-[3-(2-oxopyrrolidin-1-yl)phenylsulfonamido]-1,3-thiazole-4-carboxylic acid;
5-[6-(piperidin-4-ylamino)pyridin-3-ylsulfonamido]-1,3-thiazole-4-carboxylic acid;
5-(6-{[2-(dimethylamino)ethyl]amino}pyridin-3-ylsulfonamido)-1,3-thiazole-4-carboxylic acid;
5-[(4-acetamidophenyl)methylsulfonamido]-1,3-thiazole-4-carboxylic acid;
5-[6-(piperazin-1-yl)pyridin-3-ylsulfonamido]-1,3-thiazole-4-carboxylic acid;
5-[6-(4-aminopiperidin-1-yl)pyridin-3-ylsulfonamido]-1,3-thiazole-4-carboxylic acid;
5-[6-(3-aminopyrrolidin-1-yl)pyridin-3-ylsulfonamido]-1,3-thiazole-4-carboxylic acid;
5-[6-(pyrrolidin-1-yl)pyridin-3-ylsulfonamido]-1,3-thiazole-4-carboxylic acid;
5-[6-(3-aminopiperidin-1-yl)pyridin-3-ylsulfonamido]-1,3-thiazole-4-carboxylic acid;
5-[6-(1,4-diazepan-1-yl)pyridin-3-ylsulfonamido]-1,3-thiazole-4-carboxylic acid;
5-[4-(pyrrolidin-3-yloxy)phenylsulfonamido]-1,3-thiazole-4-carboxylic acid;
5-[6-(3-aminoazetidin-1-yl)pyridin-3-ylsulfonamido]-1,3-thiazole-4-carboxylic acid;
5-[6-(piperidin-4-yl)pyridin-3-ylsulfonamido]-1,3-thiazole-4-carboxylic acid;
5-[6-(1,2,3,6-tetrahydropyridin-4-yl)pyridin-3-ylsulfonamido]-1,3-thiazole-4-carboxylic acid;
5-{6-[4-(2,2,2-trifluoroethyl)piperazin-1-yl]pyridin-3-ylsulfonamido}-1,3-thiazole-4-carboxylic acid;
5-[1-(2-chlorophenyl)ethylsulfonylamino]thiazole-4-carboxylic acid;
5-[1-(2-chlorophenyl)ethylsulfonylamino]thiazole-4-carboxylic acid;
5-(3-pyridylmethylsulfonylamino)thiazole-4-carboxylic acid;
5-(isoindolin-5-ylmethylsulfonylamino)thiazole-4-carboxylic acid;
R-5-[[4-[1-(2-amino-2-phenyl-acetyl)-4-piperidyl]phenyl]sulfonylamino]thiazole-4-carboxylic acid;
S-5-[[4-[1-(2-amino-2-phenyl-acetyl)-4-piperidyl]phenyl]sulfonylamino]thiazole-4-carboxylic acid;
5-[[4-[(2-aminoacetyl)amino]phenyl]sulfonylamino]thiazole-4-carboxylic acid;
5-[(4-acetamido-3-fluoro-phenyl)sulfonylamino]thiazole-4-carboxylic acid;
5-[[4-[(2-hydroxy-2-methyl-propanoyl)amino]phenyl]sulfonylamino]thiazole-4-carboxylic acid;
5-[[4-[(2-hydroxy-2-phenyl-acetyl)amino]phenyl]sulfonylamino]thiazole-4-carboxylic acid;
5-[[4-[(2-hydroxy-3-phenyl-propanoyl)amino]phenyl]sulfonylamino]thiazole-4-carboxylic acid;
5-[[2-(2-hydroxyethylamino)pyrimidin-5-yl]sulfonylamino]thiazole-4-carboxylic acid;
5-[(2-methylpyrimidin-5-yl)sulfonylamino]thiazole-4-carboxylic acid;
5-[[2-(4-pyridyl)pyrimidin-5-yl]sulfonylamino]thiazole-4-carboxylic acid;

5-[(6-methyl-3-pyridyl)sulfonylamino]thiazole-4-carboxylic acid;

5-[(2-chloro-3-nitro-phenyl)methylsulfonylamino]thiazole-4-carboxylic acid;

and pharmaceutically acceptable salts thereof.

Compounds of Formula (B) and pharmaceutically acceptable salts thereof are described in WO 2014/198849.

The invention therefore provides a combination of a compound of the invention as described herein, e.g. a compound of Formula (I), (II) or (III) wherein R is as defined herein, preferably wherein R is halogen, and an MBL inhibitor of Formula (A) or Formula (B) as defined herein, wherein the MBL inhibitor is preferably of Formula (A). The combination may further comprise an antibiotic agent as described herein. The combination may be in the form of a pharmaceutical composition further comprising a pharmaceutically acceptable carrier or diluent.

The compounds, compositions or combinations described herein may be administered in a variety of dosage forms. Thus, they can be administered orally, for example as tablets, troches, lozenges, aqueous or oily suspensions, dispersible powders or granules. They may also be administered parenterally, whether subcutaneously, intravenously, intramuscularly, intrasternally, transdermally or by infusion techniques. The compound, composition or combination may also be administered as a suppository. Preferably, the compound, composition or combination is administered via parenteral administration, in particular via intravenous administration.

The compounds, compositions or combinations described herein are typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. Suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection may contain as carrier, for example, sterile water or preferably they may be in the form of sterile, aqueous, isotonic saline solutions. Compositions for injection (e.g. i.v. administration) may contain excipients for increasing the solubility of component compounds (e.g. compounds of the invention). Suitable excipients include cyclodextrins such as captisol. Pharmaceutical compositions suitable for delivery by needleless injection, for example, transdermally, may also be used.

Therapeutic Efficacy

The compounds of the present invention are therapeutically useful. The present invention therefore provides compounds, compositions and combinations as described herein, for use in medicine. The present invention provides compounds as described herein, for use in treating the human or animal body. For the avoidance of doubt, the compound of the invention may be administered in the form of a solvate.

The compounds, compositions and combinations of the invention are useful in treating or preventing bacterial infection. The present invention therefore provides a compound, composition or combination of the invention for use in treating or preventing bacterial infection. The invention also provides the use of a compound, composition or combination of the invention in the manufacture of a medicament for use in the prevention or treatment of bacterial infection. The invention also provides a method of treating or preventing bacterial infection in a subject in need thereof, which method comprises administering to said subject an effective amount of a compound, composition or combination as described herein.

The compounds of the invention may be used as standalone therapeutic agents. For example, the compounds of the invention may be used as standalone adjuncts in antibacterial therapy, for example in chemotherapy regimes. Alternatively, they may be used in combination with antibiotic agents, and optionally with MBL inhibitors, to enhance the action of the antibiotic agent. The compounds of the invention may find particular use in treating or preventing bacterial infection caused by bacteria which are resistant to treatment with antibiotic agents when administered alone, particularly where the resistance is caused by presence of SBL enzymes. Treatment or prevention of such infection with β-lactam antibiotics alone may be unsuccessful. The compounds are therefore useful in the removal or reduction of antibiotic resistance, in particular in Gram-negative bacteria. In particular, the compounds are useful in removing or reducing resistance caused by SBL enzymes.

The invention also provides a compound of the invention for use in treating or preventing bacterial infection by co-administration with (i) an antibiotic agent and/or (ii) an MBL inhibitor. Also provided is an antibiotic agent for use in treating or preventing bacterial infection by co-administration with (i) a compound of the invention and optionally (ii) an MBL inhibitor. Also provided is an MBL inhibitor for use in treating or preventing bacterial infection by co-administration with (i) a compound of the invention and optionally (ii) an antibiotic agent.

Also provided is the use of a compound of the invention in the manufacture of a medicament for use in treating or preventing bacterial infection by co-administration with (i) an antibiotic agent and/or (ii) an MBL inhibitor. Also provided is the use of an antibiotic agent in the manufacture of a medicament for use in treating or preventing bacterial infection by co-administration with (i) a compound of the invention and optionally (ii) an MBL inhibitor. Also provided is the use of an MBL inhibitor in the manufacture of a medicament for use in treating or preventing bacterial infection by co-administration with (i) a compound of the invention and optionally (ii) an antibiotic agent.

Also provided is a method of treating or preventing bacterial infection in a subject in need thereof, which method comprises co-administering a compound of the invention with (i) and antibiotic agent and/or (ii) an MBL inhibitor.

In one aspect, the subject to be treated is a mammal, in particular a human. However, it may be non-human. Preferred non-human animals include, but are not limited to, primates, such as marmosets or monkeys, commercially farmed animals, such as horses, cows, sheep or pigs, and pets, such as dogs, cats, mice, rats, guinea pigs, ferrets, gerbils or hamsters. The subject can be any animal that is capable of being infected by a bacterium.

The compounds, compositions and combinations described herein are useful in the treatment of bacterial infection which occurs after a relapse following an antibiotic treatment. The compounds, compositions and combinations can therefore be used in the treatment of a patient who has previously received antibiotic treatment for the (same episode of) bacterial infection.

The bacterium causing the infection may be any bacterium expressing an SBL enzyme or an analogue thereof. Typically the bacterium causing the infection expresses an SBL enzyme. The bacterium is typically Gram-negative. The bacterium may in particular be a pathogenic bacterium. Typically, the bacterial infection to be treated using the compounds of the invention is resistant to treatment with a conventional antibiotic when the conventional antibiotic is used alone or in a combination with another partner. For example, the bacterial infection to be treated using the compounds of the invention may be resistant to treatment when the conventional antibiotic is used solely in combination with an MBL inhibitor.

The Gram-negative bacteria of which antibiotic resistance can be removed using the compounds of general formula (I) are bacteria which produce serine-β-lactamases, which may be serine-β-lactamases of subclasses A, C or D. In particular, the bacteria may be those which produce extended spectrum β-lactamases (ESBLs) and/or carbapenemases, in particular the OXA and/or KPC classes of carbapenemases, preferably the OXA class of carbapenamases.

The bacterial infection may be caused by bacteria from the families Enterobacteriaceae, Pseudomonadaceae and/or Moraxellaceae, more typically the bacterial infection is caused by bacteria from the families Enterobacteriaceae and/or Pseudomonadaceae, and most typically the bacterial infection is caused by bacteria from the family Enterobacteriaceae. The bacterial infection may be caused by *Pseudomonas* (e.g. *Pseudomonas aeruginosa, Pseudomonas oryzihabitans*, or *Pseudomonas plecoglossicida*), *Klebsiella, Escherichia, Enterobacter, Acinetobacter* or *Burkholderia*. Preferably the bacterial infection may be caused by *Pseudomonas* (e.g. *Pseudomonas aeruginosa, Pseudomonas oryzihabitans*, or *Pseudomonas plecoglossicida*), *Klebsiella, Escherichia, Enterobacter*, or *Acinetobacter* More preferably, the bacterial infection is caused by *Acinetobacter* or *Klebsiella*, most preferably *Acinetobacter*. For example, the bacterial infection may be caused by *Klebsiella pneumoniae, Escherichia coli, Enterobacter Cloacae, Pseudomonas aeruginosa, Burkholderia cepacia* or *Acinetobacter baumannii*. Preferably, the bacterial infection may be caused by *Klebsiella pneumoniae, Escherichia coli, Enterobacter Cloacae, Pseudomonas aeruginosa*, or *Acinetobacter baumannii*. More preferably, the bacterial infection is caused by *Acinetobacter baumannii* or *Klebsiella pneumoniae*, most preferably *Acinetobacter baumannii*. The bacterium may be an opportunistic pathogen.

The compound, composition or combination of the invention may be used to treat or prevent infections and conditions caused by any one or a combination of the above-mentioned bacteria. In particular, the compound, composition or combination of the invention may be used in the treatment or prevention of pneumonia. The compound, composition or combination may also be used in the treatment of septic shock, urinary tract infection, and infections of the gastro-intestinal tract, skin or soft tissue.

The compound, composition or combination of the invention may be used to treat patients with Carbapenem Resistant Enterobacteriaceae (CRE). CRE can be found in the community or in hospitals and other institutions which are commonly associated with long term patients and those that are undergoing significant medical interventions such as are commonly cared for in Intensive Care Units (ICUs).

A compound, composition or combination of the invention can be administered to the subject in order to prevent the onset or reoccurrence of one or more symptoms of the bacterial infection. This is prophylaxis. In this embodiment, the subject can be asymptomatic. The subject is typically one that has been exposed to the bacterium. A prophylactically effective amount of the agent or formulation is administered to such a subject. A prophylactically effective amount is an amount which prevents the onset of one or more symptoms of the bacterial infection.

A compound, composition or combination of the invention can be administered to the subject in order to treat one or more symptoms of the bacterial infection. In this embodiment, the subject is typically symptomatic. A therapeutically effective amount of the agent or formulation is administered to such a subject. A therapeutically effective amount is an amount effective to ameliorate one or more symptoms of the disorder.

A therapeutically or prophylactically effective amount of the compound of the invention is administered to a subject. The dose may be determined according to various parameters, especially according to the compound used; the age, weight and condition of the subject to be treated; the route of administration; and the required regimen. A physician will be able to determine the required route of administration and dosage for any particular subject. A typical daily dose is from about 0.01 to 100 mg per kg, preferably from about 0.1 mg/kg to 50 mg/kg, e.g. from about 1 to 10 mg/kg of body weight, according to the activity of the specific inhibitor, the age, weight and conditions of the subject to be treated, the type and severity of the disease and the frequency and route of administration. Preferably, daily dosage levels are from 70 mg to 3.5 g. Sometimes, higher dosages are required, such as from about 0.01 to about 250 mg per kg, e.g. from about 0.1 mg/kg to about 200 mg/kg, e.g. from about 1 to about 150 mg/kg of body weight, according to the activity of the specific inhibitor, the age, weight and conditions of the subject to be treated, the type and severity of the disease and the frequency and route of administration. Such preferred daily dosage levels may be e.g. from 70 mg to 8 g. Higher dosages may be particularly suitable if the compound of the invention is administered to the subject multiple times per day, such as 2, 3 or 4 times per day, e.g. 4 times daily. A suitable daily dosage may be from 70 mg to 8 g per day administered in 2, 3 or 4 separate dosages.

When the compound of the invention is administered to a subject in combination with another active agent (for example in the form of a pharmaceutical combination comprising an antibiotic agent and optionally an MBL inhibitor), the dose of the other active agent (e.g. MBL inhibitor and/or antibiotic agent) can be determined as described above. The dose may be determined according to various parameters, especially according to the agent used; the age, weight and condition of the subject to be treated; the route of administration; and the required regimen. Again, a physician will be able to determine the required route of administration and dosage for any particular subject. A typical daily dose is from about 0.01 to 100 mg per kg, preferably from about 0.1 mg/kg to 50 mg/kg, e.g. from about 1 to 10 mg/kg of body weight, according to the activity of the specific inhibitor, the age, weight and conditions of the subject to be treated, the type and severity of the disease and the frequency and route of administration. Preferably, daily dosage levels are from 70 mg to 3.5 g. Sometimes, higher dosages are required, such as from about 0.01 to about 250 mg per kg, e.g. from about 0.1 mg/kg to about 200 mg/kg, e.g. from about 1 to about 150 mg/kg of body weight, according to the activity of the specific inhibitor, the age, weight and conditions of the subject to be treated, the type and severity of the disease and the frequency and route of administration. Such preferred daily dosage levels may be e.g. from 70 mg to 8 g. Higher dosages may be particularly suitable if the combination or composition of the invention is administered to the subject multiple times per day, such as 2, 3 or 4 times per day, e.g. 4 times daily. A suitable daily dosage may be from 70 mg to 8 g per day administered in 2, 3 or 4 separate dosages.

The following Examples illustrate the invention. They do not however, limit the invention in any way. In this regard, it is important to understand that the particular assay used in the Examples section is designed only to provide an indication of biological activity. There are many assays available to determine biological activity, and a negative result in any one particular assay is therefore not determinative.

EXPERIMENTAL DETAILS

General Synthetic Methodology

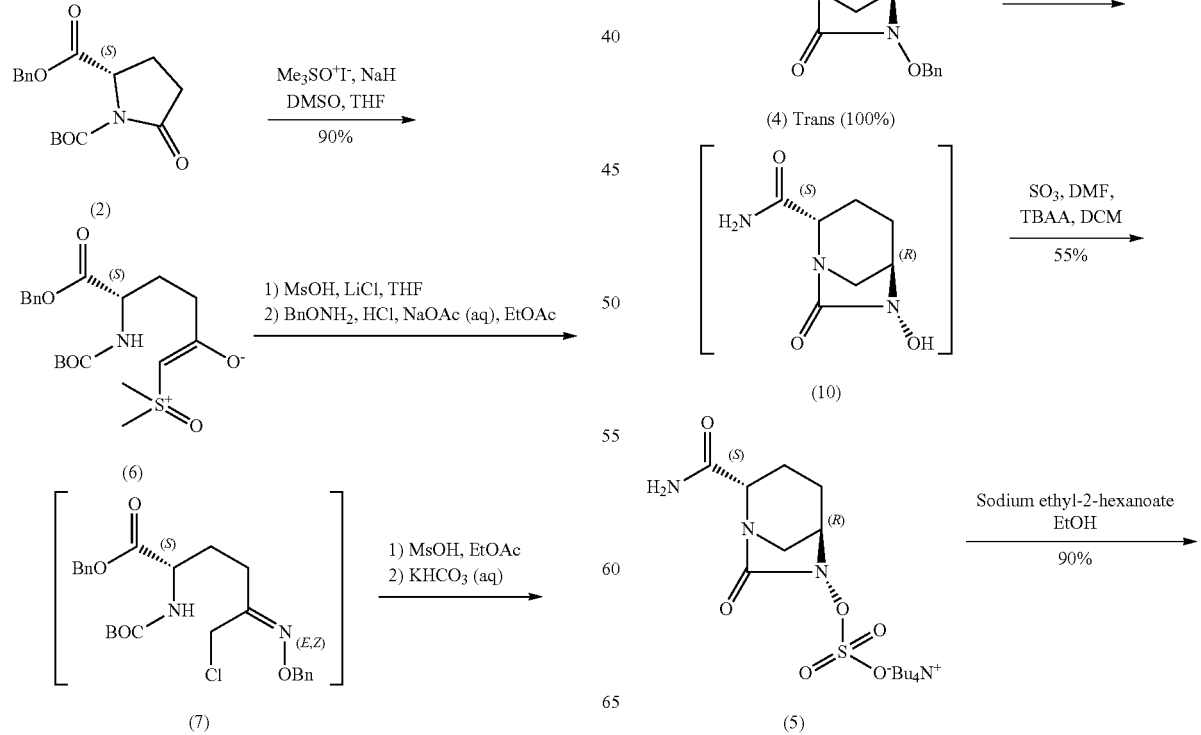

-continued

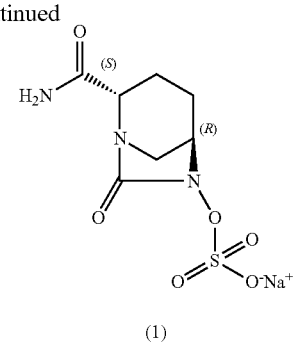

(1)

There are a number of approaches to the synthesis of avibactam (1). One of the major routes is shown in Scheme 1, reproduced from Ball, M. et al, Organic Process Research and Development, 2016, 20, 1799. The BOC-pyrrolidinone (2) reacts with sulfoxonium ylid reagent to give in situ the new ring-opened ylid (6). Protonation generates a positively charged sulfoxonium species which is nucleophilically attacked by chloride anion, resulting in loss of DMSO and generating the chloromethyl ketone which condenses with O-benzyl hydroxylamine to give oxime (7). Again, this is not isolated but treated with acid to remove the BOC protecting group and on basification spontaneous cyclisation occurs with formal loss of HCl to give ring expanded (8). Once again this is not isolated but stereoselective reduction of the oxime double bond followed by salt formation with oxalic acid facilitates isolation of piperidine (3). Cyclisation using triphosgene as a phosgene source generates the bicyclic urea (9) then ester hydrolysis and amide formation generates the primary carboxamide of avibactam as in (4). Finally debenzylation and sulfonation produces avibactam (1).

Use of substituents other than ester on the starting pyrrolidinone can access alternative analogues of avibactam. Furthermore, intermediate (3) is now commercially available (eg from Shanghai Habo Chemical Technology Company or Frapps Chemicals Co, Zhejiang, China, http://www.frappschem.com), so a variety of substituents can be accessed from this later stage intermediate. Examples are shown in schemes 2a and b below.

Scheme 2a

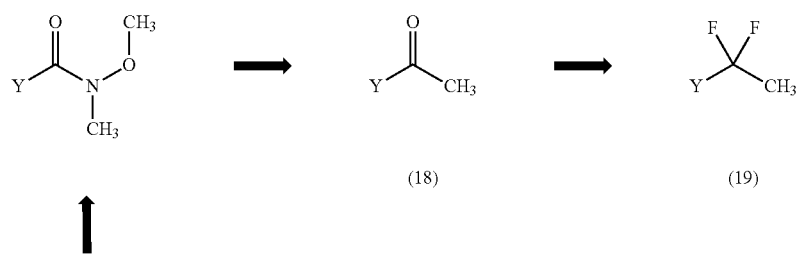

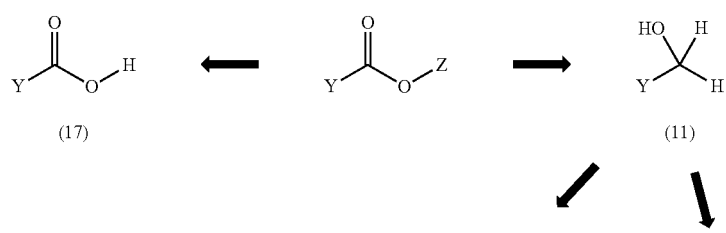

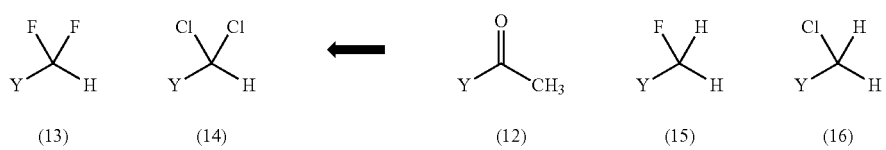

Sheme 2b

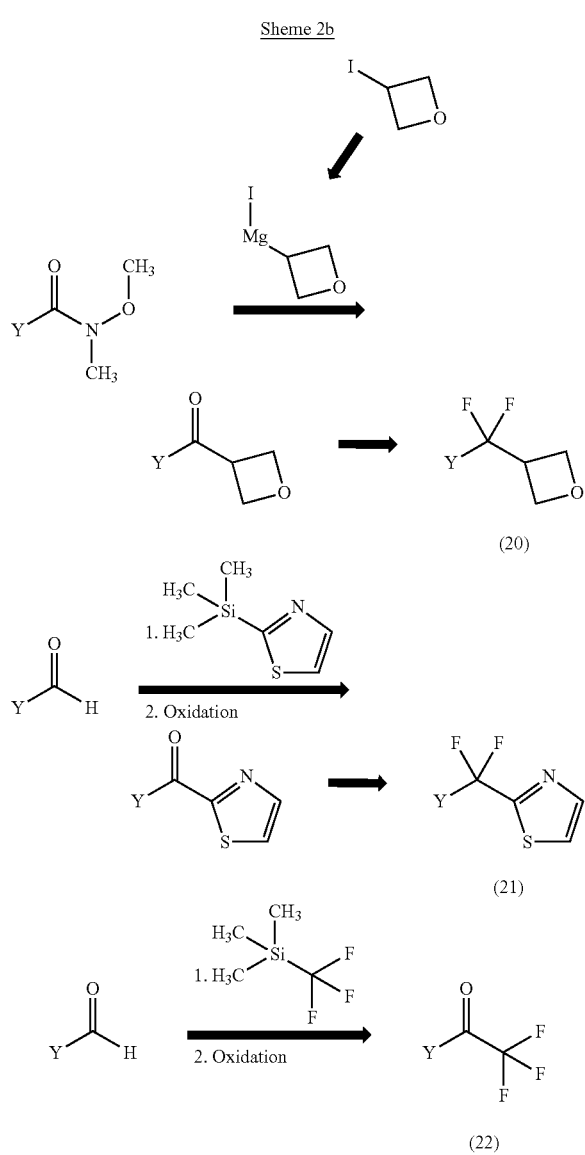

In Schemes 2a and 2b, Z represents a suitable ester substituent such as the benzyl group in (9) of Scheme 1. Y represents the group:

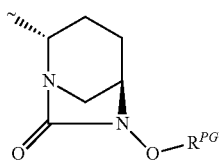

where $R^{PG}$ represents a protecting group, for example a benzyl or —$CH_2CH=CH_2$ group. This protecting group can be removed after synthesis of the remainder of the compound, and the $SO_3H$ or $SO_3^-$ group provided, in a similar manner to that depicted in Scheme 1 above.

As depicted in Scheme 2a, the ester functionality such as (9) in Scheme 1 can be reduced to an alcohol (11) which can be oxidised to an aldehyde (12). The aldehyde can be transformed into a difluoromethyl substituent (13) or a dichloromethyl substituent (14) using DAST (diethylaminosulfur trifluoride, see Xu, Y., Prestwich, G. D., Journal of Organic Chemistry, 2002, 67, 20, 7158-7161) or PC15 (Gauthier, J. et al, Bioorganic and Medicinal Chemistry Letters, 2008, 18, 923-928) or similar reagents, chemistry that is well known to those skilled in the art. Similarly the alcohol can be transformed into fluoromethyl (15) with DAST (Liu, Y. et al, Organic Letters, 2004, 6, 209-212) and chloromethyl (16) with thionyl chloride (Gudipati, V. et al, Journal of Organic Chemistry, 2006, 71, 3599-3607). Also the acid (17) can be converted to methyl ketone (18) using standard Weinreb amide chemistry which can be similarly converted into the difluoroethyl substituent (19) with DAST.

A wide range of substituents can be accessed using Weinreb amide chemistry as shown in Scheme 2b. For instance, the Grignard derived from 3-iodooxetane (commercially-available from Sigma Aldrich) can in principle react with the aforementioned Weinreb reagent to produce the analogous ketone which can be converted to the difluro analogue (20) using the usual DAST reagent. This chemistry can also be applied to longer chain alkyldifluoromethylene substituents as well as aryldifluoromethylene substituents.

For certain specific heterocycles, alternative chemistry may be used. For instance 2-trimethylthiazole can react with aldehydes followed by TMS ether cleavage and oxidation of the alcohol to generate the 2-thiazolyl ketone (21) (for an example of this chemistry, see Dondoni, A. et al, JOC2004, 69, 5023) which can be transformed into the difluoromethylene using DAST reagent. Related silicon chemistry can be used to generate for example the trifluoromethyl ketone substituent, as (trifluoromethyl)trimethylsilane can react with aldehydes to give the corresponding carbinol (Cheng, H., et al Tet. Lett., 2013, 54, 4483). Standard oxidation then accesses the trifluoromethyl ketone (22).

EXAMPLES

General Techniques

1H NMR spectra are reported at 300 or 400 MHz in DMSO-d6 solutions (δ in ppm), using chloroform as the reference standard (7.25 ppm). When peak multiplicities are reported, the following abbreviations are used: s (singlet), d (doublet), t (triplet), m (multiplet), bs (broadened singlet), dd (doublet of doublets), dt (doublet of triplets), q (quartet). Coupling constants, when given, are reported in hertz (Hz).

All reactions were conducted under an inert atmosphere of nitrogen or argon, unless stipulated (eg hydrogenations reactions).

ABBREVIATIONS

ACN acetonitrile
DAST diethylaminosulfur trifluoride
DCM dichloromethane
DIPEA N,N-diisopropylethylamine
DMAP 4-dimethylaminopyridine
DMSO dimethylsulfoxide
h hours
HMBC heteronuclear multiple bond correlation
p.s.i pounds per square inch
SO3:pyr pyridine-sulfur trioxide complex
TEA triethylamine
TEMPO (2,2,6,6-tetramethylpiperidin-1-yl)oxyl THF tetrahydrofuran

Example 1

Sodium (2S, 5R)-7-oxo-2-(trifluoromethyl)-1,6-diazabicyclo[3.2.1]octan-6-yl sulfate

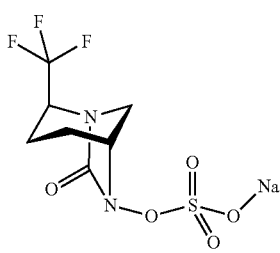

This was prepared using essentially the same methodology as reported for avibactam (Ball, M. et al, Organic Process Research and Development, 2016, 20, 1799) except starting from (5S)-5-(trifluoromethyl)-2-pyrrolidinone.

a. tert-Butyl (5S)-2-oxo-5-(trifluoromethyl)pyrrolidine-1-carboxylate

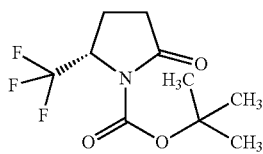

A solution of (5S)-5-(trifluoromethyl)-2-pyrrolidinone (commercially available from Manchester Organics) (5 g, 32.7 mmol) in DCM (60 mL) at 0° C. was treated with triethylamine (5.5 mL, 4.0 g, 39.2 mmol) and DMAP (0.4 g, 0.1 mmol) then a solution of di-tert butyl dicarbonate (8.6 g, 39.2 mmol) in DCM (20 mL) was added dropwise over 10 minutes. After 0.5 h the mixture was partitioned between DCM and 10% aqueous citric acid and the organic extract washed with water, dried (Na$_2$SO$_4$) and evaporated affording an oil (9.4 g) which was chromatographed on silica eluting with 0-25% ethyl acetate in toluene affording an oil (7.9 g, 96%).

M/z 276 (M+Na)$^+$.

b. (3R,6S)—N-(Benzyloxy)-6-(trifluoromethyl)piperidin-3-amine

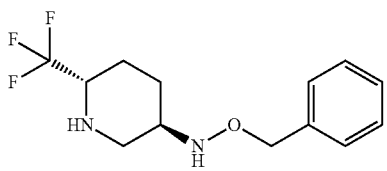 [SMILES: FC(F)(F)[C@@H]1CC[C@@H](NOCc2ccccc2)CN1]

For a detailed explanation of this reaction sequence see (Ball, M. et al, Organic Process Research and Development, 2016, 20, 1799).

DMSO (10 mL) was added to a mixture of trimethylsulfoxonium iodide (1.6 g, 7.3 mmol) and potassium t-butoxide (0.72 g, 6.4 mmol) in THF (7 mL). The mixture was stirred at room temperature for 1 h then cooled to −12° C. (internal temperature). A solution of tert-butyl (5S)-2-oxo-5-(trifluoromethyl)pyrrolidine-1-carboxylate (1.5 g, 5.8 mmol) in THF (4 mL) was added dropwise over 5 minutes and the mixture stirred at −12° C. for 1 h. The reaction mixture was treated with 20% aqueous ammonium chloride (13 mL) and the stirred mixture was allowed to warm to room temperature then extracted twice with ethyl acetate. The combined extracts were washed with 10% aqueous sodium chloride solution and then concentrated to approximately a 20 mL solution which was used directly in the next stage.

Mass Spectroscopy of the Solution was Consistent with the Formation of (1Z,5S)-5-{[(tert-butoxy)carbonyl]amino}-1-[dimethyl(oxo)-lambda-6-sulfanyliumyl]-6,6,6-trifluorohex-1-en-2-olate The above ethyl acetate solution (20 mL) was treated with O-benzylhydroxylamine hydrochloride and the mixture heated at 60° C. for 2.75 h then allowed to cool to room temperature before washing with 10% aqueous sodium chloride solution. This solution was reduced in volume to approximately 10 mL and used directly in the next step.

(Mass spectroscopy of the solution was consistent with the formation of tert-butyl N-[(2S,5E/Z)-5-[(benzyloxy)imino]-6-chloro-1,1,1-trifluorohexan-2-yl]carbamate).

The above ethyl acetate solution (10 mL) was treated with methanesulfonic acid (1.1 mL, 1.7 g, 17.4 mmol) and the mixture heated at 45° C. for 1 h then allowed to cool to room temperature. This was added to a solution of potassium bicarbonate (2.9 g, 29 mmol) in water (10 mL) and stirred at 45° C. for 3 h. After cooling the phases were separated and the ethyl acetate phase washed with 10% aqueous sodium chloride solution. The ethyl acetate solution was used as such in the next stage.

(Mass spectroscopy of the solution was consistent with the formation of (3E/Z,6S)—N-(benzyloxy)-6-(trifluoromethyl)piperidin-3-imine).

The above ethyl acetate solution was cooled to −15° C. and concentrated sulfuric acid (0.6 g, 0.3 mL, 6 mmol) was added. Then sodium triacetoxyborohydride (0.5 g, 2.4 mmol) was added portion wise, allowing the temperature to rise from −15° C. to −5° C. over 1 h. Water was added followed by concentrated aqueous ammonia (1 mL). The mixture was extracted with ethyl acetate and the organic extract washed with brine, dried and evaporated affording an oil which was chromatographed on silica eluting with 15-40% ethyl acetate in DCM affording (3R,6S)—N-(benzyloxy)-6-(trifluoromethyl)piperidin-3-amine as an oil (184 mg, 12% over 4 stages).

M/z 275 (M+H)$^+$.

c. (2S,5R)-6-(Benzyloxy)-2-(trifluoromethyl)-1,6-diazabicyclo[3.2.1]octan-7-one

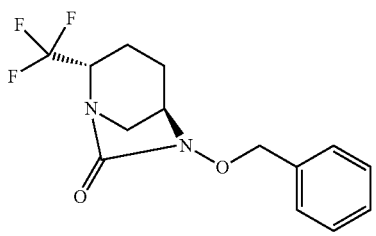 [SMILES: O=C1N2C[C@@H](CC[C@H]2C(F)(F)F)N1OCc1ccccc1]

A mixture of (3R,6S)—N-(benzyloxy)-6-(trifluoromethyl)piperidin-3-amine (0.18 g, 0.67 mmol) and potassium carbonate (0.53 g, 3.82 mmol) in DCM (20 mL) was treated with triphosgene (0.2 g, 0.67 mmol) at −10° C. After 30 minutes DMAP (3 mg, 0.03 mmol) was added. The reaction mixture was stirred at room temperature overnight then washed with water, dried (Na$_2$SO$_4$) and evaporated. The residue was chromatographed on silica eluting with an ethyl acetate-DCM gradient affording a colourless solid (0.16 g, 81%).

M/z 301.4 (M+H)$^+$.

d. Sodium (2S,5R)-7-oxo-2-(trifluoromethyl)-1,6-diazabicyclo[3.2.1]octan-6-yl sulfate A solution of (2S,5R)-6-(benzyloxy)-2-(trifluoromethyl)-1,6-diazabicyclo[3.2.1]octan-7-one (163 mg, 0.54 mmol) in iso-propanol (5 mL) was treated with sulfur trioxide trimethylamine complex (85 mg, 0.61 mmol), triethylamine (11 mg, 0.11 mmol), 10% palladium on charcoal (10 mg) and water (0.6 mL). The mixture was hydrogenated under balloon pressure for 4.5 h then more sulfur trioxide trimethylamine complex (82 mg, 0.3 mmol) was added. The mixture was stirred under nitrogen for 2 h then filtered and concentrated to approximately 1.5 mL. This was diluted with water and treated with saturated aqueous sodium bicarbonate solution (3 mL). The mixture was loaded onto a reverse phase C18 cartridge (10 g size) and eluted with 0-40% ACN in water. Evaporation of product-containing fractions gave a white solid that was redissolved in water and rechromatographed using the same chromatography conditions. Evaporation of product-containing fractions gave a white solid that was redissolved in water and rechromatographed using the similar chromatography conditions except that THF was used in place of ACN. Evaporation gave the title compound as a white solid (86 mg, 51%).

$^1$H NMR (400 MHz, d$_6$-DMSO) δ 4.09-4.06 (1H, m), 3.89-3.78 (1H, m), 3.24 (1H, d, J=12.0 Hz), 3.13-3.08 (1H, m), 1.92-1.74 (4H, m).

$^{19}$F NMR (376.4 MHz, d$_6$-DMSO) δ -74.7

LCMS (ESI [M-Na]$^−$) 289.1, (97.2%).

Example 2

Sodium (2S,5R)-7-oxo-2-(difluoromethyl)-1,6-diazabicyclo[3.2.1]octan-6-yl sulfate

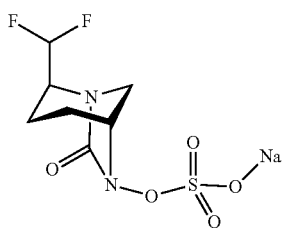

a. Ethyl (2S,5R)-6-(benzyloxy)-7-oxo-1,6-diazabicyclo[3.2.1]octane-2-carboxylate

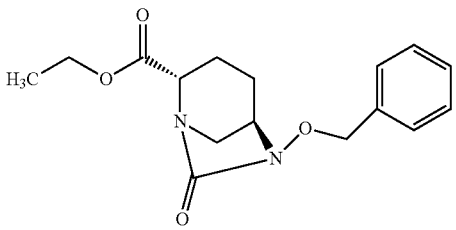 [SMILES: CCOC(=O)[C@@H]1CC[C@@H]2CN1C(=O)N2OCc1ccccc1]

A suspension of ethyl (2S,5R)-5-[(benzyloxy)amino]piperidine-2-carboxylate oxalate salt (15.0 g, 40.7 mmol; purchased from Frapps Chemicals Co, Zhejiang, China, http://www.frappschem.com) in THF (150 mL) at 0° C. was treated with a solution of potassium hydrogen carbonate (16.3 g, 163 mmol) in water (150 mL). After 1 hour the mixture was extracted with ethyl acetate and the combined extracts washed with water then brine, dried (Na$_2$SO$_4$) and evaporated affording ethyl (2S,5R)-5-[(benzyloxy)amino]piperidine-2-carboxylate as a brown oil (10.0 g, 88%).

A solution of ethyl (2S,5R)-5-[(benzyloxy)amino]piperidine-2-carboxylate (5.0 g, 18 mmol) in DCM (100 mL) at 0° C. was treated with DIPEA (12.5 mL, 72 mmol) followed by the addition of a solution of triphosgene (2.6 g, 9 mmol) in DCM (10 mL). The mixture was stirred at ambient temperature for 16 h then saturated aqueous potassium bicarbonate solution (100 mL) was added. After 1 h the phases were separated and the DCM phase washed with water then brine, dried (Na$_2$SO$_4$) and evaporated affording a brown oil (5.0 g, 92%) with spectroscopic data consistent with ethyl (2S,5R)-6-(benzyloxy)-7-oxo-1,6-diazabicyclo[3.2.1]octane-2-carboxylate and which was used directly without purification.

M/z 305.4 (M+H)$^+$.

b. (2S,5R)-6-(benzyloxy)-2-(hydroxymethyl)-1,6-diazabicyclo[3.2.1]octan-7-one

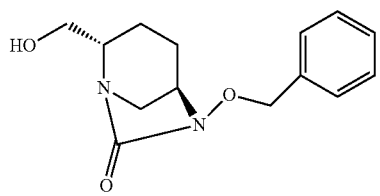 [SMILES: O=C1N2C[C@@H](CC[C@H]2CO)N1OCc1ccccc1]

A solution of the crude ethyl (2S,5R)-6-(benzyloxy)-7-oxo-1,6-diazabicyclo[3.2.1]octane-2-carboxylate (5.0 g, 16.4 mmol) in THF (75 mL) and ethanol (75 mL) was treated at 0° C. with a solution of lithium borohydride in THF (4M; 24 mL, 96 mmol). After 1 h at room temperature, the mixture was recooled to at 0° C. and a further portion of a solution of lithium borohydride in THF (4M; 12 mL, 48 mmol) was added. After a further 16 h at room temperature the mixture was treated with saturated aqueous monopotassium phosphate (200 mL) and the mixture extracted several times with DCM. The combined DCM extracts were washed with water then brine, dried ($Na_2SO_4$) and evaporated affording a brown oil (5 g). This was chromatographed on silica eluting with 0-100% ethyl acetate in hexane affording a colourless oil (2.2 g, 47% over 2 steps).

M/z 263.3 $(M+H)^+$.

c. (2S,5R)-6-(Benzyloxy)-7-oxo-1,6-diazabicyclo[3.2.1]octane-2-carbaldehyde

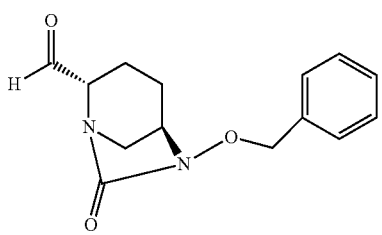 [SMILES: O=C[C@@H]1CC[C@@H]2CN1C(=O)N2OCc1ccccc1]

A solution of (2S,5R)-6-(benzyloxy)-2-(hydroxymethyl)-1,6-diazabicyclo[3.2.1]octan-7-one (1.5 g, 5.7 mmol) in DCM (50 mL) was treated at 0° C. with trichloroisocyanuric acid (1.9 g, 8.6 mmol) and TEMPO (90 mg, 0.6 mmol). The mixture was stirred at 0° C. for 2 h then filtered through celite, washing with DCM. The combined DCM filtrates were washed with saturated aqueous sodium bicarbonate solution, brine, dried ($Na_2SO_4$) and evaporated to afford an oil (1.5 g, 100%) which was used directly in the next step.

M/z 261.4 $(M+H)^+$.

d. (2S,5R)-6-(Benzyloxy)-2-(difluoromethyl)-1,6-diazabicyclo[3.2.1]octan-7-one A solution of (2S,5R)-6-(benzyloxy)-7-oxo-1,6-diazabicyclo[3.2.1]octane-2-carbaldehyde (1.5 g, 5.7 mmol) in DCM (30 mL) at 0° C. was treated with DAST (1.5 mL, 12 mmol). The mixture was stirred at room temperature for 4 hours then solvent was removed by purging with nitrogen. The residue was dissolved in ethyl acetate and added to ice-cold water. The organic phase was separated, washed with saturated aqueous sodium bicarbonate solution, brine, dried ($Na_2SO_4$) and evaporated affording an oil. This was chromatographed on silica eluting with 20% ethyl acetate in hexane affording a yellow oil (0.7 g, 44% over 2 steps).

M/z 283.3 $(M+H)^+$.

e. (2S,5R)-2-(Difluoromethyl)-6-hydroxy-1,6-diazabicyclo[3.2.1]octan-7-one

A solution of (2S,5R)-6-(benzyloxy)-2-(difluoromethyl)-1,6-diazabicyclo[3.2.1]octan-7-one (0.60 g, 2.1 mmol) in methanol (15 mL) was hydrogenated over 10% palladium on charcoal (0.60 g) at 100 p.s.i. in a steel bomb. After 4 h the mixture was filtered through celite, washing with methanol and the combined filtrates were evaporated to give a white solid (0.4 g, 100%) which was used directly in the next step.

M/z 193.3 $(M+H)^+$.

f. Tetrabutylammonium (2S,5R)-2-(difluoromethyl)-7-oxo-1,6-diazabicyclo[3.2.1]octan-6-yl sulfate

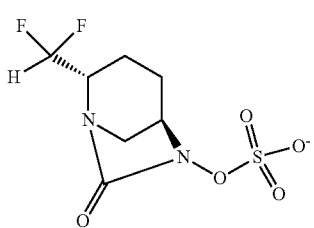

-continued

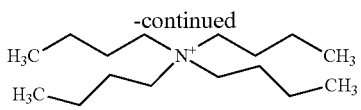

A solution of (2S,5R)-2-(difluoromethyl)-6-hydroxy-1,6-diazabicyclo[3.2.1]octan-7-one (0.40 g, 2.1 mmol) in DCM (30 mL) at 0° C. was treated with TEA (1.1 mL, 8.3 mmol) then sulfur trioxide pyridine complex (0.67 g, 4.2 mmol) was added. After 4 h at room temperature a solution of n-tetrabutylammonium acetate (0.94 g, 3.1 mmol) in water (20 mL) was added. After 2 h further DCM was added and the phases were separated. The DCM phase was washed with water, dried ($Na_2SO_4$) and evaporated. The residue was chromatographed on silica eluting with 0-100% ethyl acetate in hexane followed by 4% methanol in DCM, affording a colourless oil (0.45 g, 42% over 2 steps).

M/z 271.4 (M)⁻.

g. Sodium (2S,5R)-7-oxo-2-(difluoromethyl)-1,6-diazabicyclo[3.2.1]octan-6-yl sulfate A solution of tetrabutylammonnium (2S,5R)-2-(difluoromethyl)-7-oxo-1,6-diazabicyclo[3.2.1]octan-6-yl sulfate (0.45 g, 0.88 mmol) in water (10 mL) was treated with Dowex™ Na resin (1 g). After 1 h the mixture was filtered through a bed of Dowex™ Na resin. The combined filtrates were passed through a second bed of Dowex™ Na resin, washing with water (5 mL) then the combined filtrates were freeze-dried to obtain the title compound as a white solid (202 mg, 78%).

$^1$H NMR (400 MHz, d$_6$-DMSO) δ 6.24 (1H, t, J=4.4 Hz, CHF2), 4.06 (1H, m), 3.40 (1H, m), 3.20 (1H, m), 3.05 (1H, m), 1.95-1.75 (4H, m).

LCMS (ESI [M−Na]⁻) 271.1.

Example 3

Sodium (2S,5R)-2-(dichloromethyl)-7-oxo-1,6-diazabicyclo[3.2.1]octan-6-yl sulfate

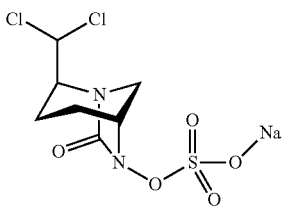

a. (2S,5R)-6-(Benzyloxy)-2-(dichloromethyl)-1,6-diazabicyclo[3.2.1]octan-7-one

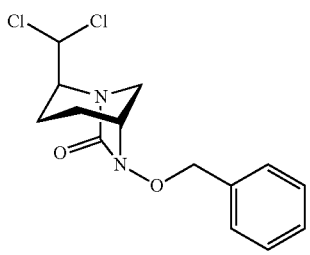

A solution of (2S,5R)-6-(benzyloxy)-7-oxo-1,6-diazabicyclo[3.2.1]octane-2-carbaldehyde (2.2 g, 8.4 mmol) in DCM (100 mL) was treated with phosphorus pentachloride (3.5 g, 16.9 mmol). After 16 h the mixture was diluted with DCM and washed with ice-cold water, brine, dried ($Na_2SO_4$) and evaporated. The residue was chromatographed on silica eluting with 0-20% ethyl acetate giving 3 separate fractions. Fractions 1 and 3 did not contain the desired compound but Fraction 2 (TLC; Rf 0.4 in 20% ethyl acetate/hexane), a white solid (130 mg, 5%), showed spectroscopic data consistent with the desired compound. In particular, HMBC NMR studies showed a close spatial proximity between the carbonyl carbon and the C2-H proton, thereby defining the —CCl2H substituent as axial and the C2-chirality as S, as in the diagram.

M/z 315.4, 317.3 (M+H)⁺.

b. (2S,5R)-2-(Dichloromethyl)-6-hydroxy-1,6-diazabicyclo[3.2.1]octan-7-one

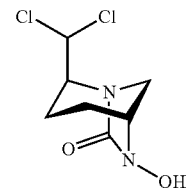

A solution of 6-(benzyloxy)-2-(dichloromethyl)-1,6-diazabicyclo[3.2.1]octan-7-one (130 mg, 0.4 mmol) in methanol (10 ml) was treated with 10% palladium on charcoal (130 mg) and hydrogenated (balloon pressure) for 2 h. The mixture was filtered through celite, washing with methanol. The combined filtrates were evaporated to give an off-white solid (85 mg, 92%) which was used immediately in the next stage.

M/z 225.4; 227.3 (M+H)⁺.

c. Tetrabutylammonnium (2S,5R)-2-(dichloromethyl)-7-oxo-1,6-diazabicyclo[3.2.1]octan-6-yl sulfate

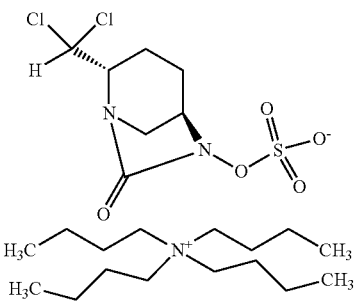

A solution of 2-(dichloromethyl)-6-hydroxy-1,6-diazabicyclo[3.2.1]octan-7-one (85 mg, 0.37 mmol) in DCM (10 mL) was treated at 0° C. with TEA (0.2 mL, 0.8 mmol) and sulfur trioxide pyridine complex (0.12 g, 0.76 mmol). The mixture was stirred at room temperature for 4 h then evaporated to dryness. The residue was redissolved in DMF (2 mL) and treated with TEA (0.4 mL, 1.6 mmol) and more sulfur trioxide pyridine complex (0.12 g, 0.76 mmol). The mixture was stirred at room temperature for 2 h then a solution of n-tetrabutylammonium acetate (0.28 g, 0.8 mmol) in water (10 mL) was added. After 2 h, the mixture was diluted with DCM and the organic extract washed with water then brine, dried (Na$_2$SO$_4$) then evaporated to give an oil. This was chromatographed on silica eluting with 0-100% ethyl acetate in hexane then 6% methanol in DCM to afford a colourless oil (68 mg, 33%).

M/z 304.4, 306.3 (M)$^-$.

d. Sodium (2S,5R)-2-(dichloromethyl)-7-oxo-1,6-diazabicyclo[3.2.1]octan-6-yl sulfate A solution of tetrabutylammonnium (2S,5R)-2-(dichloromethyl)-7-oxo-1,6-diazabicyclo[3.2.1]octan-6-yl sulfate (68 mg, 0.12 mmol) in water (2 mL) and ACN (2 mL) was treated with Dowex™ Na resin (0.5 g). After 1 h the mixture was filtered through a bed of Dowex™ Na resin. The combined filtrates were passed through a second bed of Dowex™ Na resin, washing with water-ACN (1 mL; 1 mL). The filtrates were passed through a second bed of Dowex™ Na resin then the combined filtrates were freeze-dried to obtain the title compound as a white solid (36 mg, 88%).

$^1$H NMR (400 MHz, d$_6$-DMSO) δ 6.25 (1H, d, J=0.8 Hz, CHCl2), 4.02 (1H, m), 3.45 (1H, m), 3.22 (1H, d), 2.95 (1H, m), 1.95-1.75 (4H, m).

LCMS (ESI [M−Na]$^-$) 303.4, 305.4.

Example 4

Sodium (2S, 5R)-2-(fluoromethyl)-7-oxo-1,6-diazabicyclo[3.2.1]octan-6-yl sulphate

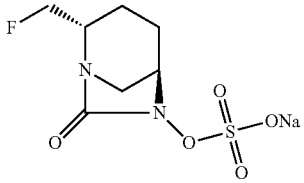

Example 4 was prepared from the key intermediate alcohol by conversion to the fluoromethyl substituent using standard DAST treatment (see for example Collet, C. et al, Bioorg. Med. Chem. Lett. 2017, 25, 5603).

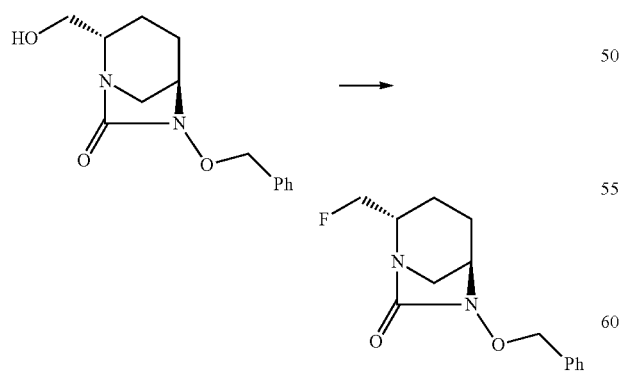

The remainder of the synthesis (debenzylation, sulfonation and sodium salt formation) followed the procedures set out above.

M/z=253.0 (M−Na)$^-$.

1H NMR (500 MHz, d6-DMSO) δ 4.71-4.48 (2H, m, CH$_2$F2), 3.98 (1H, m), 3.42 (1H, m), 3.19 (1H, m), 2.92 (1H, m), 1.84 (1H, m), 1.78-1.66 (2H, m), 1.51 (1H, m).

Example 5

Sodium (2S, 5R)-2-(1,1-difluoroethyl)-7-oxo-1,6-diazabicyclo[3.2.1]octan-6-yl sulphate

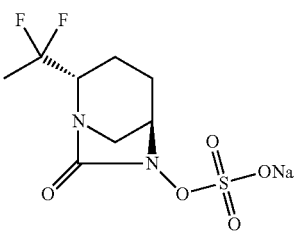

Example 5 was prepared by conversion of the acid to the Weinreb amide, methyl ketone formation using methyl magnesium bromide then conversion of the methyl ketone to the difluoroethyl substituent using DAST (Wityak, J., et al, J. Medicinal Chemistry, 2015, 58, 2967).

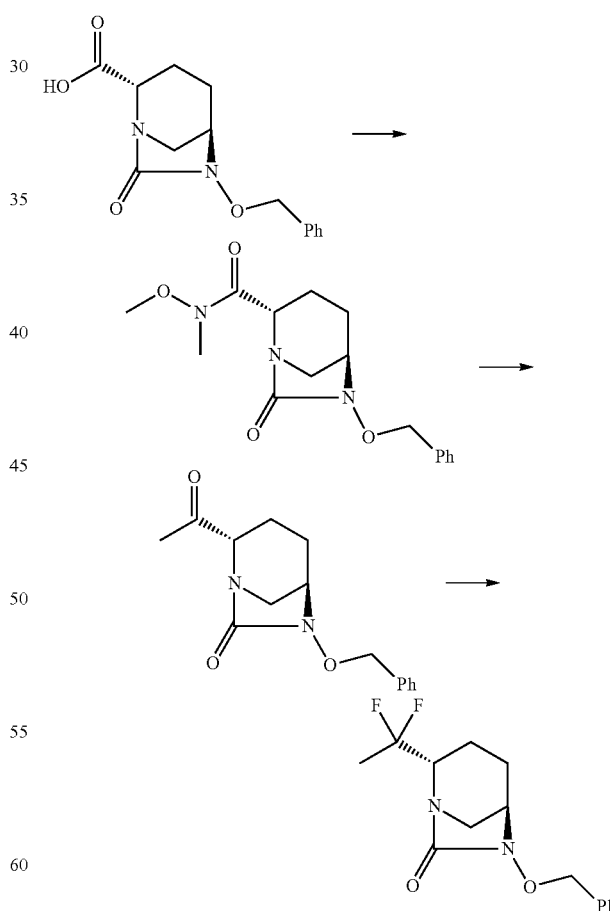

The remainder of the synthesis (debenzylation, sulfonation and sodium salt formation) followed the procedures set out above.

M/z=285.0 (M−Na)$^-$.

1H NMR (500 MHz, d6-DMSO) δ 4.02 (1H, m), 3.40 (1H, m), 3.18 (1H, m), 3.02 (1H, m), 1.89-1.79 (2H, m), 1.78-1.65 (2H, m), 1.72 (3H, m), 1.51 (1H, m).

Example 6

Sodium (2S, 5R)-2-(chloromethyl)-7-oxo-1,6-diazabicyclo[3.2.1]octan-6-yl sulphate

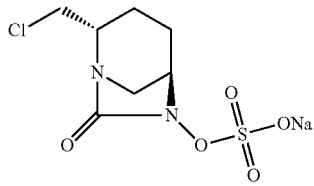

Example 6 was prepared by reaction of the alcohol with methane sulfonyl chloride in the presence of triethylamine to give the corresponding mesylate then displacement using tetra-n-butyl ammonium chloride to afford the chloromethyl intermediate.

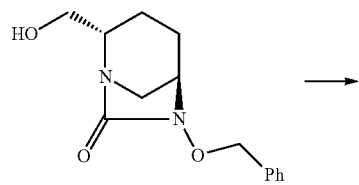

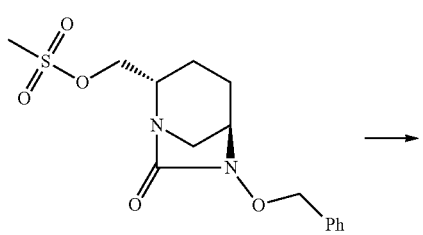

The remainder of the synthesis (debenzylation, sulfonation and sodium salt formation) followed the procedures set out above.

M/z=268.8 (M−Na)⁻.

1H NMR (500 MHz, d6-DMSO) δ 3.99 (1H, m), 3.88 (1H, m), 3.81 (1H, m), 3.32 (1H, m), 3.19 (1H, m), 2.89 (1H, m), 1.83-1.69 (3H, m), 1.52 (1H, m).

Example 7

Sodium (2R, 5R)-7-oxo-2-[(trifluoromethyl)sulfanyl]-1,6-diazabicyclo[3.2.1]octan-6-yl sulphate

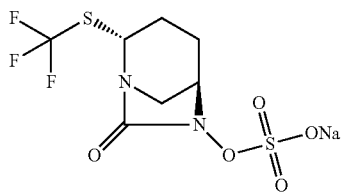

Example 7 was prepared by a decarboxylative approach, using related methodology to that for introducing halogens but using silver(I) trifluoromethanethiolate following the conditions described by Liu, C. et al (RSC Advances, 2017, 7, 880).

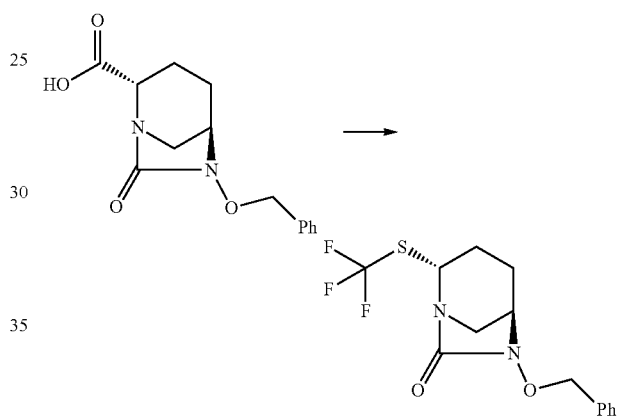

The remainder of the synthesis (debenzylation, sulfonation and sodium salt formation) followed the procedures set out above with the variation that the benzyl group was removed using titanium tetrachloride as hydrogenation was unsuccessful.

M/z=320.9 (M−Na)⁻.

1H NMR (500 MHz, d6-DMSO) δ 5.04 (1H, dd, J=12.5 Hz, J=4.5 Hz, CHSCF3), 4.01 (1H, d, J=3.0 Hz), 3.23 (2H, m), 2.01 (2H, m), 1.89-1.72 (2H, m).

Example 8

Sodium (2S, 5R)-7-oxo-2-[(trifluoromethoxy)methyl]-1,6-diazabicyclo[3.2.1]octan-6-yl sulphate

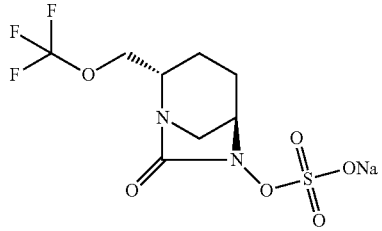

Example 8 was prepared by trifluoromethylation of the alcohol using trifluoromethyltrimethylsilane (TMSCF₃) using silver(I)triflate and Selectfluor according to the conditions of Liu, J.-B. et al (Organic Letters, 2017, 17, 5048).

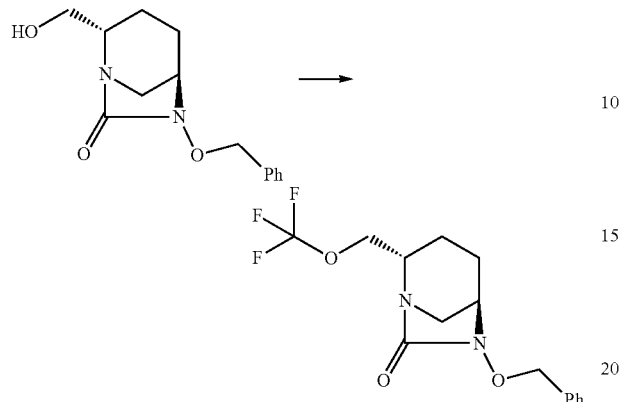

The remainder of the synthesis (debenzylation, sulfonation and sodium salt formation) followed the procedures set out above.

M/z=318.9 (M−Na)⁻.

1H NMR (500 MHz, d6-DMSO) δ 4.32 (1H, dd, J=10.5 Hz, J=9.5 Hz), 4.16 (1H, dd, J=10.5 Hz, J=5.5 Hz), 3.98 (1H, d, J=3 Hz), 3.45 (1H, m), 3.21 (1H, m), 2.91 (1H, m), 1.85-1.69 (3H, m), 1.48 (1H, m).

Example 9

Sodium (2S, 5R)-2-[difluoro(1,3-thiazol-2-yl)methyl]-7-oxo-1,6-diazabicyclo[3.2.1]octan-6-yl sulphate

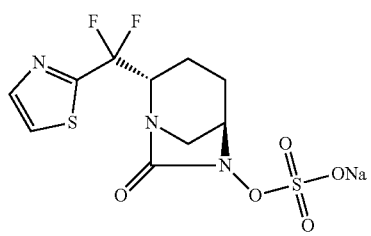

Example 9 was prepared from the aldehyde which was transformed into the thiazolyl ketone following the methodology as described by Dondoni, A., et al, (2004, Journal of Organic Chemistry, 69, 5023), namely in situ generation of the thiazole anion and reaction with the aldehyde; trapping with acetic anhydride to give the acetate; hydrolysis of the acetate followed by a Swern-like oxidation to generate the ketone. This was reacted with DAST in the usual way to generate the geminal difluoride.

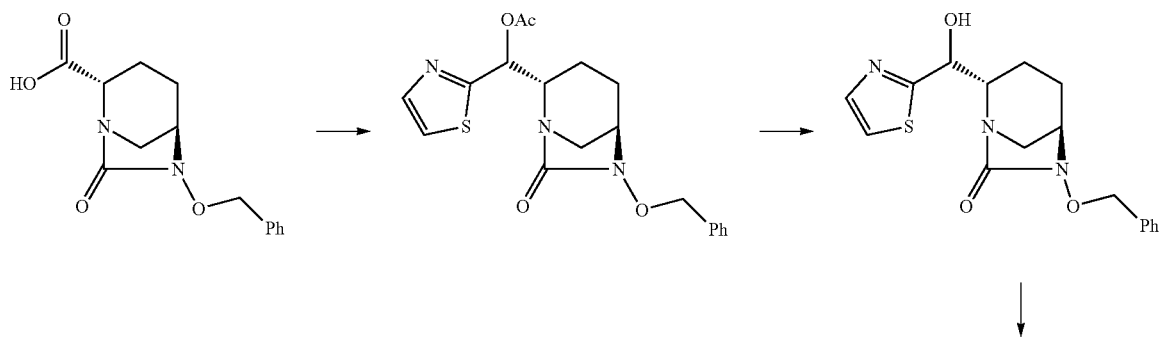

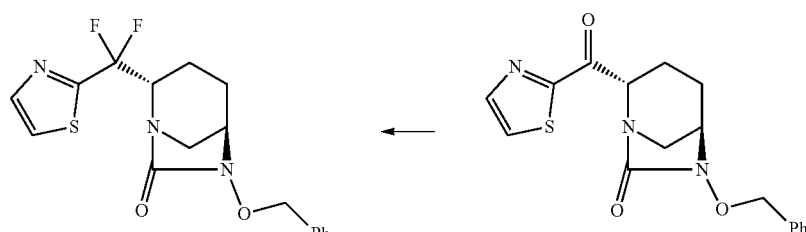

The remainder of the synthesis (debenzylation, sulfonation and sodium salt formation) followed the procedures set out above with the variation that the benzyl group was removed using titanium tetrachloride as hydrogenation was unsuccessful.

M/z=353.9 (M−Na)⁻.

1H NMR (500 MHz, d6-DMSO) δ 8.04 (2H, s), 4.05-3.97 (2H, m), 3.24 (1H, m), 3.01 (1H, m), 2.03-1.98 (1H, m), 1.88-1.77 (3H, m).

Example 10

Sodium (2R,5R)-2-fluoro-7-oxo-1,6-diazabicyclo[3.2.1]octan-6-yl sulfate

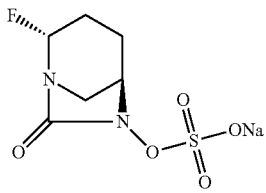

a. (2S,5R)-6-(benzyloxy)-7-oxo-1,6-diazabicyclo[3.2.1]octane-2-carboxylic acid

To a solution of commercially-available ethyl (2S,5R)-6-(benzyloxy)-7-oxo-1,6-diazabicyclo[3.2.1]octane-2-carboxylate (7.0 g, 23.0 mmol) in acetone:water (1:1, 120 mL) was added LiOH·H₂O (0.97 g, 23.0 mmol) at 0° C. The resulting reaction mixture was stirred at room temperature for 2 h. Then the reaction mixture was diluted with water (50 mL) and washed with EtOAc (2×100 mL). The aqueous layer was acidified with 1N HCl (to pH ~3) and then extracted with EtOAc (2×100 mL). The combined organic phases were washed with water, brine, dried over anhydrous Na₂SO₄, filtered and concentrated to obtain (2S,5R)-6-(benzyloxy)-7-oxo-1,6-diazabicyclo[3.2.1]octane-2-carboxylic acid (5 g, 79%) as a white solid which was used in the next step without purification.

M/z=277.1 (M+H)⁺.

b. (2R,5R)-6-(benzyloxy)-2-fluoro-1,6-diazabicyclo[3.2.1]octan-7-one (A) and (2S,5R)-6-(benzyloxy)-2-fluoro-1,6-diazabicyclo[3.2.1]octan-7-one (B)

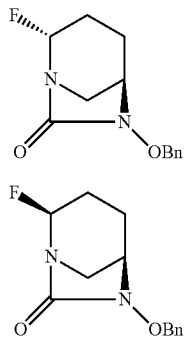

To a stirred solution of (2S,5R)-6-(benzyloxy)-7-oxo-1,6-diazabicyclo [3.2.1] octane-2-carboxylic acid (2.5 g, 9.04 mmol) in acetone:water (4:1, 100 mL) was added Selectfluor™ (6.4 g, 18.0 mmol) and AgNO₃ (153 mg, 0.90 mmol) at room temperature. The resulting reaction mixture was heated at 50° C. for 3 h then evaporated. The resulting residue was treated with EtOAc (100 mL), filtered through a celite pad and washing the pad with EtOAc (10 mL). The filtrate was washed with NaHCO₃ solution (50 mL), water (50 mL) and brine (50 mL). The organic layer was dried over anhydrous Na₂SO₄, filtered and concentrated to obtain an oil. This was chromatographed on silica gel eluting with 10% EtOAc in hexane as eluent affording (2R,5R)-6-(benzyloxy)-2-fluoro-1,6-diazabicyclo[3.2.1]octan-7-one (A) (550 mg, 24%) as a pale yellow viscous oil. Further elution with 50-60% EtOAc in hexane afforded (2S,5R)-6-(benzyloxy)-2-fluoro-1,6-diazabicyclo[3.2.1]octan-7-one (B) (300 mg, 13%) as a pale yellow solid.

(2R,5R)-6-(benzyloxy)-2-fluoro-1,6-diazabicyclo[3.2.1]octan-7-one (A)

M/z=251.1 (M+H)⁺.

NMR experiments showed coupling constants for the H atom on the same carbon as the F atom of 45.0 Hz (coupling to F) and 4.5 Hz (coupling to the axial proton on the adjacent carbon) thereby establishing that this H atom has an equatorial disposition and the molecule has the stereochemistry as shown.

(2S,5R)-6-(benzyloxy)-2-fluoro-1,6-diazabicyclo[3.2.1]octan-7-one (B)

M/z=251.1 (M+H)⁺.

NMR experiments showed coupling constants for the H atom on the same carbon as the F atom of 44.0 Hz (coupling to F) and 10.5 Hz (coupling to the axial proton on the adjacent carbon) thereby establishing that this H atom has an axial disposition and the molecule has the stereochemistry as shown.

c. (2R,5R)-2-fluoro-6-hydroxy-1,6-diazabicyclo[3.2.1]octan-7-one

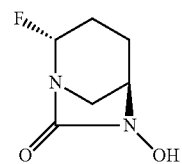 [SMILES: O=C1N(O)[C@@H]2CC[C@@H](F)N1C2]

To a solution of (2R,5R)-6-(benzyloxy)-2-fluoro-1,6-diazabicyclo[3.2.1]octan-7-one (300 mg, 1.19 mmol) in methanol (30 mL) was added 10% Pd/C (300 mg). The reaction mixture was hydrogenated at room temperature for 1 h using hydrogen balloon pressure. The reaction mixture was filtered through a celite pad washing with methanol (10 mL). The filtrate was evaporated to give (2R,5R)-2-fluoro-6-hydroxy-1,6-diazabicyclo[3.2.1]octan-7-one (180 mg, 94%) as an off-white solid which was used in the next step without purification.

M/z=161.0 (M+H)⁺.

d. Tetrabutylammonium (2R,5R)-2-fluoro-7-oxo-1,6-diazabicyclo[3.2.1]octan-6-yl sulphate

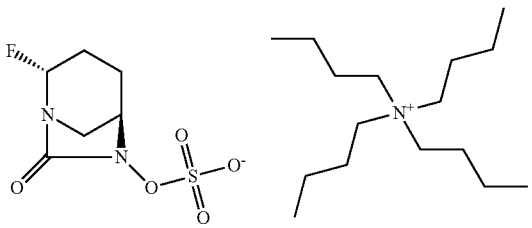 [SMILES: O=C1N2C[C@@H](CC[C@H]2F)N1OS(=O)(=O)[O-] ; CCCC[N+](CCCC)(CCCC)CCCC]

To a solution of (2R,5R)-2-fluoro-6-hydroxy-1,6-diazabicyclo[3.2.1]octan-7-one (180 mg, 1.12 mmol) in DCM (20 mL) was added TEA (1.5 mL, 11.2 mmol) followed by SO$_3$:Py complex (1.07 g, 6.74 mmol) at 0° C. and stirred at room temperature for 4 h. Then a solution of n-tetrabutylammonium acetate (2.7 g, 8.99 mmol) in water (20 mL) was added and stirred at room temperature for 2 h. The reaction mixture was diluted with DCM (50 mL) and the organic layer was separated. The organic layer was washed with water (5×25 mL), dried over Na$_2$SO$_4$, filtered and evaporated. The resulting residue was chromatographed on silica eluting with 0-100% ethyl acetate in hexane followed by 5% methanol in DCM affording tetrabutylammonium (2R,5R)-2-fluoro-7-oxo-1,6-diazabicyclo[3.2.1]octan-6-yl sulfate (220 mg, 40% over 2 steps) as a colourless oil.

M/z=239.0 (M−nBu$_4$)$^−$.

(a) Sodium (2R,5R)-2-fluoro-7-oxo-1,6-diazabicyclo[3.2.1]octan-6-yl sulphate A stirred solution tetrabutylammonium (2R,5R)-2-fluoro-7-oxo-1,6-diazabicyclo[3.2.1]octan-6-yl sulfate (220 mg, 0.45 mmol) in water (10 mL) was treated with Dowex™ Na resin (1 g). After 1 h the mixture was filtered through a pad of Dowex™ Na resin, washing with H$_2$O (5 mL). The combined filtrate was again treated with Dowex™ Na resin (1 g) for 1 h, filtered through a bed of Dowex™ Na resin, washing with H$_2$O (5 mL). This process was repeated for another 3 times. The combined filtrates were freeze-dried to obtain the title compound (90 mg, 75%) as an off-white solid.

M/z=239.0 (M−Na)$^−$.

$^1$H NMR (500 MHz, d$_6$-DMSO) δ 5.35 (1H, ddd, J=46 Hz, 5 Hz, 2.5 Hz, CHF), 4.08-4.06 (1H, m), 3.26-3.24 (1H, m), 3.06-3.04 (1H, m), 1.99-1.68 (4H, m).

Example 11

Sodium (2S, 5R)-2-fluoro-7-oxo-1,6-diazabicyclo[3.2.1] octan-6-yl sulfate

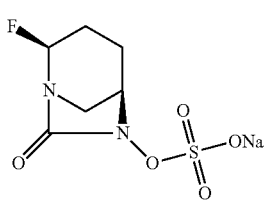

a. (2S,5R)-2-fluoro-6-hydroxy-1,6-diazabicyclo[3.2.1]octan-7-one

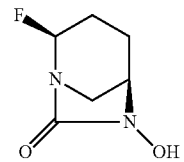

To a solution of (2S,5R)-6-(benzyloxy)-2-fluoro-1,6-diazabicyclo[3.2.1]octan-7-one (250 mg, 0.99 mmol) (See (B) from Example 10) in methanol (10 mL) was added 10% Pd/C (250 mg). The reaction mixture was hydrogenated at room temperature for 1 h using hydrogen balloon pressure. The reaction mixture was filtered through a celite pad and the pad was washed with methanol (5 mL). The filtrate was evaporated to give (2S,5R)-2-fluoro-6-hydroxy-1,6-diazabicyclo[3.2.1]octan-7-one (130 mg, 81%) as an off-white solid which was used in the next step without purification.

M/z=161.1 (M+H)$^+$.

b. Tetrabutylammonium (2S,5R)-2-fluoro-7-oxo-1,6-diazabicyclo[3.2.1]octan-6-yl sulfate

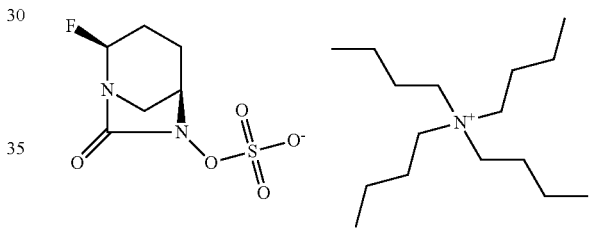

To a solution of (2S,5R)-2-fluoro-6-hydroxy-1,6-diazabicyclo[3.2.1]octan-7-one (130 mg, 0.81 mmol) in DCM (30 mL) was added TEA (1.14 mL, 8.11 mmol) followed by SO$_3$·Py complex (775 mg, 4.87 mmol) at 0° C. The mixture was stirred at room temperature for 4 h. A solution of n-tetrabutylammonium acetate (1.9 g, 6.49 mmol) in water (30 mL) was added and the mixture stirred at room temperature for 2 h. The reaction mixture was diluted with DCM (50 mL) and the organic layer was separated. The DCM layer was washed with water (5×25 mL), dried over Na$_2$SO$_4$, filtered and evaporated. The resulting residue was chromatographed on silica eluting with 0-100% EtOAc in hexane followed by 5% methanol in DCM affording tetrabutylammonium (2S,5R)-2-fluoro-7-oxo-1,6-diazabicyclo[3.2.1]octan-6-yl sulfate (60 mg, 15% over 2 steps) as a colourless oil.

M/z=239.1 (M−nBu$_4$)$^−$.

c. Sodium (2S,5R)-2-fluoro-7-oxo-1,6-diazabicyclo[3.2.1]octan-6-yl sulfate

A stirred solution of tetrabutylammonium (2R,5R)-2-fluoro-7-oxo-1,6-diazabicyclo[3.2.1]octan-6-yl sulfate (60 mg, 0.12 mmol) in CH$_3$CN:H$_2$O (1:1, 4 mL) was treated with Dowex™ Na resin (1 g). After 1 h the mixture was filtered through a bed of Dowex™ Na resin and washed with CH$_3$CN:H$_2$O (1:1, 2 mL). The combined filtrate was again treated with Dowex™ Na resin (1 g) for 30 min, filtered through a bed of Dowex™ Na resin and washed with CH₃CN:H₂O (1:1, 2 mL). This process was repeated for another 3 times. The combined filtrates were freeze-dried to obtain the title compound as an off-white solid.

M/z=238.9 (M−Na)⁻.

¹H NMR (500 MHz, d₆-DMSO) δ 5.27 (1H, ddd, J=44 Hz, J=10.5 Hz, J=4.5 Hz, CHF), 3.96-3.94 (1H, m), 3.24-3.21 (1H, m), 3.01 (1H, J=12 Hz), 2.06-2.01 (2H, m), 1.73-1.67 (1H, m), 1.61-1.57 (1H, m).

Example 12

Sodium (2R,5R)-2-chloro-7-oxo-1,6-diazabicyclo[3.2.1]octan-6-yl sulfate

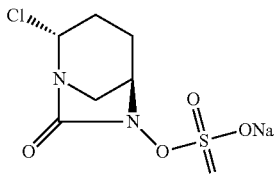

a. (2R,5R)-6-(benzyloxy)-2-chloro-1,6-diazabicyclo[3.2.1]octan-7-one

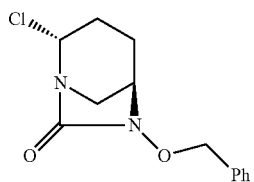 [SMILES: O=C1N2C[C@@H](CC[C@H]2Cl)N1OCc1ccccc1]

To a solution of (2S,5R)-6-(benzyloxy)-7-oxo-1,6-diazabicyclo[3.2.1]octane-2-carboxylic acid (1 g, 3.62 mmol) in DMF (20 mL) and AcOH (4 mL) was added N-chlorosuccinimide (4.83 g, 36.2 mmol) at room temperature. The reaction mixture was purged with nitrogen gas for 5 minutes. Then Pb(OAc)₄ (2.4 g, 5.43 mmol) was added and the reaction mixture was purged with nitrogen gas for further 5 minutes. The reaction was heated at 60° C. for 4 h and then treated with saturated K₂CO₃ at room temperature. The mixture was extracted with diethyl ether (2×50 mL), the combined organic layer was washed with brine (20 mL), dried over anhydrous Na₂SO₄, filtered and concentrated to obtain the crude product. This was chromatographed on silica eluting with 10% EtOAc in hexane as eluent affording (2R,5R)-6-(benzyloxy)-2-chloro-1,6-diazabicyclo[3.2.1]octan-7-one (270 mg, 28%) as a light yellow oil.

M/z=267.0 (M+H)⁺.

NMR experiments showed coupling constants for the H atom on the same carbon as the C₁ of 5.5 Hz (coupling to the axial proton on the adjacent carbon) thereby establishing that this H atom has an equatorial disposition and the molecule has the stereochemistry as shown.

b. (2R,5R)-2-chloro-6-hydroxy-1,6-diazabicyclo[3.2.1]octan-7-one

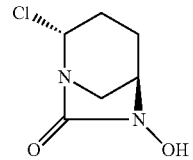 [SMILES: O=C1N(O)[C@@H]2CC[C@@H](Cl)N1C2]

To a solution of (2R,5R)-6-(benzyloxy)-2-chloro-1,6-diazabicyclo[3.2.1]octan-7-one (220 mg, 0.824 mmol) in methanol (20 mL) was added 10% Pd/C (220 mg). The reaction mixture was hydrogenated at room temperature for 1 h using hydrogen balloon pressure. The reaction mixture was filtered through a celite pad and the pad was washed with methanol (10 mL). The filtrate was evaporated to afford (2R,5R)-2-chloro-6-hydroxy-1,6-diazabicyclo[3.2.1]octan-7-one (150 mg) as an off-white solid which was used without purification.

M/z=177.0 (M+H)⁺.

c. Tetrabutylammonium (2R,5R)-2-chloro-7-oxo-1,6-diazabicyclo [3.2.1] octan-6-yl sulphate

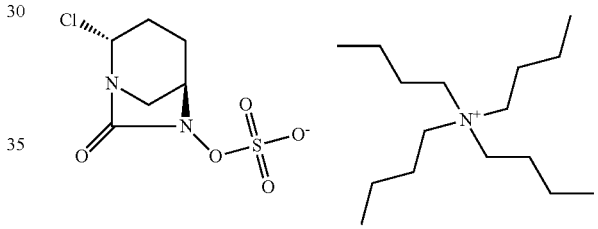

To a stirred solution of (2R,5R)-2-chloro-6-hydroxy-1,6-diazabicyclo[3.2.1]octan-7-one (150 mg, 0.849 mmol) in DCM (20 mL) was added TEA (1.8 mL, 12.7 mmol) followed by SO₃:Py complex (1.35 g, 8.49 mmol) at 0° C. and stirred at room temperature for 3 h. Then a solution of tetra(n-butyl)ammonium acetate (2.56 g, 8.49 mmol) in water (20 mL) was added and stirred at room temperature for 3 h. The reaction mixture was diluted with DCM (50 mL) and the phases were separated. The organic extract was washed with water (5×25 mL), dried over Na₂SO₄, filtered and evaporated. The residue was chromatographed on silica eluting with 0-100% ethyl acetate in hexane followed by 5% methanol in DCM to afford tetrabutylammonium (2R,5R)-2-chloro-7-oxo-1,6-diazabicyclo [3.2.1] octan-6-yl sulphate (130 mg, 30% over 2 steps) as a colourless oil.

M/z=254.9 (M−nBu₄)⁻.

d. Sodium (2R,5R)-2-chloro-7-oxo-1,6-diazabicyclo [3.2.1] octan-6-yl sulphate

A solution of tetrabutylammonium (2R,5R)-2-chloro-7-oxo-1,6-diazabicyclo [3.2.1] octan-6-yl sulphate (130 mg, 0.26 mmol) in CH₃CN:H₂O (1:1, 3 mL) was treated with Dowex™ Na resin (1 g). After 30 min., the mixture was filtered through a bed of Dowex™ Na resin and washed with CH₃CN:H₂O (1:1, 1 mL). The combined filtrate was again treated with Dowex™ Na resin (1 g) for 30 min, filtered through a bed of Dowex™ Na resin and washed with CH₃CN:H₂O (1:1, 1 mL). This process was repeated for another 3 times. The combined filtrates were freeze-dried and the resulting compound was purified by preparative HPLC [X-SELECT-C18 (150*19), 5 u, Mobile phase: H₂O: MeCN]. The collected fractions were freeze-dried to afford the title compound (5.0 mg, 7%) as an off-white solid.

M/z=255.0 (M–Na)⁻.

¹H NMR (500 MHz, d₆-DMSO) δ 5.51 (1H, dd, J=6.0 Hz, J=2.0 Hz, CHCl), 4.10 (1H, J=3.0 Hz), 3.51-3.49 (1H, m), 3.07-3.05 (1H, m), 2.26-2.18 (1H, m), 1.94-1.80 (3H, m).

Biological Activity

Experiments were conducted to determine:
(1) The inhibitory activity of the compounds of the invention against Serine β-lactamase enzymes from different classes;
(2) β-lactam potentiation by the compounds against strains expressing SBL enzymes Details of the protocols used for each of the sets of experiments are set out below:

Enzymatic Inhibition

In Vitro Enzyme Inhibition Assays

Enzyme inhibition assays were performed using purified SBL enzymes from *Enterobacter cloacae* (such as TEM-1; AmpC; CTX-M15; KPC-2; OXA-48) in 10 mM HEPES buffer pH 7.5 in 96-well microtiter plates. Nitrocefin (100 μM for TEM-1, AmpC, KPC-2, OXA-48; and 50 μM for CTX-M15) was used as substrate. Its hydrolysis was followed, after an initial 10 min incubation at 30° C., at 482 nm during 12 mn every 30 seconds using a Perkin Elmer Envision UV fluorescence plate reader. Hydrolysis rate data in presence of a range of inhibitors was analysed and IC₅₀ determined for each compound using Dotmatics database software.

Compound dilution was performed in DMSO.

Mean IC50 results are shown below for enzymatic inhibition of a selected panel of SBL enzymes. Data are banded together in the following manner:

*TEM*-1: *IC*50 < 3 nM (*A*); 3–10 nM (*B*); >10 nM (*C*).

*KPC*-2: *IC*50 < 10 nM (*A*); >10 nM (*B*).

*AmpC*: *IC*50 < 10 nM (*A*); 10–40 nM (*B*); 40–60 nM (*C*);

>60 nM (*D*).

*OXA*-48: *IC*50 < 20 nM (*A*); 20–100 nM (*B*); 100–200 nM (*C*);

200–300 nM (*D*); >300 nM (*E*).

*CTX*-M15: *IC*50 < 5 nM (*A*); 5–20 nM (*B*); 20–10 nM (*C*);

100–200 nM (*D*).

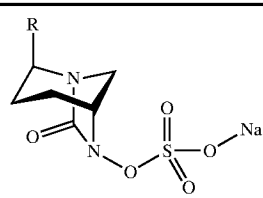

| Compound | R substituent | KPC-2 | Amp-C | OXA-48 | CTX-M15 |
|---|---|---|---|---|---|
| Avibactam | CONH₂ | 7.8 (A) | 8.0 (A) | 296.6 (D) | 1.4 (A) |
| Example 1 | CF₃ | (A) | (A) | (A) | (B) |
| Example 2 | CHF₂ | (A) | (B) | (B) | (B) |

-continued

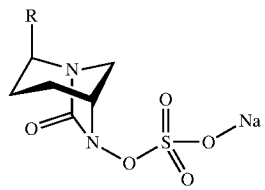

| Compound | R substituent | KPC-2 | Amp-C | OXA-48 | CTX-M15 |
|---|---|---|---|---|---|
| Example 3 | CHCl₂ | (A) | (C) | (C) | (C) |
| Example 4 | CH₂F | (B) | (A) | (D) | (B) |
| Example 5 | CF₂CH₃ | (B) | (C) | (B) | (B) |
| Example 6 | CH₂Cl | (B) | (B) | (D) | N/D |
| Example 7 | CF₃S | (B) | (C) | (D) | N/D |
| Example 8 | CH₂OCF₃ | (A) | (C) | (D) | (D) |
| Example 9 | CF₂-2-thiazolyl | (A) | (A) | (D) | (C) |
| Example 10 | F (R) | (B) | (B) | (D) | N/D |
| Example 11 | F (S) | (B) | (D) | (E) | N/D |
| Example 12 | Cl | (B) | (A) | (E) | N/D |

N/D = not determined

| Compound | R substituent | TEM-1 |
|---|---|---|
| Avibactam | CONH₂ | 4.7 (B) |
| Example 10 | F (R) | (A) |
| Example 11 | F (S) | (C) |
| Example 12 | Cl | (A) |

Antimicrobial Susceptibility Testing

Antibiotic Activity of a β-Lactam Antibiotic on SBL/ESBL Expressing Bacteria in the Presence of the Compounds of the Invention The experiments were carried out using the 'broth microdilution method' according to the protocols M07-A8 established by the Clinical Laboratory Standards Institute (CLSI). Serial dilutions of the β-lactam antibiotic Meropenem were prepared in 96-well plates in cation-adjusted Mueller-Hinton broth (CAMHB); the concentration range was defined from 0.03 mg/L to 512 mg/L. A bacterial inoculum of each strain (clinical isolates) was adjusted to a 0.5 McFarland turbidity standard in physiologic serum (0.9% NaCl), then diluted 1:100 in CAMHB and added to each well to give a final bacterial cell number of 5×10⁵ CFU/well. After incubation for 18-20 hours in a heating chamber at 37° C., the growth inhibition was evaluated by the absence of any bacterial development.

Minimal inhibitory concentrations (MICs) are taken as the lowest concentration of antibiotic at which the test organism did not show visible growth; results were confirmed by measuring the optical density (OD) at 600 nm in a spectrophotometer.

Compounds of the invention were tested at concentrations of 4 μg/mL. The clinical strains used in these Meropenem potentiation experiments were NTBC091.1 (*E. coli* strain expressing KPC-2, TEM-1); NTBC093 (*E. cloacae* strain expressing KPC-2, TEM-1); NTBC096.1 (*K. pneumoniae* strain expressing OXA-181 and SHV-11); NTBC099 (*K. pneumoniae* strain expressing KPC-3, SHV-11 and TEM-1); NTBC189 (*K. pneumoniae* strain expressing TEM-OSBL (b), CTX-M-14, OXA-48 (c)).

| Strain number | β-Lactamase enzyme(s) | Classification | MIC mero, µg/mL, no inhibitor | MIC mero + 4 µg/mL Example1 | MIC mero + 4 µg/mL Example2 |
|---|---|---|---|---|---|
| NTBC091.1 | KPC-2 + TEM-1 | E. coli | 4 | 0.03 | 0.03 |
| NTBC093 | KPC-2 + TEM-1 | E. cloacae | 8 | 0.06 | 0.06 |
| NTBC096.1 | OXA-181 + SHV-11 | K. pneumo | 32 | 4 | 4 |
| NTBC099 | KPC-3 + SHV-11 + TEM-1 | K. pneumo | 256 | 2 | 1 |
| NTBC189 | TEM-OSBL(b) + CTX-M + OXA-48(c) | K. pneumo | 32 | 2 | 2 |

Data for further compounds according to the invention are shown in the following table. In this table, data are banded as follows (Data for Examples 1 and 2 are provided for ease of reference):

$$MIC < 1 \ \mu g/mL \ (A); MIC = 1 \ or \ 2 \ \mu g/mL \ (B); MIC = 4 \ \mu g/mL \ (C);$$

$$MIC = 8 \ \mu g/mL \ (D); MIC > 8 \ \mu g/mL \ (E).$$

| Strain number | β-Lactamase enzyme(s) | MIC mero, µg/mL no inhibitor | MIC mero + 4 µg/mL Avibactam | MIC mero + 4 µg/mL Example 1 | MIC mero + 4 µg/mL Example 2 | MIC mero + 4 µg/mL Example 3 | MIC mero + 4 µg/mL Example 4 | MIC mero + 4 µg/mL Example 5 |
|---|---|---|---|---|---|---|---|---|
| NTBC091.1 | KPC-2 + TEM-1 | 4 | 0.06 (A) | (A) | (A) | (A) | (A) | (A) |
| NTBC093 | KPC-2 + TEM-1 | 8 | 0.03 (A) | (A) | (A) | (A) | (A) | (A) |
| NTBC096.1 | OXA-181 + SHV-11 | 32 | 1 (B) | (C) | (C) | (E) | (B) | (E) |
| NTBC099 | KPC-3 + SHV-11 + TEM-1 | 256 | 0.25 (A) | (B) | (B) | (B) | (B) | (B) |
| NTBC189 | TEM-OSBL(b) + CTX-M + OXA-48(c) | 32 | 0.25 (A) | (B) | (B) | N/D | N/D | N/D |

| Strain number | β-Lactamase enzyme(s) | MIC mero + 4 µg/mL Example 6 | MIC mero + 4 µg/mL Example 7 | MIC mero + 4 µg/mL Example 8 | MIC mero + 4 µg/mL Example 9 | MIC mero + 4 µg/mL Example 10 | MIC mero + 4 µg/mL Example 11 | MIC mero + 4 µg/mL Example 12 |
|---|---|---|---|---|---|---|---|---|
| NTBC091.1 | KPC-2 + TEM-1 | (A) | (A) | (A) | (A) | (A) | (A) | (A) |
| NTBC093 | KPC-2 + TEM-1 | (A) | (B) | (A) | (A) | (A) | (B) | (A) |
| NTBC096.1 | OXA-181 + SHV-11 | (E) | (E) | (E) | (E) | (A) | (D) | (D) |
| NTBC099 | KPC-3 + SHV-11 + TEM-1 | (B) | (E) | (E) | (D) | (B) | (E) | (E) |
| NTBC189 | TEM-OSBL(b) + CTX-M + OXA-48(c) | N/D | N/D | N/D | (A) | (A) | (C) | (C) |

| Strain number | β-Lactamase enzyme(s) | MIC mero, µg/mL no inhibitor | MIC mero + 4 µg/mL Avibactam | MIC mero + 4 µg/mL Example 1 | MIC mero + 4 µg/mL Example 2 | MIC mero + 4 µg/mL Example 3 | MIC mero + 4 µg/mL Example 4 | MIC mero + 4 µg/mL Example 5 |
|---|---|---|---|---|---|---|---|---|
| NTBC091.1 | KPC-2 + TEM-1 | 4 | 0.06 (A) | (A) | (A) | (A) | (A) | (A) |
| NTBC093 | KPC-2 + TEM-1 | 8 | 0.03 (A) | (A) | (A) | (A) | (A) | (A) |
| NTBC096.1 | OXA-181 + SHV-11 | 32 | 1 (B) | (C) | (C) | (E) | (B) | (E) |
| NTBC099 | KPC-3 + SHV-11 + TEM-1 | 256 | 0.25 (A) | (B) | (B) | (B) | (B) | (B) |
| NTBC189 | TEM-OSBL(b) + CTX-M + OXA-48(c) | 32 | 0.25 (A) | (B) | (B) | N/D | N/D | N/D |

| Strain number | β-Lactamase enzyme(s) | MIC mero + 4 µg/mL Example 6 | MIC mero + 4 µg/mL Example 7 | MIC mero + 4 µg/mL Example 8 | MIC mero + 4 µg/mL Example 9 | MIC mero + 4 µg/mL Example 10 | MIC mero + 4 µg/mL Example 11 | MIC mero + 4 µg/mL Example 12 |
|---|---|---|---|---|---|---|---|---|
| NTBC091.1 | KPC-2 + TEM-1 | (A) | (A) | (A) | (A) | (A) | (A) | (A) |
| NTBC093 | KPC-2 + TEM-1 | (A) | (B) | (A) | (A) | (A) | (B) | (A) |
| NTBC096.1 | OXA-181 + SHV-11 | (E) | (E) | (E) | (E) | (A) | (D) | (D) |

| | | | | | | | | |
|---|---|---|---|---|---|---|---|---|
| NTBC099 | KPC-3 + SHV-11 + TEM-1 | (B) | (E) | (E) | (D) | (B) | (E) | (E) |
| NTBC189 | TEM-OSBL(b) + CTX-M + OXA-48(c) | N/D | N/D | N/D | N/D | (A) | (C) | (C) |

Compounds of the invention are highly active. For example, the combination of meropenem and the compound of Example 1 has an MIC lower than the combination of meropenem and avibactam against strain NTBC091.1. The combination of meropenem and the compound of Example 2 has an MIC lower than the combination of meropenem and the combination of meropenem and avibactam against strain NTBC091.1. The combination of meropenem and the compound of Example 10 has an MIC lower than the combination of meropenem and avibactam against strains NTBC091.1, NTBC096.1, and NTBC189, and an MIC similar to the combination of meropenem and avibactam against strain NTBC093. The combination of meropenem and the compound of Example 12 has an MIC lower than the combination of meropenem and avibactam against strain NTBC091.1.

Further MIC Data

The compound of Example 10 was examined further against a large panel of clinical strains of Enterobacteriaceae that are resistant to betalactam antibiotics such as meropenem, cefepime and ceftazidime as they produce OXA or KPC variants of SBL enzymes.

FIG. 1 shows data showing the effect of compound 10 against two panels of clinical strains of OXA positive enterobacteriaceae that are resistant to betalactam antibiotics such as meropenem, cefepime and ceftazidime. The data is presented in FIG. 1 in the standard cumulative MIC fashion.

FIG. 1A shows that, for example, 0% of the strains are susceptible to meropenem alone ("MEM") at an MIC of 1 µg/mL. However, the fraction of strains susceptible to the various antibiotics at 1 µg/mL rises to around 33% (clinical combination of inhibitor VNRX-5133 and antibiotic cefepime, "CEF/VNRX"); 63% (clinical combination of inhibitor avibactam, and antibiotic ceftazidime, "CAZ/AVI"); over 90% (combination of inhibitor Example 10 and antibiotic meropenem).

Similarly, FIG. 1B, which relates to a larger panel of clinical strains of OXA positive enterobacteriaceae that are resistant to betalactam antibiotics such as meropenem, cefepime and ceftazidime, confirms that meropenem has poor activity ($MIC_{50}=32$ µg/mL; $MIC_{90}>32$ µg/mL). Addition of 4 µg/mL of Example 10 restores sensitivity to meropenem ($MIC_{50}=0.12$ µg/mL; $MIC_{90}=0.5$ µg/mL). As a comparison, the clinical combination "CEF/VNRX" has $MIC_{50}/MIC_{90}$ values of 1 µg/mL and 2 µg/mL, respectively. The clinical combination "CAZ/AVI" has $MIC_{50}/MIC_{90}$ values of 2 µg/mL and 8 µg/mL, respectively.

FIG. 2 shows data showing the effect of compound 10 against a panel of clinical strains of KPC positive enterobacteriaceae that are resistant to betalactam antibiotics such as meropenem, cefepime and ceftazidime. The data is presented in standard cumulative MIC fashion. FIG. 2 shows that against KPC positive enterobacteriaceae, meropenem also has poor activity ($MIC_{50}>32$ µg/mL and $MIC_{90}>32$ µg/mL). Addition of 4 µg/mL of Example 10 restores sensitivity to meropenem ($MIC_{50}=0.12$ µg/mL; $MIC_{90}=2$ µg/mL). As a comparison, the clinical combination "CEF/VNRX" (inhibitor VNRX-5133 and antibiotic cefepime) has $MIC_{50}/MIC_{90}$ values of 1 µg/mL and 2 µg/mL, respectively. The clinical combination "CAZ/AVI" (inhibitor avibactam and antibiotic ceftazidime) has $MIC_{50}/MIC_{90}$ values of 1 µg/mL and 4 µg/mL, respectively.

The compound of Example 10 was also examined against a panel of 48 *A. baumannii* strains that are resistant to betalactam antibiotics such as meropenem, cefepime and ceftazidime as it produces OXA variants of SBL enzymes. The data is presented in FIG. 3 in the standard cumulative MIC fashion. For example, in the presence of 2 µg/mL of each inhibitor, 0% of the strains are susceptible to (i) meropenem alone ("MEM"), (ii) clinical combination of inhibitor VNRX-5133 and antibiotic cefepime, "CEF/VNRX"; or (iii) clinical combination of inhibitor avibactam, and antibiotic ceftazidime, "CAZ/AVI". By contrast, around 50% are susceptible to the compound of Example 10 in combination with the antibiotic meropenem. Similarly, in the presence of 16 µg/mL of each inhibitor, less than 10% of the strains are susceptible to (i) meropenem alone ("MEM"), (ii) clinical combination of inhibitor VNRX-5133 and antibiotic cefepime, "CEF/VNRX"; or (iii) clinical combination of inhibitor avibactam, and antibiotic ceftazidime, "CAZ/AVI". By contrast, close to 100% of strains are susceptible to the compound of Example 10 in combination with the antibiotic meropenem under these conditions. Referring to MIC values, it is shown that against this panel, meropenem has poor activity ($MIC_{50}$ 64 µg/mL and $MIC_{90}>64$ µg/mL). Addition of 4 µg/mL of Example 10 restores sensitivity to meropenem ($MIC_{50}$ 2 µg/mL and $MIC_{90}$ 8 µg/mL). As a comparison, the clinical combination "CEF/VNRX" shows poor activity against these OXA positive *Acinetobacter baumanni* clinical isolates, with $MIC_{50}/MIC_{90}$ values of 64 µg/mL and >64 µg/mL, respectively. Similarly, the clinical combination "CAZ/AVI" likewise shows poor activity against these OXA positive *Acinetobacter baumanni* clinical isolates, with inhibitor avibactam and antibiotic ceftazidime) has $MIC_{50}/MIC_{90}$ values of 64 µg/mL and >64 µg/mL, respectively.

In Vivo Efficacy of Compounds of the Invention

Compounds of the invention were further examined in animal efficacy models. Mice were infected in the thigh with:

(A) a KPC-expressing clinical strain of *Klebsiella pneumoniae* (NR-48977) [MIC (meropenem alone)=64 µg/mL; MIC (Meropenem+Example 10 at 4 µg/mL)=1 µg/mL]; or (B) an OXA-expressing clinical strain of *Klebsiella pneumoniae* (AC00783) [MIC (meropenem alone)=32 µg/mL; MIC (Meropenem+Example 10 at 4 µg/mL)= 0.25 µg/mL]; or (C) an OXA-expressing clinical strain of *Acinetobacter baumannii* (AC00445) [MIC (meropenem alone)=64 µg/mL; MIC (Meropenem+Example 10 at 4 µg/mL)=4 µg/mL].

Vehicle, meropenem alone or meropenem and a compound of the invention (Example 10) were administered by IV at 1, 3, 5 and 7 hours post infection. 9 hours post infection animals were sacrificed and the number of colony forming units (CFUs) was measured in order to quantify bacterial burden (colony forming units per gram thigh tissue, CFU/g).

Figure 4C:
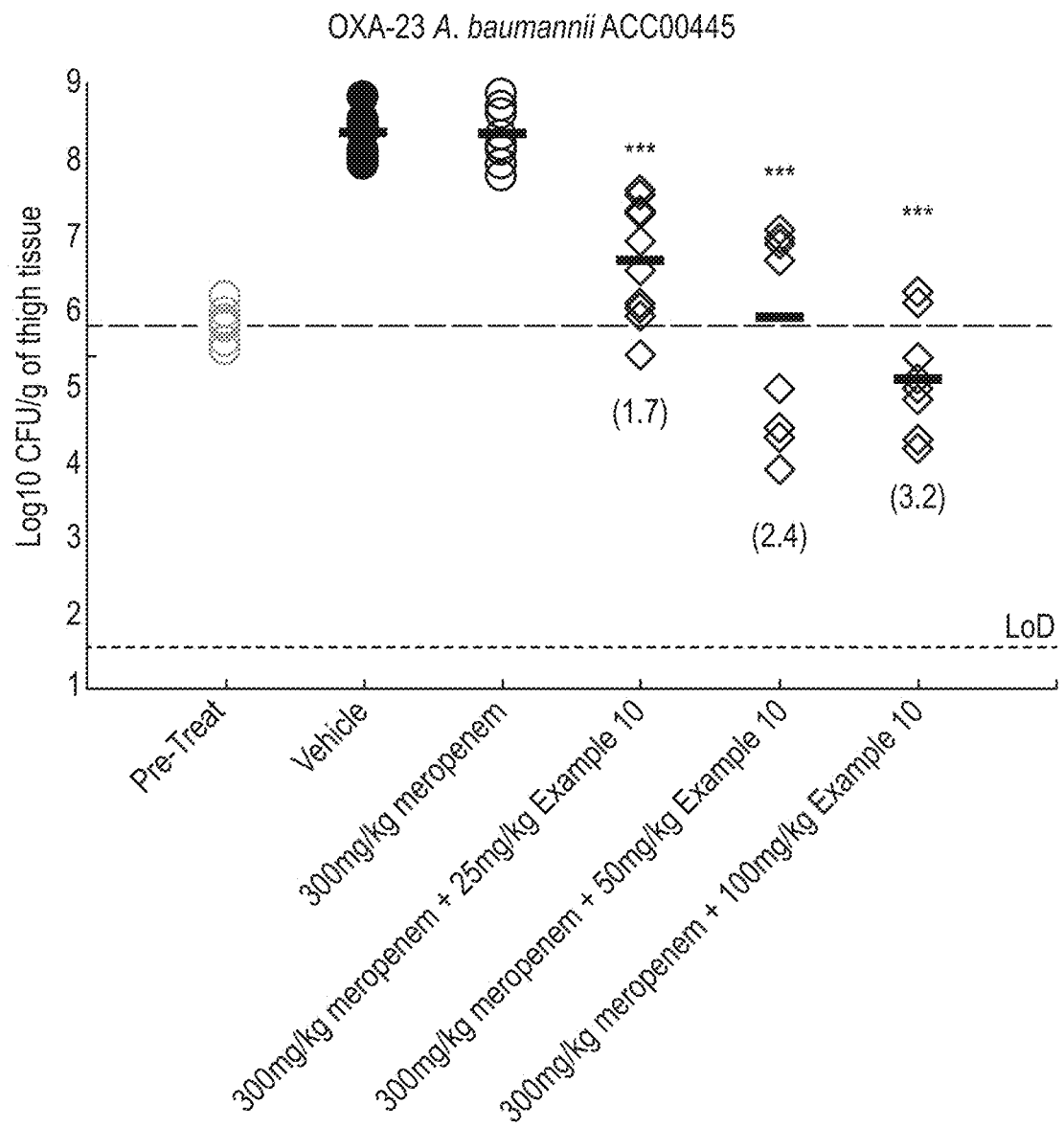

Results of these experiments, which were conducted with appropriate controls and statistical analysis, are shown in FIG. 4. For all three bacterial strains tested, a dose response can be seen with regard to the bacterial burden, as lower numbers of colony-forming units (CFUs) occur as the dose of Example 10 is increased, while administering a constant dose of meropenem.

The invention claimed is:

1. A method of treating or preventing a bacterial infection in a subject in need thereof,
said method comprising administering to the subject by parenteral administration an effective amount of a compound which is (2R,5R)-2-fluoro-7-oxo-1,6-diazabicyclo[3.2.1]octan-6-yl hydrogen sulphate or a pharmaceutically acceptable salt thereof.

2. The method of claim 1, wherein the parenteral administration is selected from administration by infusion, subcutaneous administration, intravenous administration, intramuscular administration, intrasternal administration and transdermal administration.

3. The method of claim 1, wherein the parenteral administration is administration by infusion.

4. The method of claim 1, wherein the parenteral administration is intravenous administration.

5. The method of claim 1, wherein the bacterial infection is caused by carbapenem resistant bacteria.

6. The method of claim 1, wherein the bacterial infection is caused by *Pseudomonas, Klebsiella, Escherichia, Enterobacter, Acinetobacter* or *Burkholderia*.

7. The method of claim 1, wherein the bacterial infection is selected from pneumonia, septic shock, urinary tract infection, gastrointestinal tract infections, skin infections and soft tissue infections.

8. The method of claim 1, further comprising administering an effective amount of a carbapenem antibiotic to the subject.

9. The method of claim 8, wherein the carbapenem antibiotic is meropenem.

10. The method of claim 1, wherein the compound is sodium (2R,5R)-2-fluoro-7-oxo-1,6-diazabicyclo[3.2.1]octan-6-yl sulphate.

11. A method of treating or preventing a bacterial infection in a subject in need thereof,
said method comprising administering to the subject an effective amount of a compound which is (2R,5R)-2-fluoro-7-oxo-1,6-diazabicyclo[3.2.1]octan-6-yl hydrogen sulphate or a pharmaceutically acceptable salt thereof;
wherein the bacterial infection is caused by Gram-negative bacteria.

12. The method of claim 11, wherein the Gram-negative bacteria are carbapenem resistant.

13. The method of claim 11, wherein the Gram-negative bacteria express one or more OXA β-lactamase enzymes and/or one or more KPC β-lactamase enzymes.

14. The method of claim 11, wherein the Gram-negative bacteria are of genus *Pseudomonas, Klebsiella, Escherichia, Enterobacter, Acinetobacter* or *Burkholderia*.

15. The method of claim 11, wherein the bacterial infection is caused by carbapenem-resistant *Acinetobacter baumannii*, carbapenem resistant Enterobacteriaceae, or *Pseudomonas aeruginosa*.

16. The method of claim 11, wherein the method comprises administering the compound to the subject by infusion, subcutaneous administration, intravenous administration, intramuscular administration, intrasternal administration or transdermal administration.

17. The method of claim 11, wherein the bacterial infection is selected from pneumonia, septic shock, urinary tract infection, gastrointestinal tract infections, skin infections and soft tissue infections.

18. The method of claim 11, further comprising administering an effective amount of a carbapenem antibiotic to the subject.

19. The method of claim 18, wherein the carbapenem antibiotic is meropenem.

20. The method of claim 11, wherein the compound is sodium (2R,5R)-2-fluoro-7-oxo-1,6-diazabicyclo[3.2.1]octan-6-yl sulphate.

21. A method of treating or preventing a bacterial infection in a subject in need thereof, said method comprising administering to the subject an effective amount of a compound which is (2R,5R)-2-fluoro-7-oxo-1,6-diazabicyclo[3.2.1]octan-6-yl hydrogen sulphate or a pharmaceutically acceptable salt thereof,
wherein the bacterial infection is selected from pneumonia, septic shock, urinary tract infection, gastrointestinal tract infections, skin infections and soft tissue infections.

22. The method of claim 21, wherein the bacterial infection is a hospital-acquired infection.

23. The method of claim 21, wherein bacterial infection is caused by carbapenem resistant bacteria.

24. The method of claim 21, wherein the bacterial infection is caused by bacteria of genus *Pseudomonas, Klebsiella, Escherichia, Enterobacter, Acinetobacter* or *Burkholderia*.

25. The method of claim 21, wherein the bacterial infection is caused by carbapenem-resistant *Acinetobacter baumannii*, carbapenem resistant Enterobacteriaceae, or *Pseudomonas aeruginosa*.

26. The method of claim 21, wherein the parenteral administration is selected from administration by infusion, subcutaneous administration, intravenous administration, intramuscular administration, intrasternal administration and transdermal administration.

27. The method of claim 21, further comprising administering an effective amount of a carbapenem antibiotic to the subject.

28. The method of claim 27, wherein the carbapenem antibiotic is meropenem.

29. The method of claim 21, wherein the compound is sodium (2R,5R)-2-fluoro-7-oxo-1,6-diazabicyclo[3.2.1]octan-6-yl sulphate.

* * * * *